(12) United States Patent
Brochu et al.

(10) Patent No.: US 9,340,548 B2
(45) Date of Patent: May 17, 2016

(54) SUBSTITUTED PYRAZOLO[3,4-A]CARBAZOLES AS HEPATITIS C INHIBITORS

(75) Inventors: Christian Brochu, Blainville, CA (US); Chantal Grand-Maitre, Boisbriand, CA (US); Marc-Andre Joly, Terrebonne, CA (US); Cyrille Kuhn, Danbury, CT (US); Megan Bertrand-Laperle, Laval, CA (US); Marc Pesant, St. Colomban, CA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 145 days.

(21) Appl. No.: 14/240,636

(22) PCT Filed: Aug. 22, 2012

(86) PCT No.: PCT/CA2012/050577
§ 371 (c)(1),
(2), (4) Date: Jun. 30, 2014

(87) PCT Pub. No.: WO2013/026162
PCT Pub. Date: Feb. 28, 2013

(65) Prior Publication Data
US 2015/0291592 A1 Oct. 15, 2015

Related U.S. Application Data

(60) Provisional application No. 61/526,942, filed on Aug. 24, 2011.

(51) Int. Cl.
| A61K 31/4162 | (2006.01) |
| C07D 231/54 | (2006.01) |
| C07D 487/04 | (2006.01) |
| C07D 513/04 | (2006.01) |
| A61K 31/4196 | (2006.01) |
| A61K 31/4245 | (2006.01) |
| A61K 31/4439 | (2006.01) |
| A61K 31/4545 | (2006.01) |
| A61K 31/497 | (2006.01) |

(52) U.S. Cl.
CPC .......... *C07D 487/04* (2013.01); *A61K 31/4162* (2013.01); *A61K 31/4196* (2013.01); *A61K 31/4245* (2013.01); *A61K 31/4439* (2013.01); *A61K 31/4545* (2013.01); *A61K 31/497* (2013.01); *C07D 513/04* (2013.01)

(58) Field of Classification Search
CPC .......................... A61K 31/4162; C07D 231/54
USPC ........................................ 514/410; 548/358.5
See application file for complete search history.

(56) References Cited

FOREIGN PATENT DOCUMENTS

CA        2516254 A1        8/2004

OTHER PUBLICATIONS

International Search Report, form PCT/ISA/210, and Written Opinion, form PCT/ISA/237, for corresponding application PCT/CA2012/050577, date of mailing Nov. 16, 2012.
Avanesova et al., Indole Derivatives, Li. Dialkylaminoethyl Esters of Isomeric Dihydro-11H-Benz(a)Carbazole Carboxylic Acids, Institute of Fine Organic Chemistry, 1974, pp. 720-725.

*Primary Examiner* — Douglas M Willis
(74) *Attorney, Agent, or Firm* — Michael P. Morris; Edward S. Lazer

(57) ABSTRACT

The invention relates to compounds of Formula (I)

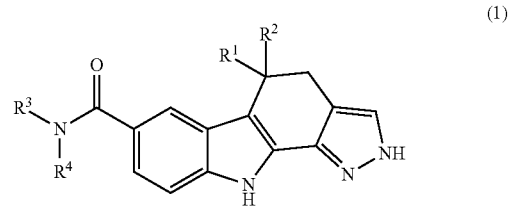

(1)

and pharmaceutically acceptable salts thereof, wherein $R^1$, $R^2$, $R^3$ and $R^4$ are defined herein, and their use for the treatment of hepatitis C viral infection.

6 Claims, No Drawings

SUBSTITUTED PYRAZOLO[3,4-A]CARBAZOLES AS HEPATITIS C INHIBITORS

RELATED APPLICATION

This application claims benefit of U.S. Ser. No. 61/526,942 filed Aug. 24, 2011, which is herein incorporated by reference.

FIELD OF THE INVENTION

This invention relates to tetrahydro-azafluorene analogs and their use in inhibiting entry of hepatitis C virus (HCV) into a cell, pharmaceutical compositions containing the same, and methods of using the same as agents for treatment of HCV infection.

BACKGROUND OF THE INVENTION

It is estimated that at least 170 million persons worldwide are infected with the hepatitis C virus. Acute HCV infection progresses to chronic infection in a high number of cases, and, in some infected individuals, chronic infection leads to serious liver diseases such as cirrhosis and hepatocellular carcinoma.

WO 2009/103022 discloses derivatives of substituted fused ring cycloindoles which inhibit entry of a hepatitis C virus into a cell. US 2010-0190773 discloses heterocyclic compounds for use as inhibitors of mitogen-activated protein kinase-activated protein kinase-2.

SUMMARY OF THE INVENTION

This invention provides novel compounds which inhibit entry of hepatitis C virus into a cell as measured by a HCV pseudo-particle/luciferase assay.

Further objects of this invention arise for the one skilled in the art from the following description and the examples.

Representative embodiments of the compound aspect of the invention are described below, while other embodiments of the compound aspect of the invention are described throughout the specification, for example under the heading "Preferred Embodiments" beginning at page 20.

Embodiment 1 provides a compound of Formula (I) or salt thereof:

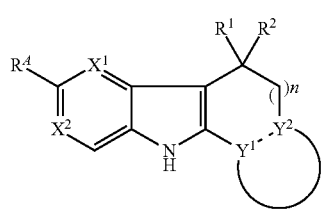

(I)

wherein:
$X^1$ and $X^2$ are each independently $CR^B$ or N;
$R^B$ is H, $(C_{1-6})$haloalkyl, halo, —O—$(C_{1-6})$alkyl, $NH_2$, $NH(C_{1-6})$alkyl or $N((C_{1-6})$alkyl$)_2$;
$Y^1$ and $Y^2$ are linked to form a heteroaryl or heterocyclyl ring wherein each said heterocyclyl and heteroaryl is optionally substituted 1 to 2 times with $R^B$;
------ is a single or double bond;

$R^1$ and $R^2$ are each independently $(C_{1-6})$alkyl optionally mono- or disubstituted with —O—$(C_{1-6})$alkyl, $NH_2$, $NH(C_{1-6})$alkyl or $N((C_{1-6})$alkyl$)_2$; or
$R^1$ and $R^2$, together with the carbon to which they are attached, are linked to form a $(C_{3-7})$cycloalkyl group or a 3- to 7-membered heterocyclyl, wherein said cycloalkyl and heterocyclyl are each optionally mono- or di-substituted with $(C_{1-6})$alkyl;
$R^A$ is —C(=O)N($R^3$)($R^4$), —C(=O)O($R^4$), heterocyclyl or heteroaryl, wherein each said heterocyclyl and heteroaryl is optionally substituted 1 to 3 times with $R^{41}$;
$R^3$ is H or $(C_{1-6})$alkyl optionally mono- or di-substituted with —O—$(C_{1-6})$alkyl, $NH_2$, $NH(C_{1-6})$alkyl, $N((C_{1-6})$alkyl$)_2$, —C(=O)—$(C_{1-6})$alkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —C(=O)—$NH_2$, —C(=O)—$NH(C_{1-6})$alkyl or —C(=O)—$N((C_{1-6})$alkyl$)_2$;
$R^4$ is H, $(C_{3-7})$cycloalkyl, —$(C_{1-6})$alkyl-heterocyclyl, —$(C_{1-6})$alkyl-heteroaryl, aryl, heterocyclyl or heteroaryl, wherein each said alkyl, cycloalkyl, aryl, heterocyclyl and heteroaryl, either alone or in combination with another radical, is optionally substituted 1 to 3 times with $R^{41}$; or
$R^3$ and $R^4$, together with the N atom to which they are attached, are linked to form a heterocyclyl or heteroaryl, wherein said heterocyclyl and heteroaryl are each optionally substituted 1 to 3 times with $R^{41}$;
$R^{41}$ is each independently selected from the group consisting of halo, oxo, cyano, nitro, $R^{42}$, —C(=O)—$R^{42}$, —C(=O)O$R^{42}$, —O$R^{42}$, —S$R^{42}$, —SO$R^{42}$, —$SO_2R^{42}$, —N($R^{43}$)$R^{42}$, —C(=O)—N($R^{43}$)$R^{42}$, —N($R^{43}$)—C(=O)$R^{42}$, —O—C(=O)—N($R^{43}$)$R^{42}$ and —$SO_2$—N($R^{43}$)$R^{42}$;
$R^{42}$ is each independently selected from the group consisting of H, $(C_{1-6})$alkyl, $(C_{3-7})$cycloalkyl, —$(C_{1-6})$alkyl-heterocyclyl, —$(C_{1-6})$alkyl-heteroaryl, heterocyclyl and heteroaryl, wherein each said alkyl, cycloalkyl, aryl, heterocyclyl and heteroaryl, either alone or in combination with another radical, is optionally substituted with 1 to 3 substituents each independently selected from the group consisting of:
halo, cyano, OH, —COOH, —O—$(C_{1-6})$alkyl, $(C_{3-7})$cycloalkyl, $(C_{1-6})$haloalkyl, —C(=O)—$(C_{1-6})$alkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —C(=O)—$NH_2$, —C(=O)—$NH(C_{1-6})$alkyl, —C(=O)—$N((C_{1-6})$alkyl$)_2$, —$NH_2$, —$NH(C_{1-6})$alkyl, —$N((C_{1-6})$alkyl$)_2$, —NH—C(=O)($C_{1-6})$alkyl and $(C_{1-6})$alkyl optionally mono- or di-substituted with OH or —O—$(C_{1-6})$alkyl;
$R^{43}$ is H or $(C_{1-6})$alkyl; and
n is 0, 1 or 2.

Embodiment 2 provides a compound of embodiment 1, or a pharmaceutically acceptable salt thereof, wherein $X^1$ is CH or N.

Embodiment 3 provides a compound of embodiment 1 or 2, or a pharmaceutically acceptable salt thereof, wherein $X^2$ is CH or N.

Embodiment 4 provides a compound of embodiments 1, 2 or 3, or a pharmaceutically acceptable salt thereof, wherein $X^1$ is CH.

Embodiment 5 provides a compound of any one of embodiments 1-4 or a pharmaceutically acceptable salt thereof, wherein $X^2$ is CH.

Embodiment 6 provides a compound of any one of embodiments 1-5 or a pharmaceutically acceptable salt thereof, wherein $Y^1$ and $Y^2$ are linked to form a 5- or 6-membered heteroaryl ring optionally substituted 1 to 2 times with $(C_{1-6})$alkyl, —O—$(C_{1-6})$alkyl, $NH_2$, $NH(C_{1-6})$alkyl or $N((C_{1-6})$alkyl$)_2$; and ------ is a single or double bond.

Embodiment 7 provides a compound of any one of embodiments 1-6, or a pharmaceutically acceptable salt thereof, wherein $Y^1$ and $Y^2$ are linked to form a 5- or 6-membered heteroaryl ring selected from the group consisting of:

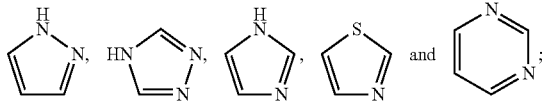

optionally mono-substituted with $(C_{1-3})$alkyl, $NH_2$, $NH(C_{1-3})$alkyl or $N((C_{1-3})$alkyl$)_2$; and
------ is a single or double bond.

Embodiment 8 provides a compound of any one of embodiments 1-7, or a pharmaceutically acceptable salt thereof, wherein $R^1$ is $(C_{1-3})$alkyl optionally mono- or di-substituted with —O—$(C_{1-6})$alkyl, $NH_2$, $NH(C_{1-6})$alkyl or $N((C_{1-6})$alkyl$)_2$;
$R^2$ is $(C_{1-3})$alkyl optionally mono- or di-substituted with —O—$(C_{1-6})$alkyl, $NH_2$, $NH(C_{1-6})$alkyl or $N((C_{1-6})$alkyl$)_2$; or
$R^1$ and $R^2$, together with the carbon to which they are attached, are linked to form a $(C_{3-7})$cycloalkyl group, optionally mono- or di-substituted with $(C_{1-3})$alkyl.

Embodiment 9 provides a compound of any one of embodiments 1-8, or a pharmaceutically acceptable salt thereof, wherein $R^1$ and $R^2$ are each $CH_3$; or $R^1$ and $R^2$ and the carbon to which they are attached are linked to form a $(C_{3-4})$cycloalkyl group optionally mono-substituted with $(C_{1-3})$alkyl.

Embodiment 10 provides a compound of any one of embodiments 1-9, or a pharmaceutically acceptable salt thereof, wherein $R^A$ is —C(=O)N($R^3$)($R^4$), —C(=O)O($R^4$), heterocyclyl or heteroaryl, wherein each said heterocyclyl and heteroaryl is optionally substituted 1 to 2 times with $R^{41}$;
$R^{41}$ is each independently selected from the group consisting of $R^{42}$, —C(=O)—$R^{42}$, —$SO_2R^{42}$ and —N($R^{43}$)$R^{42}$;
$R^{42}$ is each independently selected from the group consisting of —$(C_{1-6})$alkyl, $(C_{3-7})$cycloalkyl, —$(C_{1-6})$alkyl-heterocyclyl, —$(C_{1-6})$alkyl-heteroaryl, heterocyclyl and heteroaryl, wherein each said alkyl, cycloalkyl, aryl, heterocyclyl and heteroaryl, either alone or in combination with another radical, is optionally substituted with 1 to 2 substituents each independently selected from the group consisting of:
halo, OH, —O—$(C_{1-6})$alkyl, $(C_{1-6})$haloalkyl, —$SO_2NH_2$, —$SO_2$—NH$(C_{1-6})$alkyl, —$SO_2$—N$((C_{1-6})$alkyl$)_2$, —$SO_2$$(C_{1-6})$alkyl, —$NH_2$, —NH$(C_{1-6})$alkyl, —N$((C_{1-6})$alkyl$)_2$ and $(C_{1-6})$alkyl optionally mono- or di-substituted with OH or —O—$(C_{1-6})$alkyl;
$R^{43}$ is H or $(C_{1-6})$alkyl.

Embodiment 11 provides a compound of any one of embodiments 1-10, or a pharmaceutically acceptable salt thereof, wherein $R^A$ is —C(=O)N($R^3$)($R^4$).

Embodiment 12 provides a compound of any one of embodiments 1-11, or a pharmaceutically acceptable salt thereof, wherein $R^3$ is H or $(C_{1-6})$alkyl.

Embodiment 13 provides a compound of any one of embodiments 1-12, or a pharmaceutically acceptable salt thereof, wherein $R^3$ is H.

Embodiment 14 provides a compound of any one of embodiments 1-13 or a pharmaceutically acceptable salt thereof, wherein $R^4$ is $(C_{1-6})$alkyl, $(C_{3-7})$cycloalkyl, —$(C_{1-6})$alkyl-heterocyclyl, —$(C_{1-6})$alkyl-heteroaryl, heterocyclyl or heteroaryl, wherein each said alkyl, cycloalkyl, heterocyclyl and heteroaryl, either alone or in combination with another radical, is optionally mono- or di-substituted with $R^{41}$;
$R^{41}$ is each independently selected from the group consisting of $R^{42}$, —C(=O)—$R^{42}$, —C(=O)O$R^{42}$, —O$R^{42}$, —$SO_2R^{42}$, —N(H)$R^{42}$, —N(H)—C(=O)$R^{42}$ and —C(=O)—N(H)$R^{42}$;
$R^{42}$ is each independently selected from the group consisting of H, $(C_{3-7})$cycloalkyl, —$(C_{1-6})$alkyl-heterocyclyl, —$(C_{1-6})$alkyl-heteroaryl, heterocyclyl and heteroaryl, wherein each said alkyl, cycloalkyl, heterocyclyl and heteroaryl, either alone or in combination with another radical, is optionally mono- or di-substituted with substituents each independently selected from the group consisting of:
halo, OH, —O—$(C_{1-6})$alkyl, $(C_{3-7})$cycloalkyl, $(C_{1-6})$haloalkyl, —$SO_2NH_2$, —$SO_2$—NH$(C_{1-6})$alkyl, —$SO_2$—N$((C_{1-6})$alkyl$)_2$, —$SO_2$$(C_{1-6})$alkyl, —C(=O)—$NH_2$, —C(=O)—NH$(C_{1-6})$alkyl, —C(=O)—N$((C_{1-6})$alkyl$)_2$, —$NH_2$, —NH$(C_{1-6})$alkyl, —N$((C_{1-6})$alkyl$)_2$, —NH—C(=O)$(C_{1-6})$alkyl and $(C_{1-6})$alkyl optionally mono- or di-substituted with OH or Embodiment 15 provides a compound of any one of embodiments 1-14, or a pharmaceutically acceptable salt thereof, wherein $R^4$ is heterocyclyl, optionally mono- or di-substituted with $R^{41}$,
$R^{41}$ is each independently selected from the group consisting of $R^{42}$, —C(=O)—$R^{42}$ and —$SO_2R^{42}$;
$R^{42}$ is each independently selected from the group consisting of $(C_{1-6})$alkyl, $(C_{5-7})$cycloalkyl, —$(C_{1-4})$alkyl-heterocyclyl, —$(C_{1-4})$alkyl-heteroaryl, heterocyclyl and heteroaryl, wherein each said alkyl, cycloalkyl, heterocyclyl and heteroaryl, either alone or in combination with another radical, is optionally mono- or di-substituted with substituents each independently selected from the group consisting of:
halo, OH, —O—$(C_{1-6})$alkyl, —$SO_2NH_2$, —$SO_2$—NH$(C_{1-6})$alkyl, —$SO_2$—N$((C_{1-6})$alkyl$)_2$, —$SO_2$$(C_{1-6})$alkyl, —$NH_2$, —NH$(C_{1-6})$alkyl, —N$((C_{1-6})$alkyl$)_2$, —NH—C(=O)$(C_{1-6})$alkyl and Embodiment 16 provides a compound of any one of embodiments 1-15, or a pharmaceutically acceptable salt thereof, wherein $R^4$ is a nitrogen containing heterocyclyl, optionally mono- or di-substituted with $R^{41}$,
$R^{41}$ is each independently selected from the group consisting of $R^{42}$, —C(=O)—$R^{42}$ and —$SO_2R^{42}$;
$R^{42}$ is each independently selected from the group consisting of $(C_{1-6})$alkyl, $(C_{5-7})$cycloalkyl, —$(C_{1-4})$alkyl-heterocyclyl, —$(C_{1-4})$alkyl-heteroaryl, heterocyclyl and heteroaryl, wherein each said alkyl, cycloalkyl, heterocyclyl and heteroaryl, either alone or in combination with another radical, is optionally mono- or di-substituted with substituents each independently selected from the group consisting of:
halo, OH, —O—$(C_{1-6})$alkyl, —$SO_2NH_2$, —$SO_2$—NH$(C_{1-6})$alkyl, —$SO_2$—N$((C_{1-6})$alkyl$)_2$, —$SO_2$$(C_{1-6})$alkyl, —$NH_2$, —NH$(C_{1-6})$alkyl, —N$((C_{1-6})$alkyl$)_2$, —NH—C(=O)$(C_{1-6})$alkyl and $(C_{1-6})$alkyl.

Embodiment 17 provides a compound of any one of embodiments 1-16, or a pharmaceutically acceptable salt thereof, wherein n is 1.

Embodiment 18 provides a compound of embodiment 1, or a pharmaceutically acceptable salt thereof, having a formula

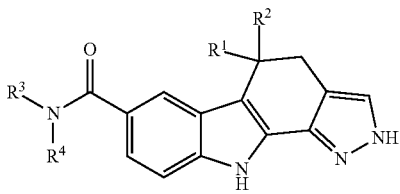

wherein:

$R^1$ and $R^2$ are each independently $(C_{1-6})$alkyl optionally mono- or di-substituted with —O—$(C_{1-6})$alkyl, $NH_2$, $NH(C_{1-6})$alkyl or $N((C_{1-6})$alkyl$)_2$; or $R^1$ and $R^2$, together with the carbon to which they are attached, are linked to form a $(C_{3-7})$cycloalkyl group or a 3- to 7-membered heterocyclyl, wherein said cycloalkyl and heterocyclyl are each optionally mono- or di-substituted with $(C_{1-6})$alkyl;

$R^3$ is H or $(C_{1-6})$alkyl optionally mono- or di-substituted with —O—$(C_{1-6})$alkyl, $NH_2$, $NH(C_{1-6})$alkyl, $N((C_{1-6})$alkyl$)_2$, —C(=O)—$(C_{1-6})$alkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —C(=O)—$NH_2$, —C(=O)—$NH(C_{1-6})$alkyl or —C(=O)—$N((C_{1-6})$alkyl$)_2$;

$R^4$ is H, $(C_{1-6})$alkyl, $(C_{3-7})$cycloalkyl, —$(C_{1-6})$alkyl-heterocyclyl, —$(C_{1-6})$alkyl-heteroaryl, aryl, heterocyclyl or heteroaryl, wherein each said alkyl, cycloalkyl, aryl, heterocyclyl and heteroaryl, either alone or in combination with another radical, is optionally substituted 1 to 3 times with $R^{41}$; or $R^3$ and $R^4$, together with the N atom to which they are attached, are linked to form a heterocyclyl or heteroaryl, wherein said heterocyclyl and heteroaryl are each optionally substituted 1 to 3 times with $R^{41}$;

$R^{41}$ is each independently selected from the group consisting of halo, oxo, cyano, nitro, $R^{42}$, —C(=O)—$R^{42}$, —C(=O)OR$^{42}$, —OR$^{42}$, —SR$^{42}$, —SOR$^{42}$, —$SO_2R^{42}$, —N(R$^{43}$)R$^{42}$, —C(=O)—N(R$^{43}$)R$^{42}$, —N(R$^{43}$)—C(=O)R$^{42}$, —O—C(=O)—N(R$^{43}$)R$^{42}$ and —$SO_2$—N(R$^{43}$)R$^{42}$;

$R^{42}$ is each independently selected from the group consisting of H, $(C_{1-6})$alkyl, $(C_{3-7})$cycloalkyl, —$(C_{1-6})$alkyl-heterocyclyl, —$(C_{1-6})$alkyl-heteroaryl, heterocyclyl and heteroaryl, wherein each said alkyl, cycloalkyl, aryl, heterocyclyl and heteroaryl, either alone or in combination with another radical, is optionally substituted with 1 to 3 substituents each independently selected from the group consisting of:

halo, cyano, OH, —COOH, —O—$(C_{1-6})$alkyl, $(C_{3-7})$cycloalkyl, $(C_{1-6})$haloalkyl, —C(=O)—$(C_{1-6})$alkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —C(=O)—$NH_2$, —C(=O)—$NH(C_{1-6})$alkyl, —C(=O)—$N((C_{1-6})$alkyl$)_2$, —$NH_2$, —$NH(C_{1-6})$alkyl, —$N((C_{1-6})$alkyl$)_2$, —NH—C(=O)$(C_{1-6})$alkyl and $(C_{1-6})$alkyl optionally mono- or di-substituted with OH or —O—$(C_{1-6})$alkyl;

$R^{43}$ is H or $(C_{1-6})$alkyl.

Embodiment 19 provides a compound of embodiment 18, or a pharmaceutically acceptable salt thereof, wherein $R^1$ is $(C_{1-3})$alkyl optionally mono- or di-substituted with —O—$(C_{1-6})$alkyl, $NH_2$, $NH(C_{1-6})$alkyl or $N((C_{1-6})$alkyl$)_2$;

$R^2$ is $(C_{1-3})$alkyl optionally mono- or di-substituted with —O—$(C_{1-6})$alkyl, $NH_2$, $NH(C_{1-6})$alkyl or $N((C_{1-6})$alkyl$)_2$; or $R^1$ and $R^2$, together with the carbon to which they are attached, are linked to form a $(C_{3-7})$cycloalkyl group, optionally mono- or di-substituted with $(C_{1-3})$alkyl.

Embodiment 20 provides a compound of embodiment 18 or 19, or a pharmaceutically acceptable salt thereof, wherein $R^1$ and $R^2$ are each $CH_3$; or $R^1$ and $R^2$ and the carbon to which they are attached are linked to form a $(C_{3-4})$cycloalkyl group optionally mono-substituted with $(C_{1-3})$alkyl.

Embodiment 21 provides a compound of any one of embodiments 18-20, or a pharmaceutically acceptable salt thereof, wherein $R^3$ is H or $(C_{1-6})$alkyl.

Embodiment 22 provides a compound of any one of embodiments 18-21, or a pharmaceutically acceptable salt thereof, wherein $R^3$ is H.

Embodiment 23 provides a compound of any one of embodiments 18-22, or a pharmaceutically acceptable salt thereof, wherein $R^4$ is $(C_{1-6})$alkyl, $(C_{3-7})$cycloalkyl, —$(C_{1-6})$alkyl-heterocyclyl, —$(C_{1-6})$alkyl-heteroaryl, heterocyclyl or heteroaryl, wherein each said alkyl, cycloalkyl, heterocyclyl and heteroaryl, either alone or in combination with another radical, is optionally mono- or di-substituted with $R^{41}$;

$R^{41}$ is each independently selected from the group consisting of $R^{42}$, —C(=O)—$R^{42}$, —C(=O)OR$^{42}$, —OR$^{42}$, —$SO_2R^{42}$, —N(H)R$^{42}$, —N(H)—C(=O)R$^{42}$ and —C(=O)—N(H)R$^{42}$;

$R^{42}$ is each independently selected from the group consisting of H, $(C_{3-7})$cycloalkyl, —$(C_{1-6})$alkyl-heterocyclyl, —$(C_{1-6})$alkyl-heteroaryl, heterocyclyl and heteroaryl, wherein each said alkyl, cycloalkyl, heterocyclyl and heteroaryl, either alone or in combination with another radical, is optionally mono- or di-substituted with substitutents each independently selected from the group consisting of:

halo, OH, —O—$(C_{1-6})$alkyl, $(C_{3-7})$cycloalkyl, $(C_{1-6})$haloalkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —C(=O)—$NH_2$, —C(=O)—$NH(C_{1-6})$alkyl, —C(=O)—$N((C_{1-6})$alkyl$)_2$, —$NH_2$, —$NH(C_{1-6})$alkyl, —$N((C_{1-6})$alkyl$)_2$, —NH—C(=O)$(C_{1-6})$alkyl and $(C_{1-6})$alkyl optionally mono- or di-substituted with OH or —O—$(C_{1-6})$alkyl.

Embodiment 24 provides a compound of any one of embodiments 18-23, or a pharmaceutically acceptable salt thereof, wherein $R^4$ is heterocyclyl, optionally mono- or di-substituted with $R^{41}$, $R^{41}$ is each independently selected from the group consisting of $R^{42}$, —C(=O)—$R^{42}$ and —$SO_2R^{42}$;

$R^{42}$ is each independently selected from the group consisting of $(C_{1-6})$alkyl, $(C_{5-7})$cycloalkyl, —$(C_{1-4})$alkyl-heterocyclyl, —$(C_{1-4})$alkyl-heteroaryl, heterocyclyl and heteroaryl, wherein each said alkyl, cycloalkyl, heterocyclyl and heteroaryl, either alone or in combination with another radical, is optionally mono- or di-substituted with substitutents each independently selected from the group consisting of:

halo, OH, —O—$(C_{1-6})$alkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —$NH_2$, —$NH(C_{1-6})$alkyl, —$N((C_{1-6})$alkyl$)_2$, —NH—C(=O)$(C_{1-6})$alkyl and $(C_{1-6})$alkyl.

Embodiment 25 provides a compound of any one of embodiments 18-24, or a pharmaceutically acceptable salt thereof, wherein $R^4$ is a nitrogen containing heterocyclyl, optionally mono- or di-substituted with $R^{41}$, $R^{41}$ is each independently selected from the group consisting of $R^{42}$, —C(=O)—$R^{42}$ and —$SO_2R^{42}$;

$R^{42}$ is each independently selected from the group consisting of $(C_{1-6})$alkyl, $(C_{5-7})$cycloalkyl, —$(C_{1-4})$alkyl-heterocyclyl, —$(C_{1-4})$alkyl-heteroaryl, heterocyclyl and heteroaryl, wherein each said alkyl, cycloalkyl, heterocyclyl and heteroaryl, either alone or in combination with another radical, is optionally mono- or di-substituted with substitutents each independently selected from the group consisting of:

halo, OH, —O—($C_{1-6}$)alkyl, —$SO_2NH_2$, —$SO_2$—NH($C_{1-6}$)alkyl, —$SO_2$—N(($C_{1-6}$)alkyl)$_2$, —$SO_2$($C_{1-6}$)alkyl, —$NH_2$, —NH($C_{1-6}$)alkyl, —N(($C_{1-6}$)alkyl)$_2$, —NH—C(=O)($C_{1-6}$)alkyl and ($C_{1-6}$)alkyl.

Another aspect of this invention provides compounds of any one of the compound embodiments, or a pharmaceutically acceptable salt thereof, as a medicament.

Also within the scope of this invention is the use of a compound of Formula (I), or a pharmaceutically acceptable salt thereof, for the manufacture of a medicament for the treatment or prevention of hepatitis C viral infection in a human being.

Included within the scope of this invention is a pharmaceutical composition comprising a compound of Formula (I), or a pharmaceutically acceptable salt thereof, and a pharmaceutically acceptable carrier.

According to a further aspect of this embodiment the pharmaceutical composition according to this invention further comprises a therapeutically effective amount of at least one other antiviral agent.

The invention also provides the use of a pharmaceutical composition as described hereinabove for the treatment of a hepatitis C viral infection in a human being having or at risk of having the infection.

Another important aspect of the invention involves a method of treating or preventing a hepatitis C viral infection in a human being by administering to the human being an anti-hepatitis C virally effective amount of a compound of the invention, a pharmaceutically acceptable salt thereof, or a composition as described above, alone or in combination with at least one other antiviral agent, administered together or separately.

Still another aspect of this invention relates to a method of inhibiting the entry of hepatitis C virus into a cell comprising exposing the virus to an effective amount of the compound of the invention, or a salt thereof, under conditions where entry of hepatitis C virus into a cell is inhibited.

Further included in the scope of the invention is the use of a compound of the invention, or a salt thereof, to inhibit the entry of hepatitis C virus into a cell.

Yet another aspect of this invention provides a method of inhibiting replication of hepatitis C virus through the entry pathway in a human being by administering a compound of the invention, including a pharmaceutically acceptable salt thereof.

Another aspect of this invention provides a method of inhibiting the entry of the hepatitis C virus into a cell in a human being by administering a compound of the invention, including a pharmaceutically acceptable salt thereof.

DETAILED DESCRIPTION OF PREFERRED EMBODIMENTS

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the first named subgroup is the radical attachment point, for example, the substituent "—$C_{1-3}$-alkyl-aryl" means an aryl group which is bound to a $C_{1-3}$-alkyl-group, with the $C_{1-3}$-alkyl group bound to the core. Unless specifically stated otherwise, for groups comprising two or more subgroups, the substituent may be attached to either subgroup.

In case a compound of the present invention is depicted in form of a chemical name and as a formula in case of any discrepancy the formula shall prevail. An asterisk or the designation, ----, may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers, atropisomers) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

One skilled in the art would know how to separate, enrich, or selectively prepare the enantiomers of the compounds of the present invention. Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include but not limited to chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, including but not limited to GC, HPLC, CE, or NMR, and assignment of absolute configuration and conformation, including but not limited to CD, ORD, X-ray crystallography, or NMR.

The term "halo" generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-3}$-alkyl embraces the radicals $H_3C$—, $H_3C$—$CH_2$—, $H_3C$—$CH_2$—$CH_2$— and $H_3C$—CH($CH_3$)—.

The term "carbocyclyl" or "carbocycle" as used herein, either alone or in combination with another radical, means a mono-, bi- or tricyclic ring structure consisting of 3 to 14 carbon atoms. The term "carbocycle" refers to fully saturated and aromatic ring systems and partially saturated ring systems. The term "carbocycle" encompasses fused, bridged and spirocyclic systems.

The term "$C_{3-n}$-cycloalkyl", wherein n is an integer 4 to n, either alone or in combination with another radical, denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "aryl" as used herein, either alone or in combination with another radical, denotes a carbocyclic aromatic monocyclic group containing 6 carbon atoms which may be further fused to at least one other 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring system including aromatic ring systems containing one or more heteroatoms selected from N, O or S(O)$_r$, wherein r=0, 1 or 2, consisting of 3 to 14 ring atoms wherein none of the heteroatoms is part of the aromatic ring. The term "heterocyclyl" or "heterocycle" is intended to include all the possible isomeric forms. Thus, the term "heterocyclyl" or "heterocyclyl" includes the following exemplary structures which are not depicted as radicals as each form may be attached through a covalent bond to any atom so long as appropriate valences are maintained:

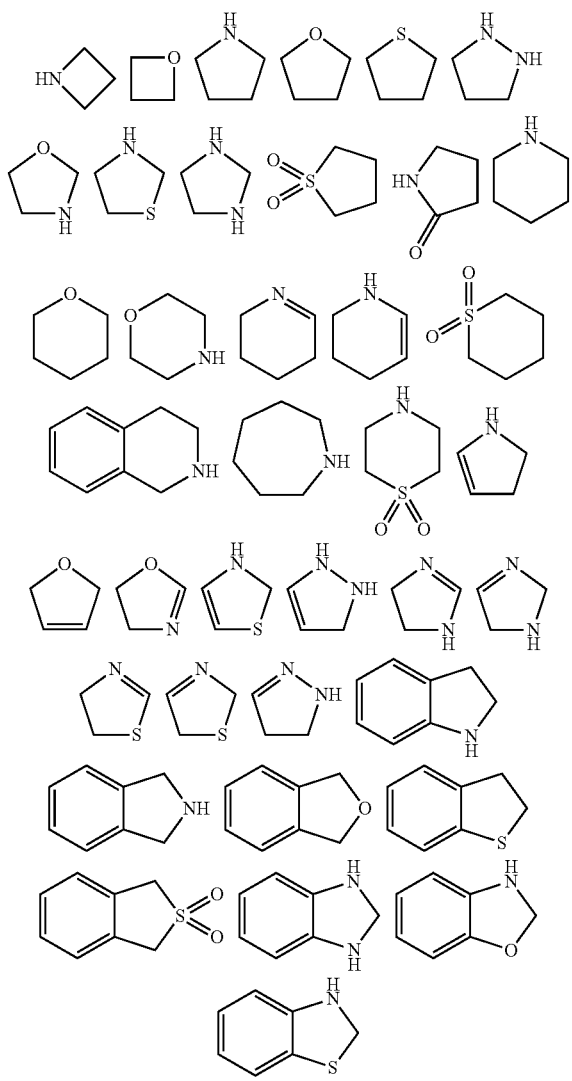

The term "heteroaryl" means a mono- or polycyclic-ring system containing one or more heteroatoms selected from N, O or S(O)$_r$, wherein r=0, 1 or 2, consisting of 5 to 14 ring atoms wherein at least one of the heteroatoms is part of an aromatic ring. The term "heteroaryl" is intended to include all the possible isomeric forms. Thus, the term "heteroaryl" includes the following exemplary structures which are not depicted as radicals as each form may be attached through a covalent bond to any atom so long as appropriate valences are maintained:

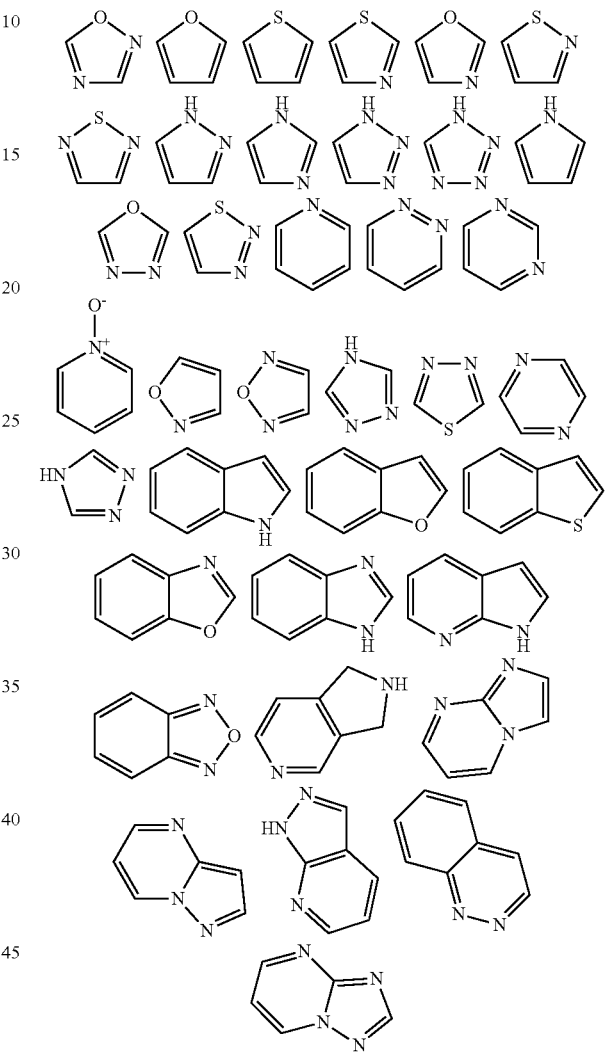

Many of the terms given above may be used repeatedly in the definition of a formula or group and in each case have one of the meanings given above, independently of one another.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term "antiviral agent" as used herein means an agent (compound or biological) that is effective to inhibit the formation and/or replication of a virus in a human being. This includes agents that interfere with either host or viral mechanisms necessary for the formation and/or replication of a virus in a human being. Such agents can be selected from: another anti-HCV agent, HIV inhibitor, HAV inhibitor and HBV inhibitor.

The term "other anti-HCV agent" as used herein means those agents that are effective for diminishing or preventing the progression of hepatitis C related symptoms of disease. Such agents can be selected from: immunomodulatory agents, inhibitors of HCV NS3 protease, inhibitors of HCV NS5A, inhibitors of HCV polymerase or inhibitors of another target in the HCV life cycle. Examples of anti-HCV agents include, α-(alpha), β-(beta), δ-(delta), γ-(gamma), ω-(omega) or τ-(tau) interferon, pegylated α-interferon, ribavirin, amantadine, taribavirin (Viramidine), Nitazoxannide, ABT-267 and BMS-791325.

The term "immunomodulatory agent" as used herein includes those agents (compounds or biologicals) that are effective to enhance or potentiate the immune system response in a human being. Immunomodulatory agents include, but are not limited to, inosine monophosphate dehydrogenase inhibitors, class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, α-, β-, δ-, ω-, and τ-interferons, while examples of class II interferons include, but are not limited to, γ-interferons.

The term "inhibitor of HCV NS3 protease" as used herein means an agent (compound or biological) that is effective to inhibit the function of HCV NS3 protease in a human being. Inhibitors of HCV NS3 protease include, for example, the candidates telaprevir, boceprevir, danoprevir, vaniprevir, ABT-450, ACH-1625, BMS-650032, BI 201335, GS9256, IDX320, MK-5172, VX-985, ACH-2684, GS9541 and TMC43530.

The term "inhibitor of HCV polymerase" as used herein means an agent (compound or biological) that is effective to inhibit the function of an HCV polymerase in a human being. This includes, for example, nucleoside analogs or non-nucleosides inhibitors of HCV polymerase and inhibitors of HCV NS5B polymerase. Inhibitors of HCV polymerase include for example, the candidates tegobuvir, filibuvir, BI 207127, RG-7128, IDX184, PSI-7977, MK-3281, VX-222, ANA598, ABT-333, ABT-072, INX189, PSI-938, RG-7348, JTK-853, RG-7432, TMC-649128, GS-6620, BMS-791325 and IDX-375.

The term "inhibitor of HCV NS5A" as used herein means an agent (compound or biological) that is effective to inhibit the function of HCV NS5A in a human being. Inhibitors of HCV NS5A include, for example, ABT-267, BMS-824393, BMS-790052, ITMN-10050, ITMN-9916, EDP-239, AZD7295, GS-5885, GSK-2336805, IDX-380, IDX-719, ACH-2928, PPI-437, PPI-668, PPI-833 and PPI-461.

The term "inhibitor of another target in the HCV life cycle" as used herein means an agent (compound or biological) that is effective to inhibit the formation and/or replication of HCV in a human being by interfering with either host or HCV viral targets necessary for the HCV life cycle or agents which specifically inhibit in HCV cell culture assays through an undefined or incompletely defined mechanism. Inhibitors of another target in the HCV life cycle include, for example, agents that inhibit viral targets such as Core, E1, E2, p7, NS2/3 protease, NS3 helicase, NS4A, NS5A, NS5B polymerase, and internal ribosome entry site (IRES), or host targets such as cyclophilin A or B, phosphatidylinositol 4-kinase IIIα, CD81, SR-B1, Claudin 1, VAP-A, VAP-B. Specific examples of inhibitors of another target in the HCV life cycle include SCY-635, ITX5061, NOV-205, AZD7295, BIT-225, NA808, MK-1220, PF-4878691, MX-3253, GS 9450, TMC-647055, CF-102, ISIS-14803, GS9190, NIM-811, and DEBIO-025.

The term "HIV inhibitor" as used herein means an agent (compound or biological) that is effective to inhibit the formation and/or replication of HIV in a human being. This includes agents that interfere with either host or viral mechanisms necessary for the formation and/or replication of HIV in a human being. HIV inhibitors include, for example, nucleoside inhibitors, non-nucleoside inhibitors, protease inhibitors, fusion inhibitors and integrase inhibitors.

The term "HAV inhibitor" as used herein means an agent (compound or biological) that is effective to inhibit the formation and/or replication of HAV in a human being. This includes agents that interfere with either host or viral mechanisms necessary for the formation and/or replication of HAV in a human being. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a human being. This includes agents that interfere with either host or viral mechanisms necessary for the formation and/or replication of HBV in a human being. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, to prevent the appearance of symptoms of the disease.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Preferred Embodiments

In the following preferred embodiments, groups and substituents of the compounds of Formula (I) according to this invention are described in detail.

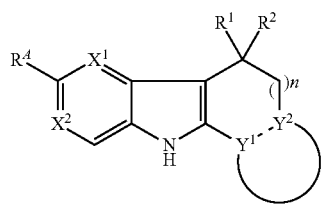

(I)

Any and each of the definitions below may be combined with each other.

$X^1$:

$X^1$-A: $X^1$ is $CR^B$ or N;

$R^B$ is H, $(C_{1-6})$haloalkyl, halo, —O—$(C_{1-6})$alkyl, $NH_2$, $NH(C_{1-6})$alkyl or $N((C_{1-6})alkyl)_2$.

$X^1$—B: $X^1$ is CH or N.

$X^1$—C: $X^1$ is CH.

$X^2$:

$X^2$-A: $X^2$ is $CR^B$ or N;

$R^B$ is H, $(C_{1-6})$haloalkyl, halo, —O—$(C_{1-6})$alkyl, $NH_2$, $NH(C_{1-6})$alkyl or $N((C_{1-6})alkyl)_2$.

$X^2$—B: $X^2$ is CH or N.

$X^2$—C: $X^2$ is CH.

$Y^1/Y^2$:

$Y^1/Y^2$-A: $Y^1$ and $Y^2$ are linked to form a heteroaryl or heterocyclyl ring wherein each said heterocyclyl and heteroaryl is optionally substituted 1 to 2 times with $R^B$; $R^B$ is H, $(C_{1-6})$haloalkyl, halo, —O—$(C_{1-6})$alkyl, $NH_2$, $NH(C_{1-6})$alkyl or $N((C_{1-6})alkyl)_2$;

------ is a single or double bond.

$Y^1/Y^2$—B: $Y^1$ and $Y^2$ are linked to form a 5- or 6-membered heteroaryl ring optionally substituted 1 to 2 times with $(C_{1-6})$alkyl, —O—$(C_{1-6})$alkyl, $NH_2$, $NH(C_{1-6})$alkyl or $N((C_{1-6})alkyl)_2$;

------ is a single or double bond.

$Y^1/Y^2$—C: $Y^1$ and $Y^2$ are linked to form a 5- or 6-membered heteroaryl ring selected from the group consisting of:

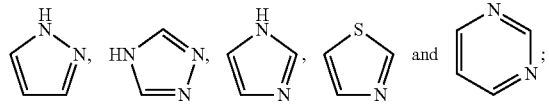

optionally mono-substituted with $(C_{1-3})$alkyl, $NH_2$, $NH(C_{1-3})$alkyl or $N((C_{1-3})alkyl)_2$; and ------ is a single or double bond.

$R^1/R^2$:

$R^1/R^2$-A: $R^1$ is $(C_{1-6})$alkyl optionally mono- or di-substituted with —O—$(C_{1-6})$alkyl, $NH_2$, $NH(C_{1-6})$alkyl or $N((C_{1-6})alkyl)_2$;

$R^2$ is $(C_{1-6})$alkyl optionally mono- or di-substituted with —O—$(C_{1-6})$alkyl, $NH_2$, $NH(C_{1-6})$alkyl or $N((C_{1-6})alkyl)_2$; or $R^1$ and $R^2$, together with the carbon to which they are attached, are linked to form a $(C_{3-7})$cycloalkyl group or a 3- to 7-membered heterocyclyl, wherein said cycloalkyl and heterocyclyl are each optionally mono- or di-substituted with $(C_{1-6})$alkyl.

$R^1/R^2$—B: $R^1$ is $(C_{1-3})$alkyl optionally mono- or di-substituted with —O—$(C_{1-6})$alkyl, $NH_2$, $NH(C_{1-6})$alkyl or $N((C_{1-6})alkyl)_2$;

$R^2$ is $(C_{1-3})$alkyl optionally mono- or di-substituted with —O—$(C_{1-6})$alkyl, $NH_2$, $NH(C_{1-6})$alkyl or $N((C_{1-6})alkyl)_2$; or $R^1$ and $R^2$, together with the carbon to which they are attached, are linked to form a $(C_{3-7})$cycloalkyl group, optionally mono- or di-substituted with $(C_{1-3})$alkyl.

$R^1/R^2$—C: $R^1$ and $R^2$ are each $CH_3$; or $R^1$ and $R^2$ and the carbon to which they are attached are linked to form a $(C_{3-4})$cycloalkyl group optionally mono-substituted with $(C_{1-3})$alkyl.

$R^A$:

$R^A$-A: $R^A$ is —C(=O)N($R^3$)($R^4$), —C(=O)O($R^4$), heterocyclyl or heteroaryl, wherein each said heterocyclyl and heteroaryl is optionally substituted 1 to 3 times with $R^{41}$;

$R^{41}$ is each independently selected from the group consisting of halo, oxo, cyano, nitro, $R^{42}$, —C(=O)—$R^{42}$, —C(=O)O$R^{42}$, —O$R^{42}$, —S$R^{42}$, —SO$R^{42}$, —SO$_2R^{42}$, —N($R^{43}$)$R^{42}$, —C(=O)—N($R^{43}$)$R^{42}$, —N($R^{43}$)—C(=O)$R^{42}$, —O—C(=O)—N($R^{43}$)$R^{42}$ and —SO$_2$—N($R^{43}$)$R^{42}$;

$R^{42}$ is each independently selected from the group consisting of H, $(C_{1-6})$alkyl, $(C_{3-7})$cycloalkyl, —$(C_{1-6})$alkyl-heterocyclyl, —$(C_{1-6})$alkyl-heteroaryl, aryl, heterocyclyl and heteroaryl, wherein each said alkyl, cycloalkyl, aryl, heterocyclyl and heteroaryl, either alone or in combination with another radical, is optionally substituted with 1 to 3 substituents each independently selected from the group consisting of:
  halo, cyano, OH, —COOH, —O—$(C_{1-6})$alkyl, $(C_{3-7})$cycloalkyl, $(C_{1-6})$haloalkyl, —C(=O)—$(C_{1-6})$alkyl, —SO$_2$NH$_2$, —SO$_2$—NH$(C_{1-6})$alkyl, —SO$_2$—N$((C_{1-6})$alkyl$)_2$, —SO$_2(C_{1-6})$alkyl, —C(=O)—NH$_2$, —C(=O)—NH$(C_{1-6})$alkyl, —C(=O)—N$((C_{1-6})$alkyl$)_2$, —NH$_2$, —NH$(C_{1-6})$alkyl, —N$((C_{1-6})$alkyl$)_2$, —NH—C(=O)$(C_{1-6})$alkyl and $(C_{1-6})$alkyl optionally mono- or di-substituted with OH or —O—$(C_{1-6})$alkyl; and
$R^{43}$ is H or $(C_{1-6})$alkyl.
$R^A$—B: $R^A$ is —C(=O)N(R$^3$)(R$^4$), —C(=O)O(R$^4$), heterocyclyl or heteroaryl, wherein each said heterocyclyl and heteroaryl is optionally substituted 1 to 2 times with $R^{41}$;
  $R^{41}$ is each independently selected from the group consisting of $R^{42}$, —C(=O)—$R^{42}$, —SO$_2$R$^{42}$ and —N(R$^{43}$)R$^{42}$;
  $R^{42}$ is each independently selected from the group consisting of —$(C_{1-6})$alkyl, $(C_{3-7})$cycloalkyl, —$(C_{1-6})$alkyl-heterocyclyl, —$(C_{1-6})$alkyl-heteroaryl, aryl, heterocyclyl and heteroaryl, wherein each said alkyl, cycloalkyl, aryl, heterocyclyl and heteroaryl, either alone or in combination with another radical, is optionally substituted with 1 to 2 substituents each independently selected from the group consisting of:
    halo, OH, —O—$(C_{1-6})$alkyl, $(C_{1-6})$haloalkyl, —SO$_2$NH$_2$, —SO$_2$—NH$(C_{1-6})$alkyl, —SO$_2$—N$((C_{1-6})$alkyl$)_2$, —SO$_2(C_{1-6})$alkyl, —NH$_2$, —NH$(C_{1-6})$alkyl, —N$((C_{1-6})$alkyl$)_2$ and $(C_{1-6})$alkyl optionally mono- or di-substituted with OH or —O—$(C_{1-6})$alkyl;
  $R^{43}$ is H or $(C_{1-6})$alkyl.
$R^A$—C: $R^A$ is —C(=O)N(R$^3$)(R$^4$).
$R^3$:
$R^3$-A: $R^3$ is H or $(C_{1-6})$alkyl optionally mono- or di-substituted with —O—$(C_{1-6})$alkyl, NH$_2$, NH$(C_{1-6})$alkyl, N$((C_{1-6})$alkyl$)_2$, —C(=O)—$(C_{1-6})$alkyl, —SO$_2$NH$_2$, —SO$_2$—NH$(C_{1-6})$alkyl, —SO$_2$—N$((C_{1-6})$alkyl$)_2$, —SO$_2(C_{1-6})$alkyl, —C(=O)—NH$_2$, —C(=O)—NH$(C_{1-6})$alkyl or —C(=O)—N$((C_{1-6})$alkyl$)_2$.
$R^3$-B: $R^3$ is H or $(C_{1-6})$alkyl.
$R^3$-C: $R^3$ is H.
$R^4$:
$R^4$-A: $R^4$ is H, $(C_{3-7})$cycloalkyl, —$(C_{1-6})$alkyl-heterocyclyl, —$(C_{1-6})$alkyl-heteroaryl, aryl, heterocyclyl or heteroaryl, wherein each said alkyl, cycloalkyl, aryl, heterocyclyl and heteroaryl, either alone or in combination with another radical, is optionally substituted 1 to 3 times with $R^{41}$; or $R^3$ and $R^4$, together with the N atom to which they are attached, are linked to form a heterocyclyl or heteroaryl, wherein said heterocyclyl and heteroaryl are each optionally substituted 1 to 3 times with $R^{41}$;
  $R^{41}$ is each independently selected from the group consisting of halo, oxo, cyano, nitro, $R^{42}$, —C(=O)—$R^{42}$, —C(=O)OR$^{42}$, —OR$^{42}$, —SR$^{42}$, —SOR$^{42}$, —SO$_2$R$^{42}$, —N(R$^{43}$)R$^{42}$, —C(=O)—N(R$^{43}$)R$^{42}$, —N(R$^{43}$)—C(=O)R$^{42}$, —O—C(=O)—N(R$^{43}$)R$^{42}$ and —SO$_2$—N(R$^{43}$)R$^{42}$;
  $R^{42}$ is each independently selected from the group consisting of H, $(C_{1-6})$alkyl, $(C_{3-7})$cycloalkyl, —$(C_{1-6})$alkyl-heterocyclyl, —$(C_{1-6})$alkyl-heteroaryl, aryl, heterocyclyl and heteroaryl, wherein each said alkyl, cycloalkyl, aryl, heterocyclyl and heteroaryl, either alone or in combination with another radical, is optionally substituted with 1 to 3 substituents each independently selected from the group consisting of:
    halo, cyano, OH, —COOH, —O—$(C_{1-6})$alkyl, $(C_{3-7})$cycloalkyl, $(C_{1-6})$haloalkyl, —C(=O)—$(C_{1-6})$alkyl, —SO$_2$NH$_2$, —SO$_2$—NH$(C_{1-6})$alkyl, —SO$_2$—N$((C_{1-6})$alkyl$)_2$, —SO$_2(C_{1-6})$alkyl, —C(=O)—NH$_2$, —C(=O)—NH$(C_{1-6})$alkyl, —C(=O)—N$((C_{1-6})$alkyl$)_2$, —NH$_2$, —NH$(C_{1-6})$alkyl, —N$((C_{1-6})$alkyl$)_2$, —NH—C(=O)$(C_{1-6})$alkyl and $(C_{1-6})$alkyl optionally mono- or di-substituted with OH or —O—$(C_{1-6})$alkyl;
  $R^{43}$ is H or $(C_{1-6})$alkyl.
$R^4$—B: $R^4$ is $(C_{1-6})$alkyl, $(C_{3-7})$cycloalkyl, —$(C_{1-6})$alkyl-heterocyclyl, —$(C_{1-6})$alkyl-heteroaryl, heterocyclyl or heteroaryl, wherein each said alkyl, cycloalkyl, heterocyclyl and heteroaryl, either alone or in combination with another radical, is optionally mono- or di-substituted with $R^{41}$;
  $R^{41}$ is each independently selected from the group consisting of $R^{42}$, —C(=O)—$R^{42}$, —C(=O)OR$^{42}$, —OR$^{42}$, —SO$_2$R$^{42}$, —N(H)R$^{42}$, —N(H)—C(=O)R$^{42}$ and —C(=O)—N(H)R$^{42}$;
  $R^{42}$ is each independently selected from the group consisting of H, $(C_{1-6})$alkyl, $(C_{3-7})$cycloalkyl, —$(C_{1-6})$alkyl-heterocyclyl, —$(C_{1-6})$alkyl-heteroaryl, heterocyclyl and heteroaryl, wherein each said alkyl, cycloalkyl, heterocyclyl and heteroaryl, either alone or in combination with another radical, is optionally mono- or di-substituted with substitutents each independently selected from the group consisting of:
    halo, OH, —O—$(C_{1-6})$alkyl, $(C_{3-7})$cycloalkyl, $(C_{1-6})$haloalkyl, —SO$_2$NH$_2$, —SO$_2$—NH$(C_{1-6})$alkyl, —SO$_2$—N$((C_{1-6})$alkyl$)_2$, —SO$_2(C_{1-6})$alkyl, —C(=O)—NH$_2$, —C(=O)—NH$(C_{1-6})$alkyl, —C(=O)—N$((C_{1-6})$alkyl$)_2$, —NH$_2$, —NH$(C_{1-6})$alkyl, —N$((C_{1-6})$alkyl$)_2$, —NH—C(=O)$(C_{1-6})$alkyl and $(C_{1-6})$alkyl optionally mono- or di-substituted with OH or —O—$(C_{1-6})$alkyl.
$R^4$—C: $R^4$ is heterocyclyl, optionally mono- or di-substituted with $R^{41}$,
  $R^{41}$ is each independently selected from the group consisting of $R^{42}$, —C(=O)—$R^{42}$ and —SO$_2$R$^{42}$;
  $R^{42}$ is each independently selected from the group consisting of $(C_{1-6})$alkyl, $(C_{5-7})$cycloalkyl, —$(C_{1-4})$alkyl-heterocyclyl, —$(C_{1-4})$alkyl-heteroaryl, heterocyclyl and heteroaryl, wherein each said alkyl, cycloalkyl, heterocyclyl and heteroaryl, either alone or in combination with another radical, is optionally mono- or di-substituted with substitutents each independently selected from the group consisting of:
    halo, OH, —O—$(C_{1-6})$alkyl, —SO$_2$NH$_2$, —SO$_2$—NH$(C_{1-6})$alkyl, —SO$_2$—N$((C_{1-6})$alkyl$)_2$, —SO$_2(C_{1-6})$alkyl, —NH$_2$, —NH$(C_{1-6})$alkyl, —N$((C_{1-6})$alkyl$)_2$, —NH—C(=O)$(C_{1-6})$alkyl and $(C_{1-6})$alkyl.
$R^4$-D: $R^4$ is a nitrogen containing heterocyclyl, optionally mono- or di-substituted with $R^{41}$,
  $R^{41}$ is each independently selected from the group consisting of $R^{42}$, —C(=O)—$R^{42}$ and —SO$_2$R$^{42}$;
  $R^{42}$ is each independently selected from the group consisting of $(C_{1-6})$alkyl, $(C_{5-7})$cycloalkyl, —$(C_{1-4})$alkyl-heterocyclyl, —$(C_{1-4})$alkyl-heteroaryl, heterocyclyl and heteroaryl, wherein each said alkyl, cycloalkyl, heterocyclyl and heteroaryl, either alone or in combination with another radical, is optionally mono- or di-substituted with substitutents each independently selected from the group consisting of:
  halo, OH, —O—($C_{1-6}$)alkyl, —$SO_2NH_2$, —$SO_2$—NH($C_{1-6}$)alkyl, —$SO_2$—N(($C_{1-6}$)alkyl)$_2$, —$SO_2$($C_{1-6}$)alkyl, —$NH_2$, —NH($C_{1-6}$)alkyl, —N(($C_{1-6}$)alkyl)$_2$, —NH—C(=O)($C_{1-6}$)alkyl and ($C_{1-6}$)alkyl.

n:
n-A: n is 0, 1 or 2.
n-B: n is 1.

Examples of preferred subgeneric embodiments of the present invention are set forth in the following table, wherein each substituent group of each embodiment is defined according to the definitions set forth above:

| | $X^1$ | $X^2$ | $R^1/R^2$ | $R^4$ | $R^3$ | $R^4$ | n | $Y^1/Y^2$ |
|---|---|---|---|---|---|---|---|---|
| E-1 | $X^1$-A | $X^2$-A | $R^1/R^2$-B | $R^4$-C | $R^3$-B | $R^4$-B | n-A | $Y^1/Y^2$-B |
| E-2 | $X^1$-B | $X^2$-B | $R^1/R^2$-B | $R^4$-C | $R^3$-B | $R^4$-A | n-B | $Y^1/Y^2$-B |
| E-3 | $X^1$-B | $X^2$-B | $R^1/R^2$-C | $R^4$-B | $R^3$-B | $R^4$-B | n-B | $Y^1/Y^2$-A |
| E-4 | $X^1$-C | $X^2$-C | $R^1/R^2$-C | $R^4$-B | $R^3$-B | $R^4$-B | n-B | $Y^1/Y^2$-B |
| E-5 | $X^1$-C | $X^2$-C | $R^1/R^2$-C | $R^4$-C | $R^3$-C | $R^4$-C | n-B | $Y^1/Y^2$-C |
| E-6 | $X^1$-B | $X^2$-B | $R^1/R^2$-C | $R^4$-B | $R^3$-B | $R^4$-D | n-B | $Y^1/Y^2$-A |
| E-7 | $X^1$-C | $X^2$-C | $R^1/R^2$-C | $R^4$-B | $R^3$-B | $R^4$-D | n-B | $Y^1/Y^2$-B |
| E-8 | $X^1$-C | $X^2$-C | $R^1/R^2$-C | $R^4$-C | $R^3$-C | $R^4$-D | n-B | $Y^1/Y^2$-C |

In the following more preferred embodiments, groups and substituents of the compounds having the formula are described in detail.

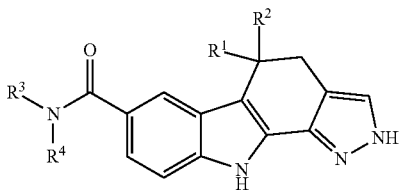

Any and each of the definitions below may be combined with each other.

$R^1/R^2$:

$R^1/R^2$-A: $R^1$ and $R^2$ are each independently ($C_{1-6}$)alkyl optionally mono- or di-substituted with —O—($C_{1-6}$)alkyl, $NH_2$, NH($C_{1-6}$)alkyl or N(($C_{1-6}$)alkyl)$_2$; or $R^1$ and $R^2$, together with the carbon to which they are attached, are linked to form a ($C_{3-7}$)cycloalkyl group or a 3- to 7-membered heterocyclyl, wherein said cycloalkyl and heterocyclyl are each optionally mono- or di-substituted with ($C_{1-6}$)alkyl.

$R^1/R^2$—B: $R^1$ is ($C_{1-3}$)alkyl optionally mono- or di-substituted with —O—($C_{1-6}$)alkyl, $NH_2$, NH($C_{1-6}$)alkyl or N(($C_{1-6}$)alkyl)$_2$;
  $R^2$ is ($C_{1-3}$)alkyl optionally mono- or di-substituted with —O—($C_{1-6}$)alkyl, $NH_2$, NH($C_{1-6}$)alkyl or N(($C_{1-6}$)alkyl)$_2$; or
  $R^1$ and $R^2$, together with the carbon to which they are attached, are linked to form a ($C_{3-7}$)cycloalkyl group, optionally mono- or di-substituted with ($C_{1-3}$)alkyl.

$R^1/R^2$—C: $R^1$ and $R^2$ are each $CH_3$; or
  $R^1$ and $R^2$ and the carbon to which they are attached are linked to form a ($C_{3-4}$)cycloalkyl group optionally mono-substituted with ($C_{1-3}$)alkyl.

$R^3$:

$R^3$-A: $R^3$ is H or ($C_{1-6}$)alkyl optionally mono- or di-substituted with —O—($C_{1-6}$)alkyl, $NH_2$, NH($C_{1-6}$)alkyl, N(($C_{1-6}$)alkyl)$_2$, —C(=O)—($C_{1-6}$)alkyl, —$SO_2NH_2$, —$SO_2$—NH($C_{1-6}$)alkyl, —$SO_2$—N(($C_{1-6}$)alkyl)$_2$, —$SO_2$($C_{1-6}$)alkyl, —C(=O)—$NH_2$, —C(=O)—NH($C_{1-6}$)alkyl or —C(=O)—N(($C_{1-6}$)alkyl)$_2$.

$R^3$—B: $R^3$ is H or ($C_{1-6}$)alkyl.

$R^3$—C: $R^3$ is H.

$R^4$:

$R^4$-A: $R^4$ is H, ($C_{3-7}$)cycloalkyl, —($C_{1-6}$)alkyl-heterocyclyl, —($C_{1-6}$)alkyl-heteroaryl, aryl, heterocyclyl or heteroaryl, wherein each said alkyl, cycloalkyl, aryl, heterocyclyl and heteroaryl, either alone or in combination with another radical, is optionally substituted 1 to 3 times with $R^{41}$; or
  $R^3$ and $R^4$, together with the N atom to which they are attached, are linked to form a heterocyclyl or heteroaryl, wherein said heterocyclyl and heteroaryl are each optionally substituted 1 to 3 times with $R^{41}$;

$R^{41}$ is each independently selected from the group consisting of halo, oxo, cyano, nitro, $R^{42}$, —C(=O)—$R^{42}$, —C(=O)$OR^{42}$, —$OR^{42}$, —$SR^{42}$, —$SOR^{42}$, —$SO_2R^{42}$, —N($R^{43}$)$R^{42}$, —C(=O)—N($R^{43}$)$R^{42}$, —N($R^{43}$)—C(=O)$R^{42}$, —O—C(=O)—N($R^{43}$)$R^{42}$ and —$SO_2$—N($R^{43}$)$R^{42}$;

$R^{42}$ is each independently selected from the group consisting of H, ($C_{1-6}$)alkyl, ($C_{3-7}$)cycloalkyl, —($C_{1-6}$)alkyl-heterocyclyl, —($C_{1-6}$)alkyl-heteroaryl, aryl, heterocyclyl and heteroaryl, wherein each said alkyl, cycloalkyl, aryl, heterocyclyl and heteroaryl, either alone or in combination with another radical, is optionally substituted with 1 to 3 substituents each independently selected from the group consisting of:
  halo, cyano, OH, —COOH, —O—($C_{1-6}$)alkyl, ($C_{3-7}$)cycloalkyl, ($C_{1-6}$)haloalkyl, —C(=O)—($C_{1-6}$)alkyl, —$SO_2NH_2$, —$SO_2$—NH($C_{1-6}$)alkyl, —$SO_2$—N(($C_{1-6}$)alkyl)$_2$, —$SO_2$($C_{1-6}$)alkyl, —C(=O)—$NH_2$, —C(=O)—NH($C_{1-6}$)alkyl, —C(=O)—N(($C_{1-6}$)alkyl)$_2$, —$NH_2$, —NH($C_{1-6}$)alkyl, —N(($C_{1-6}$)alkyl)$_2$, —NH—C(=O)($C_{1-6}$)alkyl and ($C_{1-6}$)alkyl optionally mono- or di-substituted with OH or —O—($C_{1-6}$)alkyl;

$R^{43}$ is H or ($C_{1-6}$)alkyl.

$R^4$—B: $R^4$ is ($C_{1-6}$)alkyl, ($C_{3-7}$)cycloalkyl, —($C_{1-6}$)alkyl-heterocyclyl, —($C_{1-6}$)alkyl-heteroaryl, heterocyclyl or heteroaryl, wherein each said alkyl, cycloalkyl, heterocyclyl and heteroaryl, either alone or in combination with another radical, is optionally mono- or di-substituted with $R^{41}$;

$R^{41}$ is each independently selected from the group consisting of $R^{42}$, —C(=O)—$R^{42}$, —C(=O)$OR^{42}$, —$OR^{42}$, —$SO_2R^{42}$, —N(H)$R^{42}$, —N(H)—C(=O)$R^{42}$ and —C(=O)—N(H)$R^{42}$;

$R^{42}$ is each independently selected from the group consisting of H, ($C_{1-6}$)alkyl, ($C_{3-7}$)cycloalkyl, —($C_{1-6}$)alkyl-heterocyclyl, —($C_{1-6}$)alkyl-heteroaryl, heterocyclyl and heteroaryl, wherein each said alkyl, cycloalkyl, heterocyclyl and heteroaryl, either alone or in combination with another radical, is optionally mono- or di-substituted with substitutents each independently selected from the group consisting of:
  halo, OH, —O—($C_{1-6}$)alkyl, ($C_{3-7}$)cycloalkyl, ($C_{1-6}$)haloalkyl, —$SO_2NH_2$, —$SO_2$—NH($C_{1-6}$)alkyl, —$SO_2$—N(($C_{1-6}$)alkyl)$_2$, —$SO_2$($C_{1-6}$)alkyl, —C(=O)—$NH_2$, —C(=O)—NH($C_{1-6}$)alkyl, —C(=O)—N(($C_{1-6}$)alkyl)$_2$, —$NH_2$, —NH($C_{1-6}$)alkyl, —N(($C_{1-6}$)alkyl)$_2$, —NH—C(=O)($C_{1-6}$)alkyl and ($C_{1-6}$)alkyl optionally mono- or di-substituted with OH or —O—($C_{1-6}$)alkyl.

$R^4$—C: $R^4$ is heterocyclyl, optionally mono- or di-substituted with $R^{41}$, $R^{41}$ is each independently selected from the group consisting of $R^{42}$, —C(=O)—$R^{42}$ and —SO$_2R^{42}$;

$R^{42}$ is each independently selected from the group consisting of (C$_{1-6}$)alkyl, (C$_{5-7}$)cycloalkyl, —(C$_{1-4}$)alkyl-heterocyclyl, —(C$_{1-4}$)alkyl-heteroaryl, heterocyclyl and heteroaryl, wherein each said alkyl, cycloalkyl, heterocyclyl and heteroaryl, either alone or in combination with another radical, is optionally mono- or di-substituted with substitutents each independently selected from the group consisting of:

halo, OH, —O—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO$_2$(C$_{1-6}$)alkyl, —NH$_2$, —NH(C$_{1-6}$)alkyl, —N((C$_{1-6}$)alkyl)$_2$, —NH—C(=O)(C$_{1-6}$)alkyl and (C$_{1-6}$)alkyl.

$R^4$-D: $R^4$ is a nitrogen containing heterocyclyl, optionally mono- or di-substituted with $R^{41}$, $R^{41}$ is each independently selected from the group consisting of $R^{42}$, —C(=O)—$R^{42}$ and —SO$_2R^{42}$;

$R^{42}$ is each independently selected from the group consisting of (C$_{1-6}$)alkyl, (C$_{5-7}$)cycloalkyl, —(C$_{1-4}$)alkyl-heterocyclyl, —(C$_{1-4}$)alkyl-heteroaryl, heterocyclyl and heteroaryl, wherein each said alkyl, cycloalkyl, heterocyclyl and heteroaryl, either alone or in combination with another radical, is optionally mono- or di-substituted with substitutents each independently selected from the group consisting of:

halo, OH, —O—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO$_2$(C$_{1-6}$)alkyl, —NH$_2$, —NH(C$_{1-6}$)alkyl, —N((C$_{1-6}$)alkyl)$_2$, —NH—C(=O)(C$_{1-6}$)alkyl and (C$_{1-6}$)alkyl.

Examples of more preferred subgeneric embodiments of the present invention are set forth in the following table, wherein each substituent group of each embodiment is defined according to the definitions set forth above:

|      | $R^1/R^2$ | $R^3$ | $R^4$ |
| ---- | --------- | ----- | ----- |
| E-9  | $R^1/R^2$-A | $R^3$-B | $R^4$-C |
| E-10 | $R^1/R^2$-B | $R^3$-B | $R^4$-B |
| E-11 | $R^1/R^2$-B | $R^3$-B | $R^4$-C |
| E-12 | $R^1/R^2$-B | $R^3$-B | $R^4$-D |
| E-13 | $R^1/R^2$-C | $R^3$-C | $R^4$-B |
| E-14 | $R^1/R^2$-C | $R^3$-C | $R^4$-C |
| E-15 | $R^1/R^2$-C | $R^3$-C | $R^4$-D |

Examples of most preferred compounds according to this invention are each single compound listed in Tables 1-5.

Pharmaceutical Composition

Suitable preparations for administering the compounds of the invention will be apparent to those with ordinary skill in the art and include for example tablets, pills, capsules, suppositories, lozenges, troches, solutions, syrups, elixirs, sachets, injectables, inhalatives and powders. The content of the pharmaceutically active compound(s) should be in the range from 0.05 to 90 wt.-%, preferably 0.1 to 50 wt.-% of the composition as a whole.

Suitable tablets may be obtained, for example, by mixing one or more compounds according to the invention with known excipients, for example inert diluents, carriers, disintegrants, adjuvants, surfactants, binders and/or lubricants. The tablets may also consist of several layers.

Combination Therapy

Combination therapy is contemplated wherein a compound of the invention, or a pharmaceutically acceptable salt thereof, is co-administered with at least one additional agent selected from: an antiviral agent, an immunomodulatory agent, an inhibitor of HCV NS3 protease, an inhibitor of HCV polymerase, an inhibitor of HCV NS5A, an inhibitor of another target in the HCV life cycle, an HIV inhibitor, an HAV inhibitor and an HBV inhibitor. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of the invention, or a pharmaceutically acceptable salt thereof.

The dose range of the compounds of the invention applicable per day is usually from 0.01 to 100 mg/kg of body weight, preferably from 0.1 to 50 mg/kg of body weight. Each dosage unit may conveniently contain from 5% to 95% active compound (w/w). Preferably such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

When the composition of this invention comprises a combination of a compound of the invention and one or more additional therapeutic or prophylactic agent, both the compound and the additional agent should be present at dosage levels of between about 10 to 100%, and more preferably between about 10 and 80% of the dosage normally administered in a monotherapy regimen.

EXAMPLES

Other features and advantages of the present invention will become apparent from the following more detailed Examples which illustrate, by way of example, the principles of the invention. Temperatures are given in degrees Celsius. Solution percentages express a weight to volume relationship, and solution ratios express a volume to volume relationship, unless stated otherwise.

Compounds and intermediates can be purified on a Teledyne ISCO Combiflash $R_f$ System at 254 nm using commercial normal phase silica 4-120 g Redisep $R_f$ or Silicycle columns at a flow rate of 18-85 mL/min depending on column size. Mass spectral analyses are recorded using flow injection analysis mass spectrometry or Waters Acquity Ultraperformance LC System consisting of a sample organizer, PDA detector, column manager, sample manager, binary solvent manager and SQ detector.

Preparative RP-HPLC is performed under standard conditions using one of the following specific measuring conditions:

Compounds are purified by preparative RP-HPLC under standard conditions using a Waters SunFire Prep OBD C18 column (5 µm, 19×50 mm) eluting with a linear MeOH gradient containing 10 mM Ammonium Formate (pH 3.8) over 10 min at 30 ml/min. Fractions containing the desired product are pooled and lyophilized Compounds are purified by preparative RP-HPLC under standard conditions using a Waters XBridge Prep OBD C18 (5 µm, 19×50 mm) eluting with a linear MeOH gradient containing 10 mM Ammonium Bicarbonate (pH 10) over 10 min at 30 ml/min. Fractions containing the desired product are pooled and lyophilized.

Analytical UPLC is performed under standard conditions using one of the following specific measuring conditions:

Analytical UPLC is also carried out under standard conditions using (AB) a Waters ACQUITY UPLC BEH C18 column (1.8 µm, 2.1×30 mm) eluting with a linear methanol gradient containing 10 mM Ammonium Bicarbonate (pH 10) over 2.2 min at 0.75 ml/min or (AF) a Waters ACQUITY UPLC® HSS C18 column (1.8 μm, 2.1×30 mm) eluting with a linear MeOH gradient containing 10 mM Ammonium Formate (pH 3.8) over 2.3 min at 0.8 ml/min.

Analytical UPLC is also carried out under standard conditions using a Waters ACQUITY UPLC HSS C18 column (1.8 μm, 2.1×30 mm) eluting with a linear MeOH gradient containing 10 mM Ammonium Formate (pH 3.8) over 2.3 min at 0.8 ml/min.

Abbreviations used in the examples include:
Ac: acetyl; AcOH: acetic acid; BOC or Boc: tert-butyloxycarbonyl; Bu: butyl; DCM: dichloromethane; DIPEA: diisopropylethylamine; DMAc: dimethylacetamide; DMAP: 4-dimethylaminopyridine; DMEM: Dulbecco's modified Eagle's medium; DMF: N,N-dimethylformamide; DMSO: dimethylsulfoxide; dppf: 1,1'-diphenylphosphinylferrocene; EDCI: 1-[3-(dimethylamino)propyl]-3-ethylcarbodiimide hydrochloride; Et: ethyl; Et$_2$O: diethyl ether; EtOAc: ethyl acetate; EtOH: ethanol; FBS: Fetal bovine serum; HATU: [O-(7-azabenzotriazol-1-yl)-1,1,3,3-tetramethyluronium hexafluorophosphate]; HEPES: 4-(2-hydroxyethyl)-1-piperazineethanesulfonic acid; Hex: hexanes; HPLC: high performance liquid chromatography; HSS: high strength silica; i-Pr: isopropyl; LiHMDS: lithium bis(trimethylsilyl)amide; Me: methyl; MeCN: acetonitrile; MeOH: methanol; MS: mass spectrometry (FIA MS-flow injection analysis mass spectrometry UPLC: Ultraperformance Liquid Chromatography); m/z: mass-to-charge ratio; [M+H]$^+$: protonated molecular ion; NEAA: non-essential amino acids; NMP: N-methyl pyrrolidinone; OBD: optimum bed density; PDA: photodiode array; RP: reverse phase; RT: room temperature (18 to 22° C.); TEA: triethylamine; TFA: trifluoroacetic acid; THF: tetrahydrofuran; TMS: trimethylsilyl; VSV: vesicular stomatitis virus.

Example 1

Preparation of Intermediates 1a3 and 1a5

Step 1:

To a 0° C. mixture of NaH (60% in oil, 0.65 g, 15.0 mmol) in EtOH (0.1 mL) and ether (30 mL) is added a solution of cyclohexanone (1.9 g, 15.0 mmol, Combi-blocks) and ethylformate (1.8 mL, 22.5 mmol) in ether (40 mL) over a period of 1 h. The reaction mixture is allowed to warm to RT overnight. EtOH (1.5 mL) is added and the reaction mixture is stirred for 1 h. Water (40 mL) is added and the ether layer is washed with water. The aqueous layer is acidified with 6N HCl and extracted with ether. The combined organic extracts are washed with water, brine, dried over MgSO$_4$ and concentrated to afford 1a1 which is used as such in the next step.

Step 2:

1a1 (1.15 g, 7.5 mmol) is dissolved in MeOH (30 mL), NaOAc (1.4 g, 16 mmol) and water (30 mL) are added and the resulting solution 1-1 is cooled to 0° C. In a separate vessel, 4-aminobenzoic acid (1.0 g, 7.5 mmol, Aldrich) is cooled to 0° C., taken up in water (30 mL) and concentrated HCl is added (2.2 mL). To this is added a saturated solution of NaNO$_2$ (0.9 g, 15 mmol, 9 mL of water). The solution is then added to solution 1-1 and the reaction mixture is allowed to stir for 30 min. The precipitate is filtered, washed with water and dried to provide 1a2.

Step 3:

1a2 (1.75 g, 6.4 mmol) is taken up in formic acid (70 mL) and heated at 100° C. for 12 h. The reaction is cooled to RT and poured into cold water (100 mL). The resulting precipitate is filtered, washed with cold water and dried to provide 1a3.

Step 4:

1a3 suspended in MeOH (25 mL) is treated with diazomethane (0.68M, 10 mL). MeOH (50 mL) and diazomethane (15 mL) are again added and the reaction mixture is stirred at RT for 1 h. The solvents are evaporated in vacuo and the residue is dried under vacuum to provide 1a4.

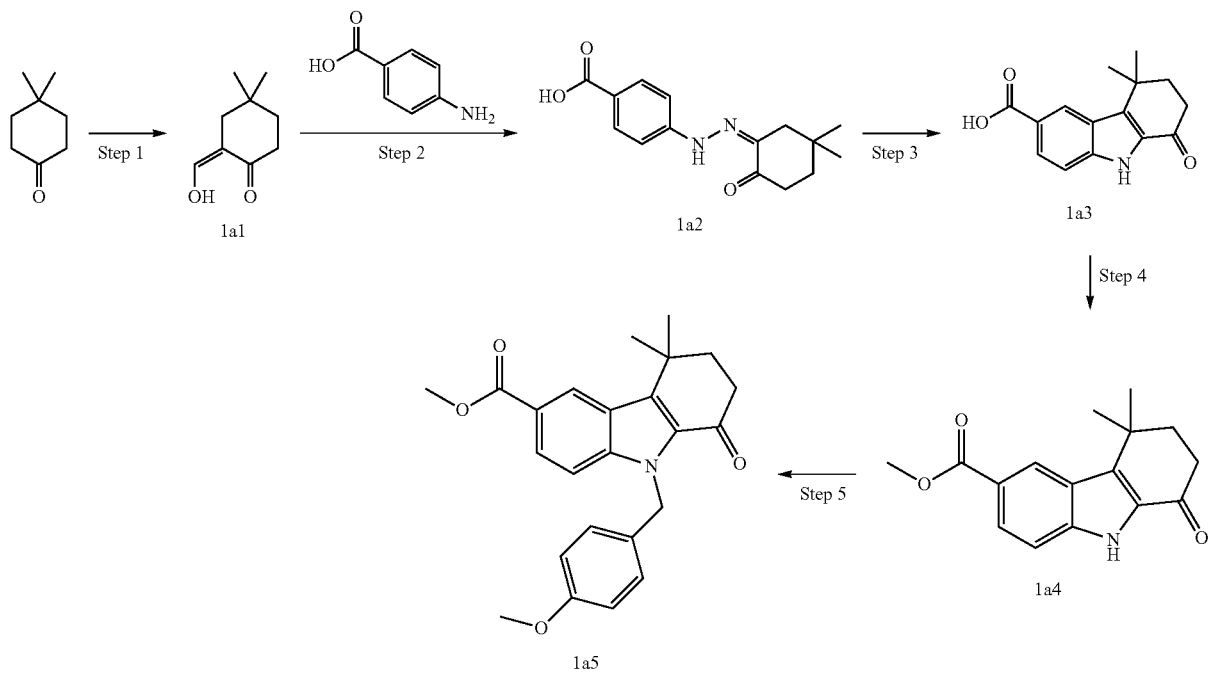

Step 5:

To 1a4 (2.10 g, 7.74 mmol) in DMF (20 mL), is added NaH (60% in oil, 350 mg, 8.75 mmol). After 5 min, 4-methoxybenzyl chloride (1.16 mL, 8.55 mmol) is added and the resulting solution is stirred at RT overnight. The reaction mixture is diluted with EtOAc, then washed with an aqueous solution of saturated $NaHCO_3$, $H_2O$ (2×) and brine, dried over $MgSO_4$, concentrated and purified by Combiflash (90:10 Hex/EtOAc) to afford 1a5.

Example 2

Preparation of Intermediate 2a4

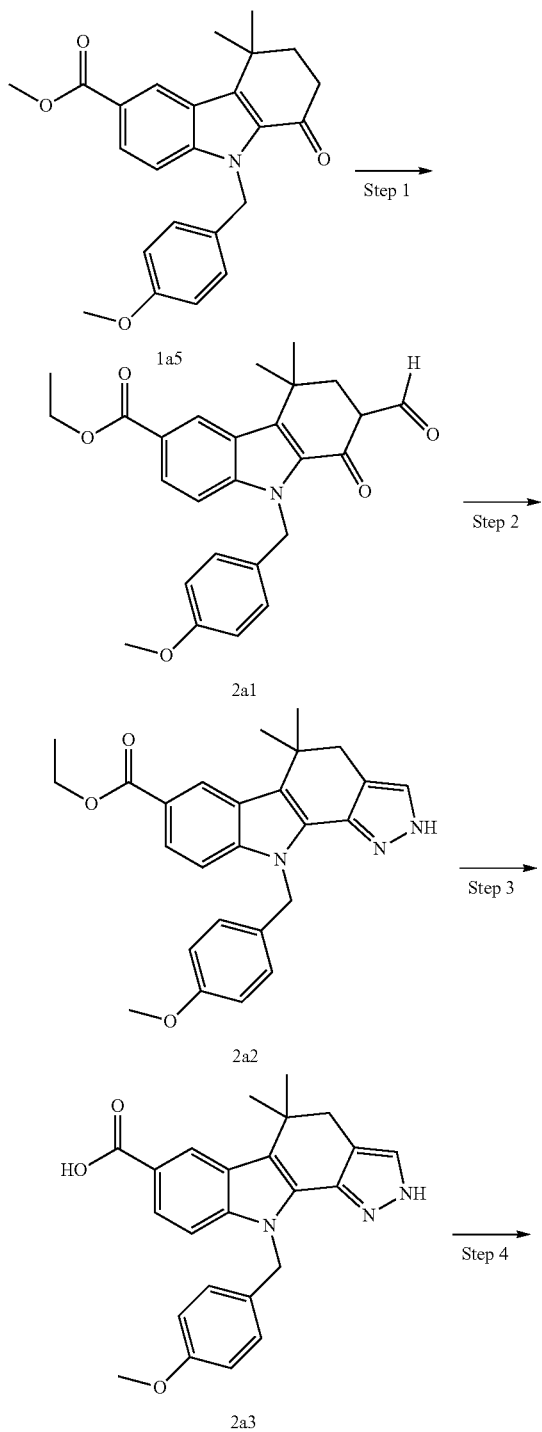

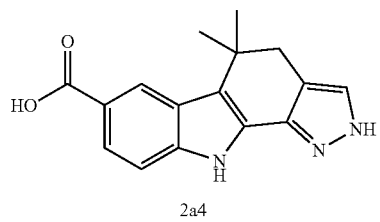 [SMILES: CC1(C)Cc2c[nH]nc2-c2[nH]c3ccc(C(=O)O)cc3c21]

Step 1:

To 1a5 (1.00 g, 2.56 mmol) and ethyl formate (500 μL, 6.22 mmol) in THF (15 mL) is added NaH (60% in oil, 306.5 mg, 7.66 mmol) at 0° C. This mixture is stirred for 10 min, warmed to RT, and then stirred for 2 h. EtOAc and 1M HCl are added. The layers are separated and the organic layer is washed with water and brine, dried with $Na_2SO_4$ and concentrated to provide 2a1.

Step 2:

To a solution of 2a1 (250 mg, 0.58 mmol) in DMF (2.0 mL) and EtOH (3.0 mL) is added 2M hydrazine in THF (2.0 mL). The mixture is heated to 90° C. and stirred for 1 h. EtOAc and 1M HCl are added. The layers are separated and the organic layer is washed with water and brine, dried with $Na_2SO_4$ and concentrated to provide crude 2a2 that is used as such.

Step 3:

The crude 2a2 obtained in step 2 is dissolved in DMF (3.0 mL) and 1M NaOH (2.0 mL, 2.00 mmol) is added. The mixture is stirred for 16 h. EtOAc and 1M HCl are added. The layers are separated and the organic layer is washed with water and brine, dried with $Na_2SO_4$ and concentrated to provide crude 2a3 that is used as such.

Step 4:

The crude 2a3 obtained in step 3 is dissolved in TFA (2.0 mL) and triflic anhydride (30 μl) is added. The mixture is stirred for 2 h, concentrated to dryness and purified by Combiflash (0:100 to 5:95, MeOH/DCM) to provide 2a4.

Example 3

Preparation of Intermediate 3a12

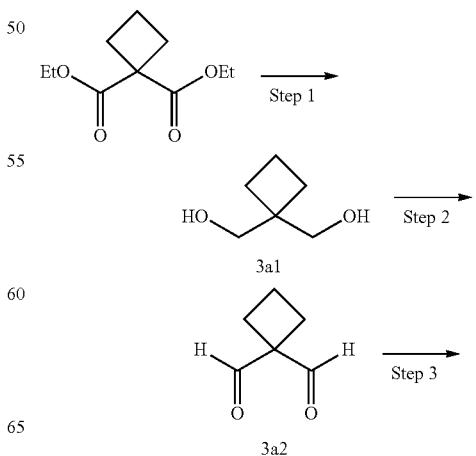

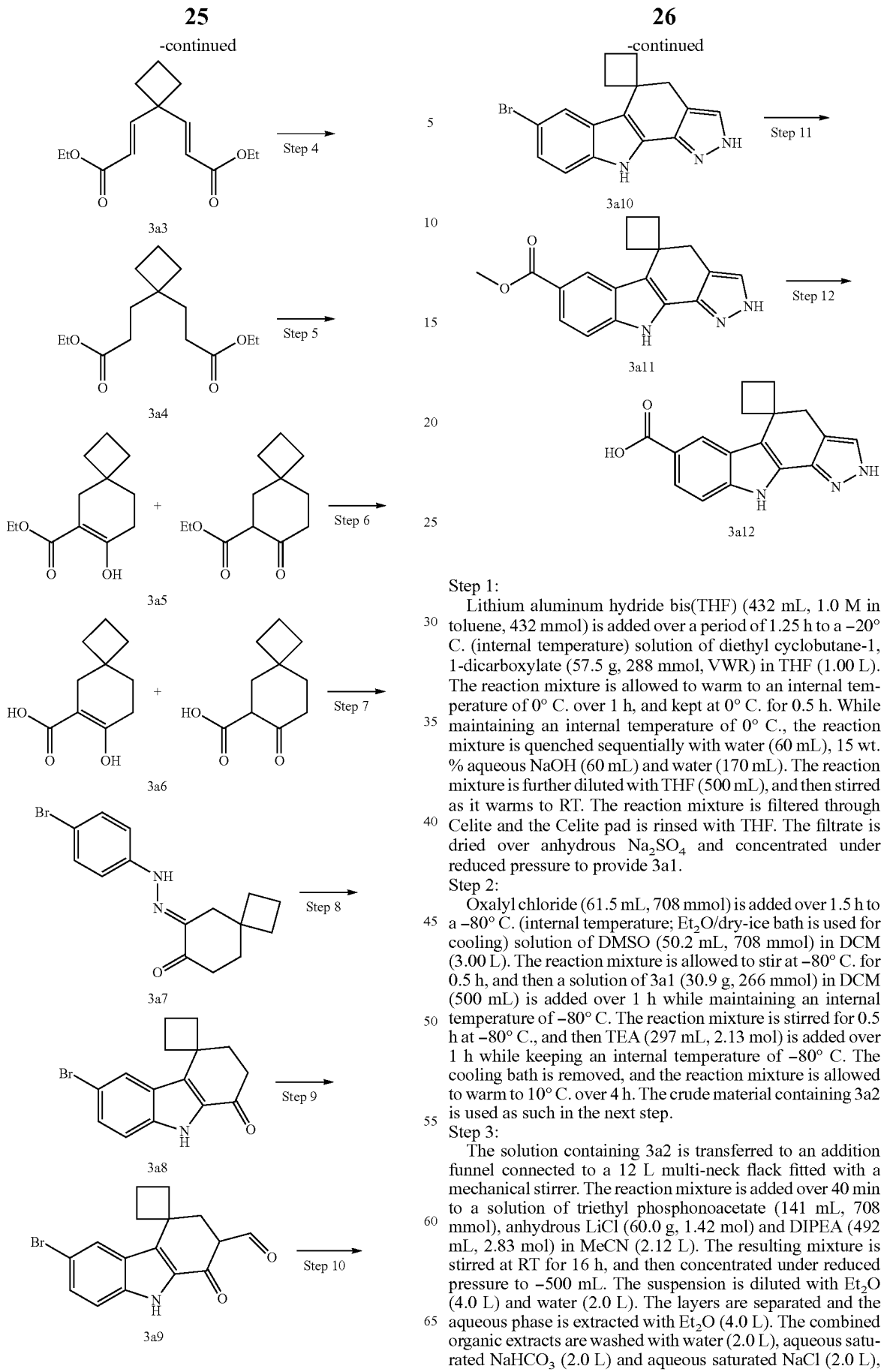

Step 1:
Lithium aluminum hydride bis(THF) (432 mL, 1.0 M in toluene, 432 mmol) is added over a period of 1.25 h to a −20° C. (internal temperature) solution of diethyl cyclobutane-1,1-dicarboxylate (57.5 g, 288 mmol, VWR) in THF (1.00 L). The reaction mixture is allowed to warm to an internal temperature of 0° C. over 1 h, and kept at 0° C. for 0.5 h. While maintaining an internal temperature of 0° C., the reaction mixture is quenched sequentially with water (60 mL), 15 wt. % aqueous NaOH (60 mL) and water (170 mL). The reaction mixture is further diluted with THF (500 mL), and then stirred as it warms to RT. The reaction mixture is filtered through Celite and the Celite pad is rinsed with THF. The filtrate is dried over anhydrous $Na_2SO_4$ and concentrated under reduced pressure to provide 3a1.

Step 2:
Oxalyl chloride (61.5 mL, 708 mmol) is added over 1.5 h to a −80° C. (internal temperature; $Et_2O$/dry-ice bath is used for cooling) solution of DMSO (50.2 mL, 708 mmol) in DCM (3.00 L). The reaction mixture is allowed to stir at −80° C. for 0.5 h, and then a solution of 3a1 (30.9 g, 266 mmol) in DCM (500 mL) is added over 1 h while maintaining an internal temperature of −80° C. The reaction mixture is stirred for 0.5 h at −80° C., and then TEA (297 mL, 2.13 mol) is added over 1 h while keeping an internal temperature of −80° C. The cooling bath is removed, and the reaction mixture is allowed to warm to 10° C. over 4 h. The crude material containing 3a2 is used as such in the next step.

Step 3:
The solution containing 3a2 is transferred to an addition funnel connected to a 12 L multi-neck flack fitted with a mechanical stirrer. The reaction mixture is added over 40 min to a solution of triethyl phosphonoacetate (141 mL, 708 mmol), anhydrous LiCl (60.0 g, 1.42 mol) and DIPEA (492 mL, 2.83 mol) in MeCN (2.12 L). The resulting mixture is stirred at RT for 16 h, and then concentrated under reduced pressure to ~500 mL. The suspension is diluted with $Et_2O$ (4.0 L) and water (2.0 L). The layers are separated and the aqueous phase is extracted with $Et_2O$ (4.0 L). The combined organic extracts are washed with water (2.0 L), aqueous saturated $NaHCO_3$ (2.0 L) and aqueous saturated NaCl (2.0 L), dried over anhydrous Na₂SO₄, filtered, concentrated under reduced pressure and purified by Combiflash (5% EtOAc/Hex) to provide 3a3.

Step 4:

Palladium on activated carbon (22.5 g, 10 wt. %, wet, Degussa type E101 NE/W, 10.6 mmol, Strem) is added to a solution of 3a3 (53.3 g, 212 mmol) in EtOAc (2.10 L). The suspension is divided approximately equally between two 2 L round-bottom flasks, and each flask is capped with an airfree adapter fitted with a large balloon filled with hydrogen gas. The systems are purged with hydrogen gas (3×), and then allowed to stir under a hydrogen atmosphere for 2 days. The reaction mixtures are filtered through Celite with EtOAc washings (3×100 mL). The filtrate is concentrated under reduced and purified by Combiflash (5% EtOAc/Hex) to provide 3a4.

Step 5:

Potassium tert-butoxide (39.0 g, 347 mmol) is added to a solution of 3a4 (44.5 g, 174 mmol) in THF (1.75 L). The resulting mixture is heated to reflux, and then stirred at reflux for 1 h. The reaction mixture is cooled to an internal temperature of −10° C., quenched with aqueous 1M HCl (700 mL), and then allowed to warm to RT. The solution is diluted with Et₂O (4.0 L) and the layers are separated. The organic layer is washed with aqueous saturated NaCl (700 mL), dried over anhydrous Na₂SO₄, filtered, concentrated under reduced pressure and purified by Combiflash (2.5% EtOAc/Hex) to provide 3a5.

Step 6:

3a5 (750 mg, 3.58 mmol) is charged in a round bottom flask with water (10 mL) and 5N NaOH (0.78 mL, 3.92 mmol) and the resulting mixture is stirred for 24 h. The reaction mixture is transferred to a separatory funnel and washed with ether (2×). The aqueous layer is transferred back to its original flask, cooled to 0° C. and quenched with 1 equivalent of 6N HCl (until pH is approximately 4-5). The mixture is stirred at 0° C. for 25 min to afford 3a6 which is used as such in the next step.

Step 7:

To the aqueous solution of 3a6 (619 mg, 3.40 mmol) at 0° C. is added over 20 min a solution of 4-bromobenzenediazonium tetrafluoroborate (920 mg, 3.40 mmol) in water (12 mL). The resulting mixture is stirred at 0° C. for 10 min, and then allowed to stir at RT for 30 min. The reaction mixture is filtered and the residue is dissolved in EtOAc, washed with brine, dried over MgSO₄, filtered and concentrated under reduced pressure to provide 3a7, which is used as such in the next step.

Step 8:

3a7 (1.09 g, 3.40 mmol) is suspended in MeCN (27 mL) and an aqueous solution of sulfuric acid (1.8M, 5.7 mL, 10.2 mmol) is added. The reaction mixture is stirred for 4 h at 80° C., then cooled to RT and concentrated under reduced pressure to remove approximately half of the MeCN. Water (50 mL) is added, and the mixture is stirred for 1 h. The mixture is filtered and the residue is purified by Combiflash (100% Chloroform, then Chloroform/MeOH 95%/5%) to give 3a8.

Step 9:

To 3a8 (1.00 g, 3.29 mmol) and ethyl formate (0.645 mL, 8.02 mmol) in THF (25.00 mL) is added NaH (60% in oil, 420.8 mg, 10.52 mmol) at 0° C. This mixture is stirred for 10 min at 0° C., warmed to RT and stirred for 2 h. EtOAc and 1N HCl are added. The layers are separated and the organic layer is washed with water and brine, dried over MgSO₄, filtered and concentrated to give 3a9.

Step 10:

3a9 (1.09 g, 3.28 mmol) is dissolved in EtOH (15.00 mL) and hydrazine hydrate (3.00 mL, 96.47 mmol) is added. The reaction mixture is stirred at 90° C. for 2 h. EtOAc and 1N HCl (aqueous) are added. The layers are separated and the organic layer is washed with water and brine, dried over MgSO₄, filtered and concentrated under vacuum. The crude material is purified by Combiflash (DCM/MeOH) to provide 3a10.

Step 11:

To 3a10 (995.0 mg, 3.03 mmol) in DMSO (30.00 mL) and MeOH (15.00 mL) is added TEA (2.22 mL, 15.95 mmol), followed by Pd(dppf)Cl₂ DCM adduct (287.5 mg, 0.35 mmol). The resulting solution is purged with CO(g) and heated at 85° C. under 1 atmosphere of CO(g) for 8 h. The solution is cooled to RT and diluted with DCM. The organic phase is washed with water (3×), washed with brine, dried over MgSO₄, filtered and concentrated under reduced pressure. The crude material is purified by Combiflash (DCM/MeOH) to provide 3a11.

Step 12:

3a11 (583 mg, 1.90 mmol) is dissolved in DMSO (35.00 mL) and cooled to 0° C. 1N NaOH (aqueous) (7.60 mL, 7.60 mmol) is added to the solution. The mixture is warmed to 45° C. and stirred for 3 h. The mixture is quenched with 1N HCl (aqueous) and extracted with EtOAc. The organic layers are combined, washed with brine (2×), dried over MgSO₄, filtered and concentrated under reduced pressure to provide 3a12 which is used as is in subsequent reactions.

Example 4

Preparation of Intermediates 4a8

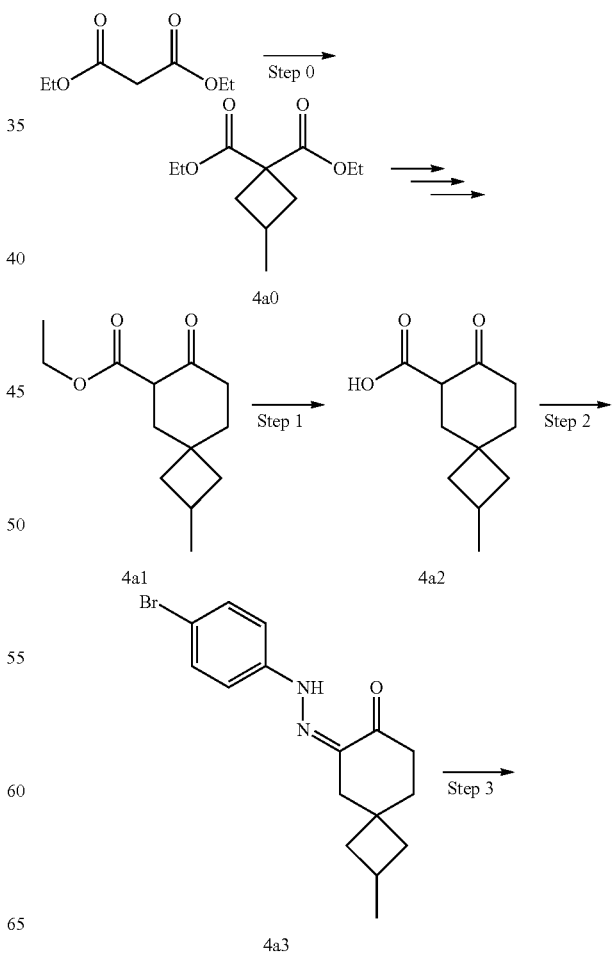

-continued

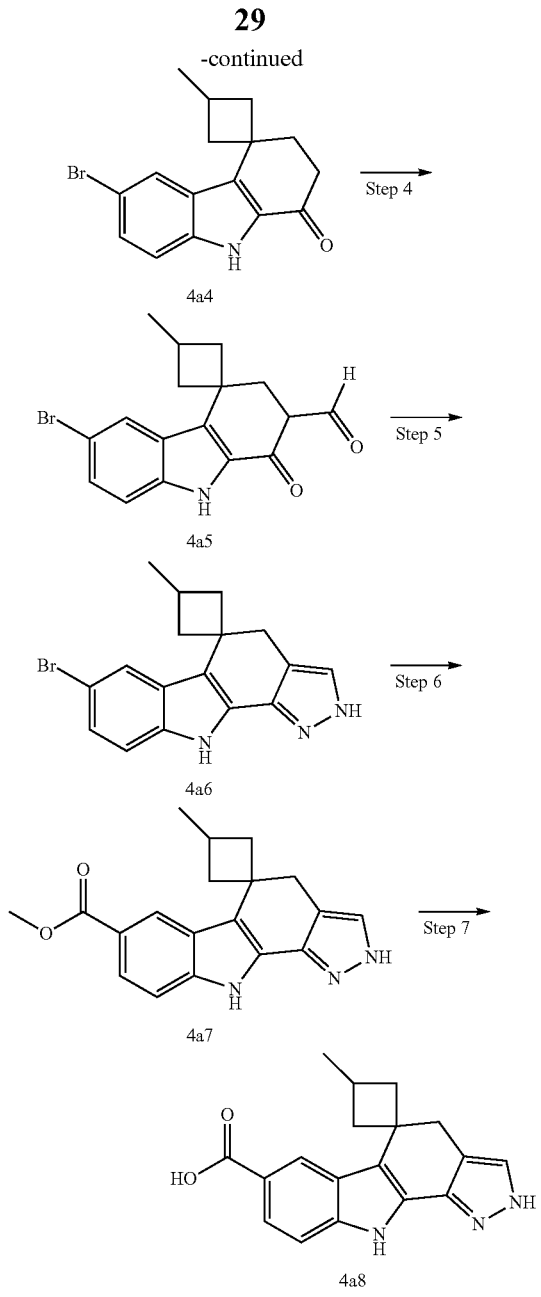

Step 0:

1-bromo-3-chloro-2-methylpropane (88.1 g, 514 mmol) is added to diethyl malonate (82.4 g, 514 mmol, Aldrich). This mixture is heated to 80° C., and sodium ethoxide in EtOH (21 wt %, 383 mL, 1.03 mol) is added. The resulting solution is stirred at 80-85° C. for 14 h, and then cooled to RT. The solvent is removed in vacuo. The residue is cooled to 0° C., neutralized with 2N HCl and extracted with diethyl ether (3×200 mL). The combined organic extracts are washed with water and a saturated aqueous solution of NaHCO$_3$ and dried over anhydrous Na$_2$SO$_4$. The solvent is vacuum distilled to provide 4a0.

Compound 4a1 is prepared from 4a0 using a procedure analogous to that described in Example 3, Steps 1 to 5.

Step 1:

Compound 4a1 (4.00 g, 17.83 mmol) is charged in a round bottom flask with water (50.00 mL) and 5N NaOH (aqueous, 3.92 L 19.62 mmol), and the resulting mixture is stirred for 24 h. The reaction is transferred to a separatory funnel, and washed with ether (2×). The aqueous layer is transferred back to the original flask, cooled to 0° C. and quenched with 1 equivalent of HCl (aqueous) until the pH is slightly acidic (4-5). The mixture is stirred at 0° C. for 25 min to afford 4a2 which is used as such in the next step.

Step 2:

To a solution of 4a2 (3.50 g, 17.83 mmol) in water (80 mL) at 0° C. is added a solution of 4-bromobenzenediazonium tetrafluoroborate (4.83 g, 17.83 mmol) in water (80 mL) over a period of 15-20 min. The resulting mixture is stirred at 0° C. for 10 min, and then allowed to stir at RT for 30 min. The reaction mixture is filtered and the residue is washed with water. The residue is dissolved in EtOAc, washed with brine, dried over MgSO$_4$, filtered and concentrated under reduced pressure to provide 4a3.

Step 3:

4a3 (5.97 g, 17.81 mmol) is suspended in MeCN (100.0 mL) and an aqueous solution of 1.8M sulfuric acid (30.00 mL, 540.00 mmol) is added. The reaction mixture is stirred for 4 h at 80° C. The reaction mixture is cooled to RT, extracted with EtOAc, washed with saturated ammonium bicarbonate (2×), washed with brine, dried over MgSO$_4$, filtered and concentrated under reduced pressure. The residue is triturated with ether for 1 h, and then filtered. The residue is purified by Combiflash (Chloroform/MeOH) to provide 4a4.

Step 4:

4a4 (1.00 g, 3.14 mmol) and ethyl formate (0.616 mL, 8.02 mmol) in THF (30.00 mL) is added to NaH (60% in oil, 402.25 mg, 10.06 mmol) at 0° C. The reaction mixture is stirred for 10 min at 0° C., warmed to RT and stirred for 2 h. EtOAc and 1N HCl are added and the phases are separated. The organic layer is washed with water and brine, dried over MgSO$_4$, filtered and concentrated to give 4a5.

Step 5:

4a5 (1.09 g, 3.14 mmol) is dissolved in EtOH (30.00 mL) and hydrazine hydrate (6.00 mL, 192.64 mmol) is added. The reaction mixture is stirred at 90° C. for 2 h. EtOAc and 1N HCl are added and the phases are separated. The organic layer is washed with water and brine, dried over MgSO$_4$, filtered, concentrated under vacuum and purified by Combiflash (DCM/MeOH) to provide 4a6.

Step 6:

To a solution of 4a6 (1.07 g, 3.13 mmol) in DMSO (30.00 mL) and MeOH (15.00 mL) is added TEA (2.29 mL, 16.45 mmol), followed by Pd(dppf)Cl$_2$ DCM adduct (296.4 mg, 0.36 mmol). The resulting solution is purged with CO(g) and heated at 85° C. under 1 atmosphere of CO(g) for 8 h. The solution is cooled to RT and diluted with DCM. The organic phase is washed with water (3×), washed with brine, dried over MgSO$_4$, filtered, concentrated under reduced pressure and purified by Combiflash (DCM/MeOH) to provide 4a7.

Step 7:

4a7 (110 mg, 0.34 mmol) is dissolved in DMSO (4.50 mL) and cooled to 0° C. 1N NaOH (1.37 mL, 1.37 mmol) is added to the solution. The mixture is warmed to 45° C. and stirred for 3 h. The mixture is quenched with 1N HCl and extracted with EtOAc. The organic layers are combined, washed with brine (2×), dried over MgSO$_4$ and concentrated under reduced pressure to provide 4a8 which is used as is in subsequent reactions.

Example 5

Preparation of Compound 2008

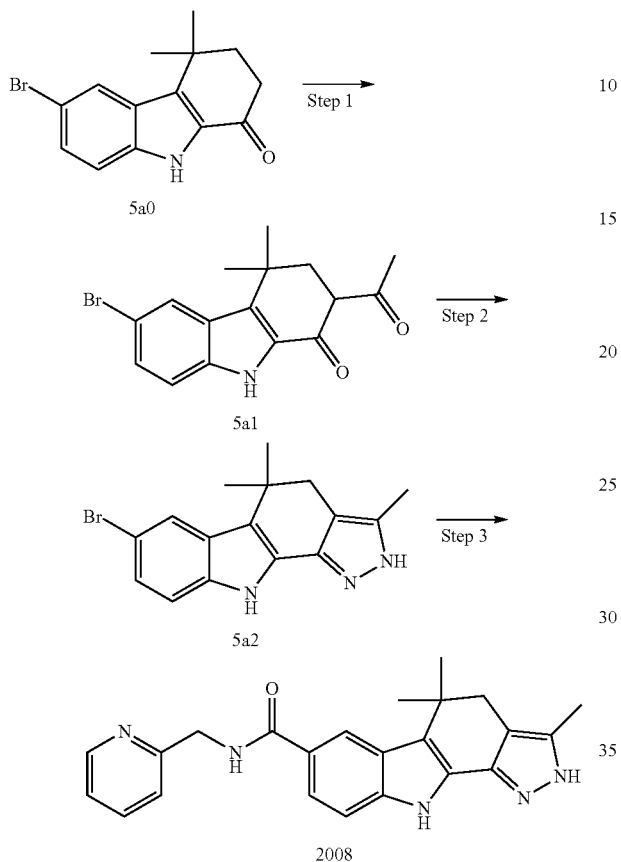

5a0 is made analogously to the procedure described in Example 1, Step 1-3 using 4-bromo-aniline as the partner in Step 2.

Step 1:

To a solution of 5a0 (100.0 mg, 0.34 mmol) in THF (3.00 mL) is added acetic anhydride (49 µL, 0.52 mmol). The reaction mixture is cooled to 0° C. and 1.0M LiHMDS in THF (2.05 mL, 2.05 mmol) is added. The reaction mixture is allowed to reach RT, and is then stirred for 1 h. The reaction mixture is warmed to RT, and then 3 more equivalents of 1.0M LiHMDS in THF is added. The reaction mixture is stirred for 2 h, diluted with EtOAc, quenched with 1N HCl, extracted and the layers are separated. The aqueous layer is extracted with EtOAc (2×). The organic layers are combined, washed with brine (2×), dried over MgSO$_4$, filtered, concentrated under reduced pressure and purified by Combiflash (Hex/EtOAc) to provide 5a1.

Step 2:

5a1 (28.9 mg, 0.086 mmol) is dissolved in EtOH (4.5 mL) and hydrazine hydrate (1.00 mL, 32.11 mmol) is added. The reaction mixture is stirred at 90° C. for 2 h. EtOAc and 1N HCl are added, and the layers are separated. The organic layer is washed with water and brine, dried over MgSO$_4$, filtered, concentrated under reduced pressure and purified by Combiflash (Hex/EtOAc) to provide 5a2.

Step 3:

To a solution of 5a2 (23.6 mg, 0.071 mmol) in DMF (4.00 mL) is added TEA (199.2 µL, 1.43 mmol), and 2-(aminomethyl)pyridine (36.8 µL, 0.357 mmol). The mixture is degassed with argon for 5 min, then Pd(dppf)Cl$_2$ DCM adduct (11.7 mg, 0.014 mmol) is added. The reaction mixture is bubbled with CO(g) for 5 min. The reaction mixture is kept under a CO(g) atmosphere (balloon), and heated to 85° C. for 18 h. The reaction mixture is cooled to RT, and then EtOAc is added. The mixture is washed with water, washed with brine (2×), dried over MgSO$_4$, filtered, concentrated under reduced pressure and purified by preparative RP-HPLC to provide 2008.

Example 6

Preparation of Intermediate 6a2

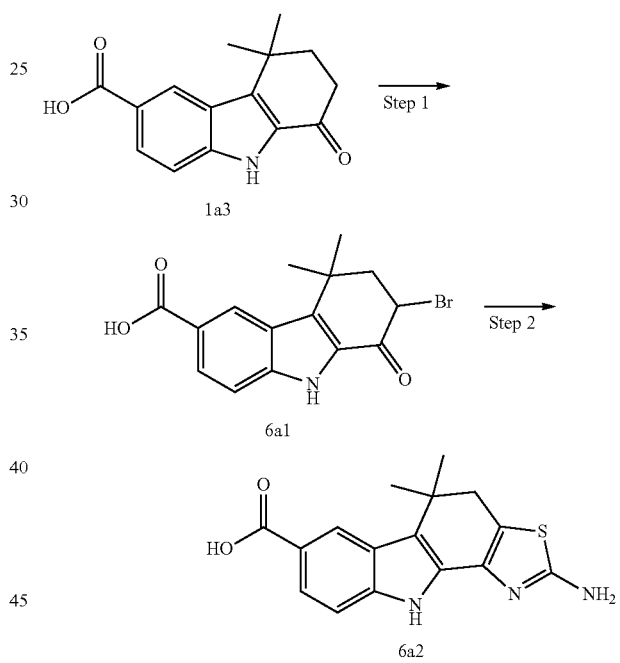

Step 1:

A mixture of 1a3 (100.0 mg, 0.39 mmol) and cupric bromide (173.6 mg, 0.78 mmol) in EtOAc (3.00 mL) is stirred for 10 h at reflux under a nitrogen atmosphere. The reaction mixture is cooled to RT and filtered. The organic layer is transferred to a separatory funnel and washed with brine, dried over MgSO$_4$, filtered and concentrated under reduced pressure to provide 6a1 which is taken to the next step as is.

Step 2: To a solution of 6a1 (125.0 mg, 0.37 mmol) in DMF (10.00 mL) is added thiourea (292.3 mg, 3.84 mmol). The reaction mixture is stirred at 90° C. for 3 h, then cooled to RT and diluted with EtOAc. The mixture is washed with water (2×), washed with brine (2×), dried over MgSO$_4$, filtered and concentrated under reduced pressure to afford 6a2 which is used as is in subsequent reactions.

Example 7
Preparation of Intermediate 7a1
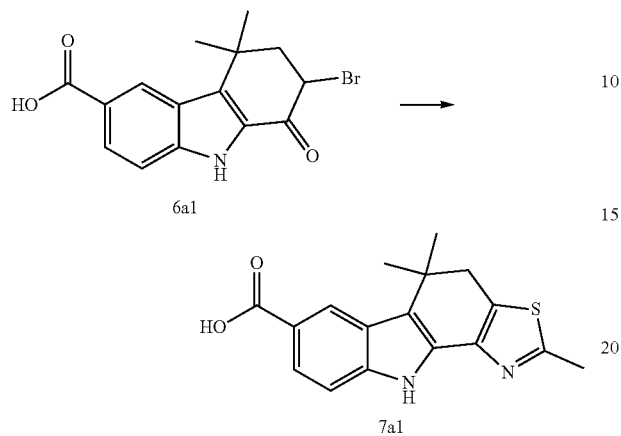
To a solution of 6a1 (125.0 mg, 0.37 mmol) in DMF (10.00 mL) is added thioacetamide (83.8 mg, 1.11 mmol). The reaction mixture is stirred at 90° C. for 16 h, then diluted with EtOAc. The mixture is washed with water (2×), washed with brine (2×), dried over $MgSO_4$, filtered and concentrated under reduced pressure to provide 7a1.
Example 8
Preparation of Intermediate 8a10
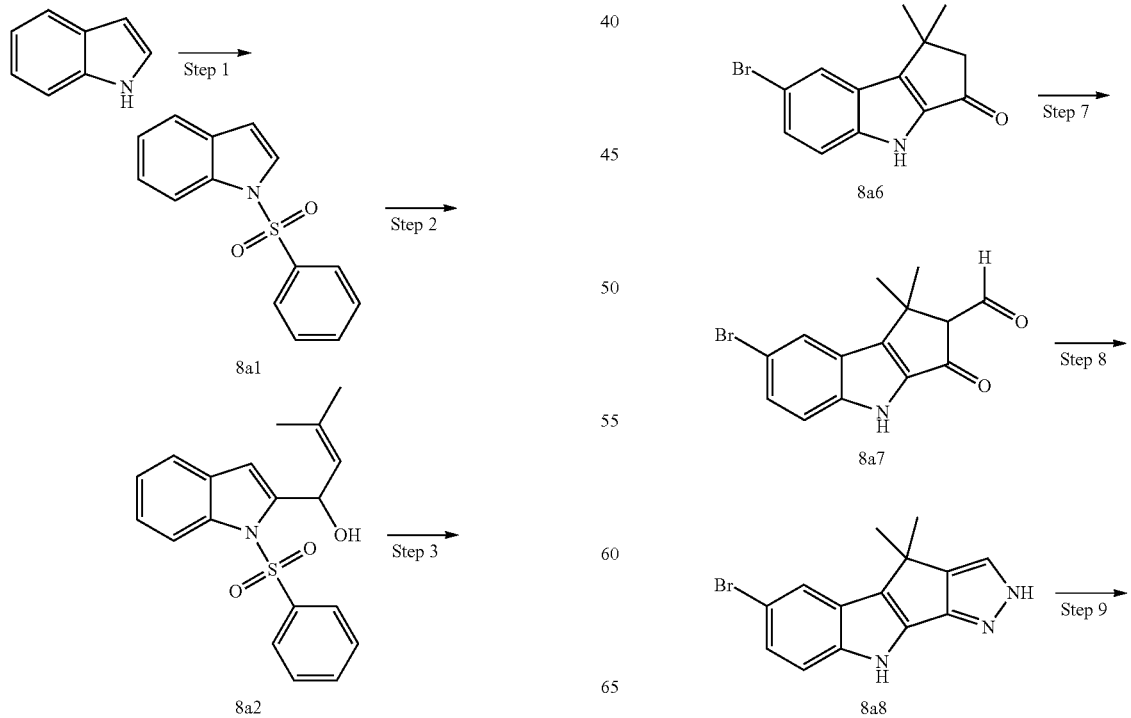
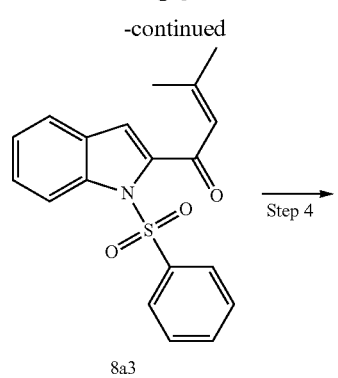
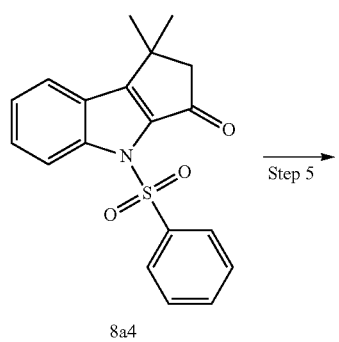
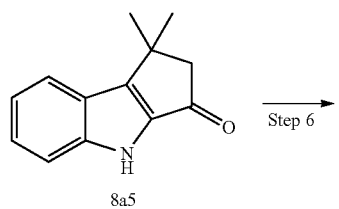
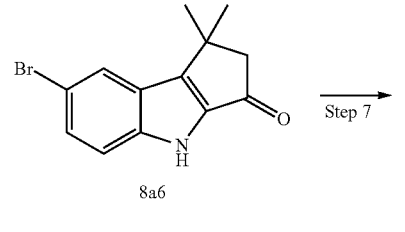
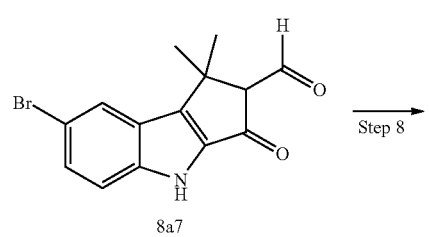
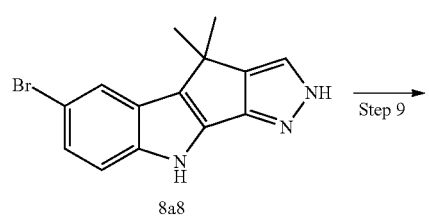

-continued

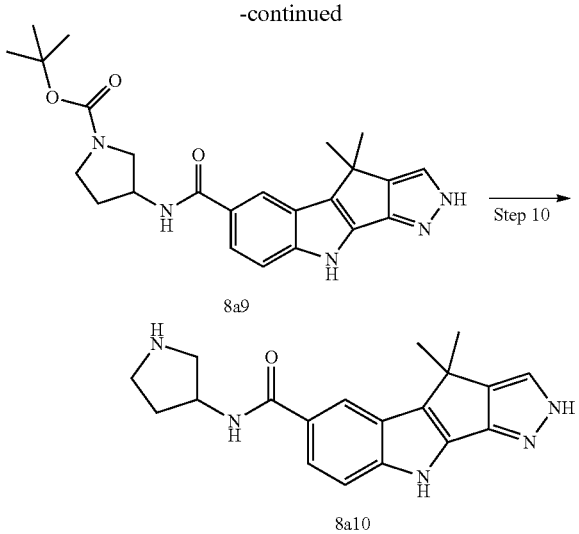

8a9

8a10

Step 1:

To a solution of indole (Aldrich, 50 g, 0.72 mol) in anhydrous THF (800 mL) is added NaH (60% in oil, 18.7 g, 0.47 mol) at 0° C. The reaction mixture is stirred at this temperature for 30 min, and then benzenesulfonyl chloride (82.9 g, 0.47 mol) is added. The reaction mixture is allowed to warm to RT and is stirred at RT overnight. The reaction mixture is quenched with water (100 mL), then extracted with EtOAc (2×), washed with brine, dried ($Na_2SO_4$) and concentrated. Purification by Combiflash (5%-10% EtOAc/Hex) affords 8a1.

Step 2:

To a solution of 8a1 (52.1 g, 0.20 mol) in anhydrous THF (1.5 L) at −78° C. is added a solution of t-BuLi (1.7M in pentane, 157 mL). The resulting solution is stirred at −78° C. for 1 h and then a solution of 3-methyl-2-butenal (25.4 mL) in anhydrous THF (350 mL) is added over a period of 30 min. The reaction mixture is stirred at −78° C. for 45 min. After warming to RT, the reaction mixture is quenched by saturated $NH_4Cl$ (∼1.5 L), and extracted with EtOAc. The combined organic layers are washed with brine, dried over $Na_2SO_4$ and concentrated in vacuo to provide crude 8a2 that is used as such.

Step 3:

To a solution of the crude 8a2 obtained in step 2 in DCM anhydrous (2 L) at RT is added 4-methyl morpholine N-oxide (35.5 g, 0.30 mol) and 4 Å molecular sieves powder (59 g). After 20 min, TPAP (3.5 g, 0.01 mol) is added and the reaction mixture is stirred at RT overnight. The reaction mixture is filtered through a Celite pad with DCM washings. The filtrate is concentrated and purified by Combiflash (DCM/Hex) to provide 8a3.

Step 4:

To a solution of 8a3 (9.1 g, 26.81 mmol) in toluene anhydrous (300 mL) is added $BF_3.OEt_2$. The resulting mixture is heated to 120° C. and stirred at this temperature overnight. The reaction mixture is diluted with EtOAc, washed with brine, dried over $Na_2SO_4$ and filtered though a Celite pad. The filtrate is concentrated and purified by Combiflash (EtOAc/Hex) to provide 8a4.

Step 5:

A 5M NaOH aqueous solution (80 mL) is added to 8a4 (6.7 g, 0.02 mol) in MeOH (670 mL). The reaction mixture is heated to 80° C. and is maintained at this temperature for 90 min. The reaction mixture is concentrated and the residue is treated with DCM and water. The aqueous phase is back-extracted. The combined organic phases are washed with water and brine, dried over $Na_2SO_4$, and concentrated to provide 8a5.

Step 6:

To a solution of 8a5 (3.7 g, 18.57 mmol) in anhydrous DCM (80 mL) at −78° C. over 20 min is added pyridine (4.51 mL, 55.71 mmol) and a solution of bromine (2.86 mL, 55.71 mmol) in DCM (5 mL). The mixture is stirred at −78° C. for 3 min, then stirred at RT under an argon atmosphere for 60 min. The reaction mixture is cooled to −78° C., then Zn (6.07 g, 92.85 mmol) and HAc/THF (5.3 mL, 95.85 mmol) are added. The mixture is warmed to RT over 45 min, then stirred at RT for 30 min. DCM (200 mL) is added, and then 0.5N HCl (300 mL) is added to the mixture. The aqueous layer is extracted (2×) and the combined organic layers are concentrated and purified by Combiflash (5%-20% EtOAc/Hex) to provide 8a6.

Step 7:

To 8a6 (500 mg, 1.80 mmol) and ethyl formate (234 μL, 2.92 mmol) in THF (10.00 mL) is added NaH (60% in oil, 153.0 mg, 3.83 mmol) at 0° C. The resulting mixture is stirred for 10 min at 0° C., warmed to RT and stirred for 2 h. EtOAc and 1N HCl are added and the phases are separated. The organic layer is washed with water and brine, dried over $MgSO_4$, filtered and concentrated under reduced pressure to give 8a7.

Step 8:

8a7 (365.0 mg, 1.19 mmol) is dissolved in EtOH (15.00 mL) and hydrazine hydrate (0.111 mL, 3.58 mmol) is added. The reaction mixture is stirred at 90° C. for 2 h. EtOAc and 1N HCl are added. The phases are separated, and the organic layer is washed with water and brine, dried over $MgSO_4$, filtered, concentrated under reduced pressure and purified by Combiflash (DCM/MeOH) to provide 8a8.

Step 9:

To a solution of 8a8 (70.0 mg, 0.23 mmol) in DMF (4.00 mL) is added TEA (645.8 μL, 4.63 mmol) and (+/−)-3-amino-1-N—BOC-pyrrolidine (215.7 mg, 1.16 mmol, Chembridge). The mixture is degassed with Argon for 5 min, then Pd(dppf)$Cl_2$ DCM adduct (37.8 mg, 0.046 mmol) is added. The reaction mixture is bubbled with CO(g) for 5 min. The reaction mixture is kept under a CO(g) atmosphere (balloon), and heated to 85° C. for 18 h. The reaction mixture is cooled to RT, and then EtOAc is added. The mixture is washed with water, washed with brine (2×), dried over $MgSO_4$, filtered, concentrated under reduced pressure and purified by Combiflash (DCM/MeOH) to provide 8a9.

Step 10:

8a9 (48.8 mg, 0.11 mmol) is dissolved in DCM (1.00 mL) and TFA (0.50 mL, 6.49 mmol) is added. The reaction mixture is stirred at RT for 1 h, and then concentrated under reduced pressure, azeotroped twice with MeOH and dried under high vacuum for 1 h to afford 8a10 which is used as is in subsequent reactions.

Example 9

Preparation of Intermediate 9a4

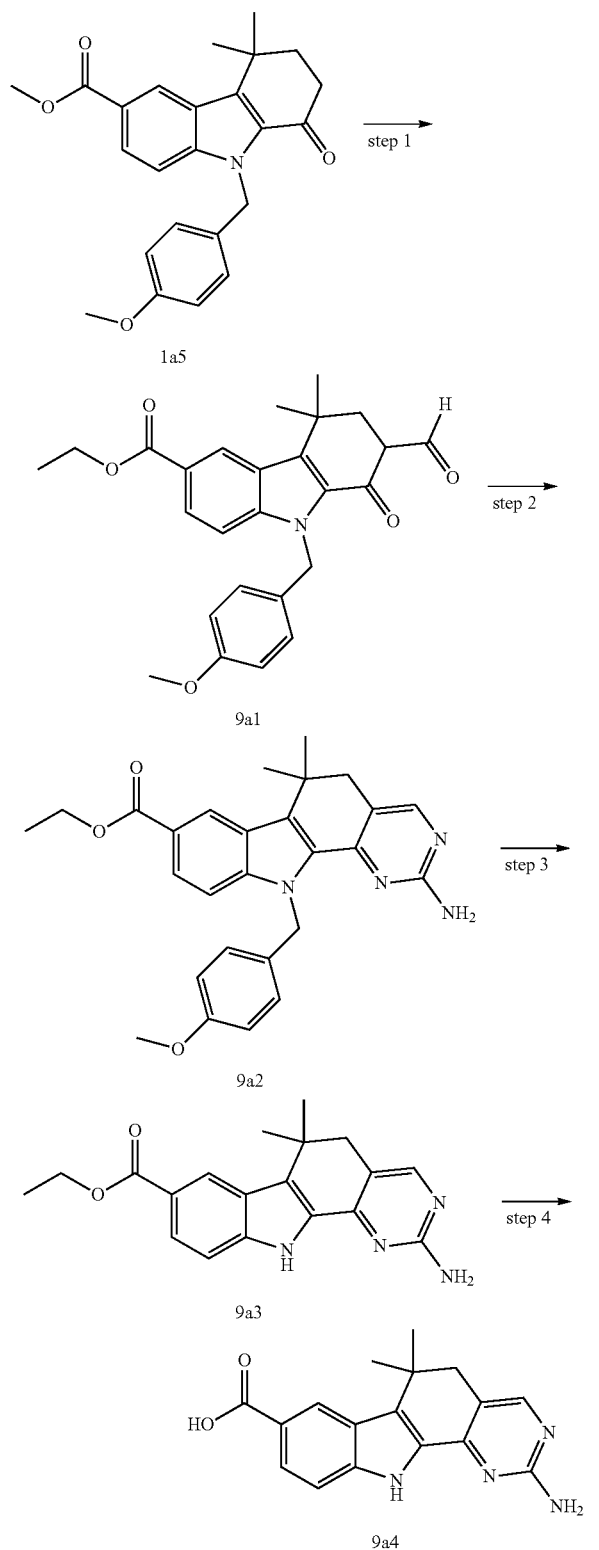

Step 1:
A solution of 1a5 (1.00 g, 2.55 mmol) in THF (15 mL) is cooled to 0° C. and then ethyl formate (0.5 mL, 6.15 mmol) is added followed by the addition of NaH (60% in oil, 306 mg, 7.65 mmol). The ice bath is removed and the resulting solution is stirred for 5 h at RT. The reaction mixture is diluted with EtOAc, and then washed with 1M HCl, water and brine. The organic layer is dried over $MgSO_4$, filtered and concentrated under reduced pressure. The residue is purified by Combiflash (90:10 Hex/EtOAc) to provide 9a1.

Step 2:
A mixture of 9a1 (555 mg, 1.28 mmol), guanidine hydrochloride (183 mg, 1.91 mmol) and sodium carbonate (170 mg, 1.60 mmol) in 3-pentanol (10 mL) is heated overnight at 100° C. The reaction mixture is diluted with EtOAc, and then washed with an aqueous solution of saturated $NaHCO_3$, water and brine. The organic layer is dried over $MgSO_4$, filtered and concentrated under reduced pressure. The residue is dried under vacuum to afford 9a2 which is used in the next step without any further purification.

Step 3:
A solution of 9a2 (584 mg, 1.28 mmol) in DCM (5 mL) is treated with TFA (2.5 mL). The resulting solution is stirred for 4 days at RT. The solvent is evaporated in vacuo and the residue is purified by Combiflash (EtOAc) to provide 9a3.

Step 4:
To a solution of 9a3 (116 mg, 0.34 mmol), in $THF:H_2O$ (2.5/1, 3.5 mL), and MeOH (1 mL) is added 1M NaOH (0.86 mL, 0.86 mmol). The reaction mixture is stirred overnight at RT and then is stirred for 3 h at 50° C. The solvents are removed in vacuo. The residue is dissolved in DMSO, filtered and purified by preparative RP-HPLC chromatography to provide 9a4.

Example 10

Preparation of Intermediate 10a3

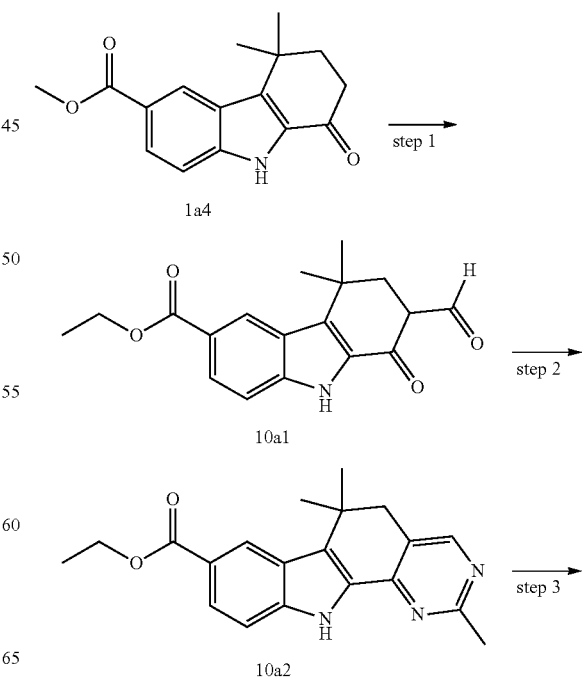

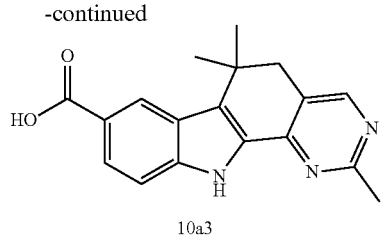

10a3

Step 1:

A solution of 1a4 (0.97 g, 3.57 mmol), in THF (15 mL) is cooled to 0° C., and then ethyl formate (0.73 mL, 8.98 mmol) is added, followed by the addition of NaH (60% in oil, 429 mg, 10.71 mmol). The ice bath is removed and the resulting solution is stirred for 5 h at RT. The reaction mixture is diluted with EtOAc, washed with 1M HCl, water and brine. The organic layer is dried over MgSO$_4$, filtered, concentrated under reduced pressure and purified by Combiflash (90:10 Hex/EtOAc) to provide 10a1.

Step 2:

A mixture of 10a1 (200 mg, 0.64 mmol), acetamidine hydrochloride (185 mg, 1.96 mmol) and sodium carbonate (172 mg, 1.62 mmol) in 3-pentanol (5 mL) is heated overnight at 100° C. The reaction mixture is diluted with EtOAc and washed with an aqueous solution of saturated NaHCO$_3$, water and brine. The organic layer is dried over MgSO$_4$, filtered and concentrated under reduced pressure. The residue is dried under vacuum to provide 10a2.

Step 3:

To a solution of compound 10a2 (214 mg, 0.63 mmol) in THF:H2O (2.5/1, 3.5 mL) and MeOH (3 mL) is added 1M NaOH (1.60 mL, 1.60 mmol). The reaction mixture is stirred for 36 h at RT. The solvents are removed in vacuo. The reaction mixture is diluted with 1M HCl and extracted with EtOAc (2×). The organic layer is dried over MgSO$_4$, filtered and concentrated under reduced pressure 10a3.

Example 11

Preparation of Intermediate 11a11

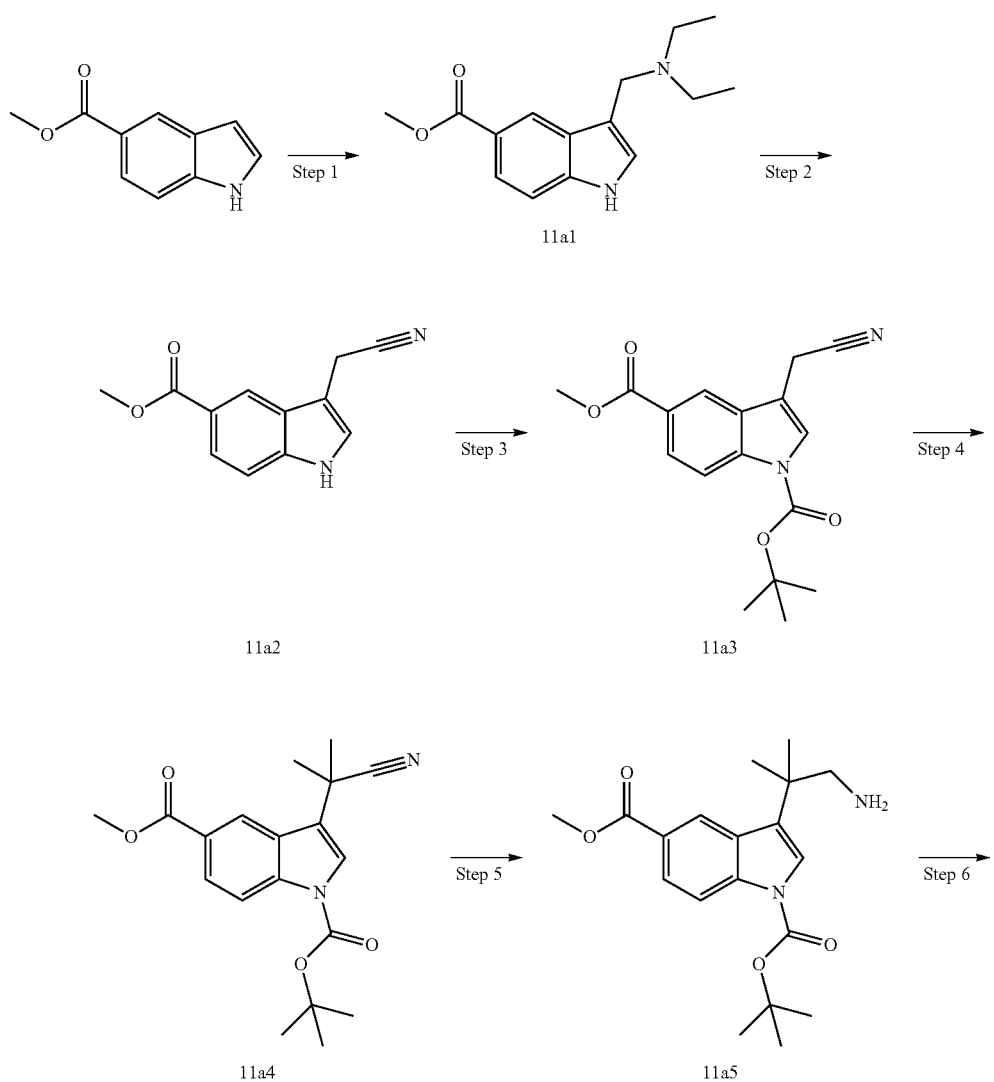

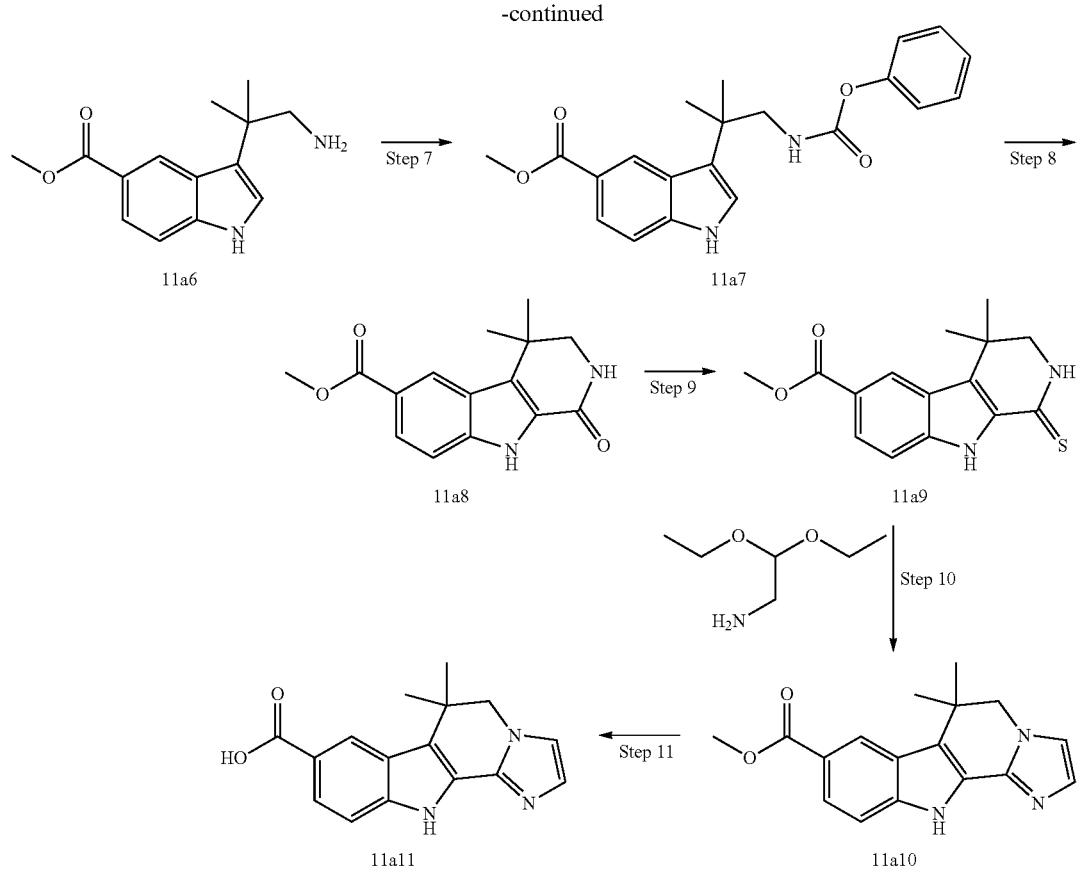

Step 1:
Diethylamine (17.9 mL, 171 mmol) is added to a stirred solution of acetic acid (20 mL, 356 mmol) at 0° C. Formaldehyde (37% in water, 12.6 mL, 171 mmol) and methyl indole-5-carboxylate (25 g, 142 mmol) are then added. The resulting mixture is stirred at RT for 2 h. The reaction mixture is partitioned between DCM and 10% NaOH solution (60 mL). The organic layer is separated, washed with water, dried with sodium sulphate and concentrated to dryness to afford 11a1.

Step 2:
11a1 (34 g, 130 mmol) is dissolved in THF (250 mL). Methyl iodide (9.8 mL, 156 mmol) is added at 0° C. and the resulting mixture is stirred overnight at RT. A solution of KCN (10.2 g, 156 mmol) in water (25 mL) is added, and then the reaction mixture is refluxed for 6 h. The solvent is removed under reduced pressure, and the residue is extracted with EtOAc. The extracts are washed with water then brine and dried over sodium sulphate. The organic layer is concentrated to provide 11a2.

Step 3:
A solution of 11a2 (18 g, 84 mmol) in DCM (180 mL) is treated with 4-(dimethylamino)pyridine (0.51 g, 4.2 mmol) and di-tert-butyldicarbonate (18.9 mL, 88 mmol). The mixture is stirred at RT for 2 h, and then concentrated to dryness to provide 11a3.

Step 4:
To a stirred solution of 11a3 (42 g, 133 mmol) and methyl iodide (24.9 mL, 400 mmol) in a mixture of DMF (420 mL) and THF (270 mL) is added NaH (60% in oil, 13.4 g, 334 mmol) over a period of 30 min at 0° C. The resulting mixture is stirred at RT for 2 h. The mixture is poured into 0.5N HCl (cold, 900 mL), and then further diluted with water (500 mL). The aqueous layer is extracted with EtOAc and the organic layer is washed with water, brine and dried over Na$_2$SO$_4$. The solvent is evaporated under reduced pressure to provide 11a4.

Step 5:
Platinum oxide (4 g, 16.8 mmol) is added to a stirred solution of 11a4 (15 g, 43 mmol) in a mixture of chloroform (18 mL), THF (93 mL) and MeOH (280 mL). The reaction mixture is maintained at 60 psi of hydrogen under a Parr-hydrogen apparatus for 16 h. The reaction mixture is filtered through Celite and concentrated. The residue is treated with a 0.5N NaOH solution and extracted with DCM. The organic layer is washed with water and brine, dried over Na$_2$SO$_4$ and concentrated to provide 11a5.

Step 6:
TFA (60 mL) is added at 0° C. to a stirred solution of 11a5 (15 g, 43 mmol) in DCM (120 mL). The resulting mixture is stirred at RT overnight. The reaction mixture is concentrated and 10% KOH (aqueous) is added until the pH is basic. The reaction mixture is then extracted with EtOAc and the organic layer is dried over sodium sulphate and concentrated to dryness to provide 11a6.

Step 7:
TEA (7.9 mL, 56 mmol) is added to a stirred solution of 11a6 (10 g, 40 mmol) in DCM. This solution is cooled to 0° C. and phenyl chloroformate (5.65 mL, 44 mmol) is added. The resulting mixture is stirred at RT for 1 h. The reaction mixture is diluted with DCM and quenched with 1N HCl. The layers are separated and the organic layer is washed with water, dried over Na$_2$SO$_4$ and concentrated to provide 11a7.

43

Step 8:

Boron trifluoride etherate (3.4 mL, 26 mmol) is added to a stirred solution of 11a7 (8.5 g, 23 mmol) in toluene (150 mL). The reaction mixture is refluxed for 3 h then allowed to cool to RT. Water (200 mL) and a saturated NaHCO$_3$ (aqueous) solution (200 mL) are added to the reaction. The resulting mixture is stirred at RT for 1 hr. The resulting solid is filtered and dried under vacuum to provide 11a8.

Step 9:

A mixture of 11a8 (1.0 g, 3.7 mmol) and phosphorus pentasulfide (1.6 g, 3.7 mmol) in anhydrous pyridine (10 mL) is refluxed overnight. The solvent is removed in vacuo and the residual material is triturated twice with a mixture of MeOH and MeCN to provide 11a9.

Step 10:

A mixture of 11a9 (250.0 mg, 0.87 mmol), aminoacetaldehyde diethylacetal (138.1 µL, 0.95 mmol) and p-toluenesulfonic acid (181.4 mg, 0.95 mmol) in butanol (10 mL) is heated under reflux for overnight. p-toluenesulfonic acid (181.4 mg, 0.95 mmol) is added to the mixture which is then heated under reflux for 2 days. The butanol is evaporated (azeotrope with Hex) and ice water (100 mL) is added. The solution is basified with 1N NaOH, then extracted with EtOAc, dried over MgSO$_4$, filtered and concentrated. The crude mixture is purified by Combiflash (50% EtOAc/Hex to 100% EtOAc) to provide 11a10.

Step 11:

To a solution of 11a10 (39.0 mg, 0.13 mmol) in MeOH (1.0 mL) and THF (0.5 mL) is added 1N NaOH (0.4 mL) and the mixture is stirred at RT for 2 h. The reaction is continued overnight at reflux. The mixture is concentrated, diluted with water and acidified with 1N HCl until the pH is about 4. The solution is extracted with EtOAc (2×). The organic layers are combined, washed with brine, dried over MgSO$_4$, filtered and concentrated to provide 11a11.

Example 12

Preparation of Intermediate 12a2

44

-continued

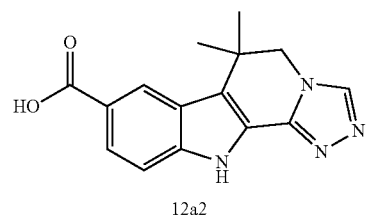

12a2

Step 1:

A mixture of 11a9 (100.0 mg, 0.35 mmol) and formic hydrazine (25.0 mg, 0.42 mmol, Aldrich) in cyclohexanol (1.0 mL) is heated at reflux overnight under a nitrogen atmosphere. Formic hydrazine (50.0 mg, 0.84 mmol) is added to the mixture that is then stirred at reflux for 16 h. Formic acid (50.0 mg, 0.84 mmol) is added and the reaction mixture is stirred for 2 days at 160° C. The mixture is cooled to RT and then triturated with EtOAc (2×) to provide 12a1.

Step 2:

To a solution of 12a1 (30.6 mg, 0.1 mmol) in DMSO (1.0 mL) is added 1N NaOH (0.52 mL, 0.52 mmol). The mixture is stirred at RT overnight. 1N NaOH (0.2 mL, 0.2 mmol) is added to the mixture which is then stirred for 2 h. The reaction mixture is acidified with 1N HCl (~0.5 mL) and extracted with EtOAc (3×). The combined organic extracts are combined, washed with brine, dried over MgSO$_4$, filtered and concentrated to provide 12a2.

Example 13

General Method A

Preparation of Intermediate 13a2

Example 13 is an example of a general method wherein the carboxylic partners, such as 2a4, are coupled with the appropriate Boc-protected partner, such as 13a0, followed by deprotection.

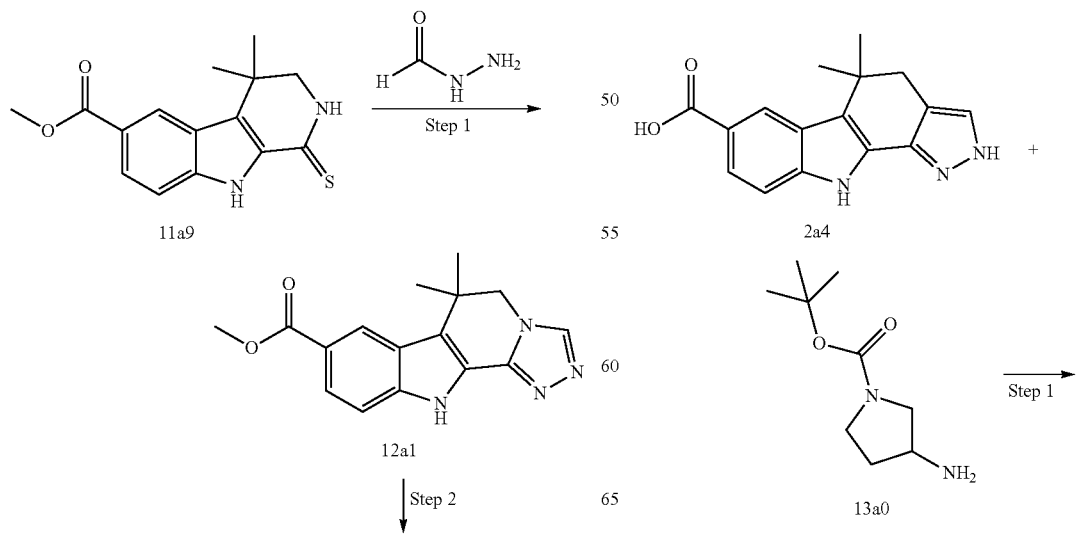

-continued

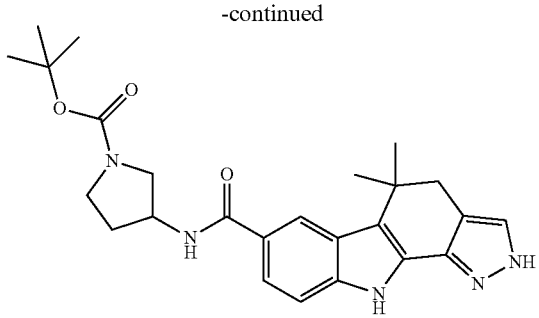

13a1

Step 2 ↓

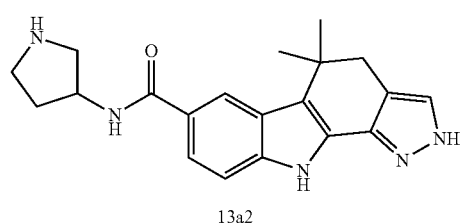

13a2

Step 1:

To a solution of 2a4 (200 mg, 0.71 mmol) and 13a0 (198.6 mg, 1.07 mmol, Chembridge) in DMF (5 mL) are added HATU (406.0 mg, 1.07 mmol) and TEA (0.2 mL, 1.42 mmol). The reaction mixture is stirred for 1 h at RT, quenched with AcOH (0.1 mL) and EtOAc and water are added. The layers are separated and the aqueous phase is extracted with EtOAc. The organic layers are combined, washed with brine, dried over $MgSO_4$, filtered and concentrated to provide 13a1.

Step 2:

13a1 (319.1 mg, 0.71 mmol) is dissolved in a 4N HCl solution of dioxane (2.0 mL, 0.5 mmol) and the solution is stirred for 30 min. The mixture is concentrated and purified by Combiflash (100% DCM to 10% MeOH/DCM) to provide 13a2.

Intermediates 13b2 to 13g2 are made analogously to the procedure described in Example 13.

13b2

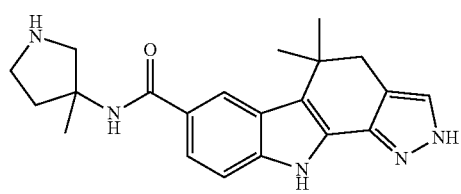

13c2

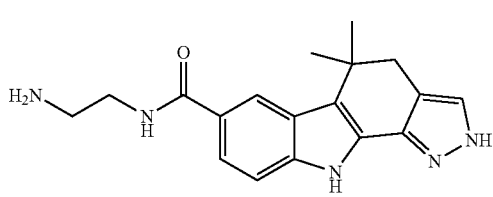

-continued

13d2

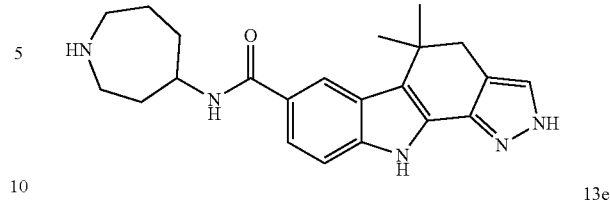

13e2

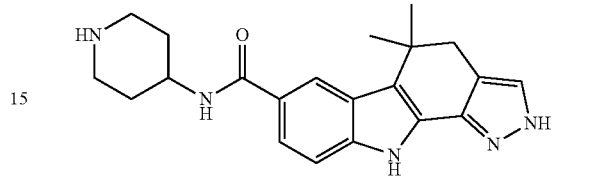

13f2

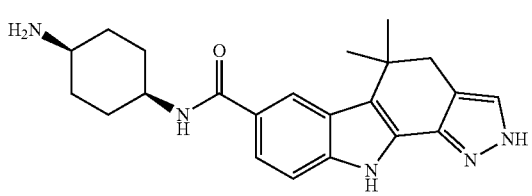

enantiomeric mixture of trans isomers

13g2

13h2

13i2 enantiomeric mixture of cis isomers

Example 14

General Method B

Preparation of Compound 1015

Example 14 is an example of a general method wherein the intermediate (13a2 to 13i2) obtained in Example 13 (GENERAL METHOD A) is coupled with the suitable carboxylic acid partner.

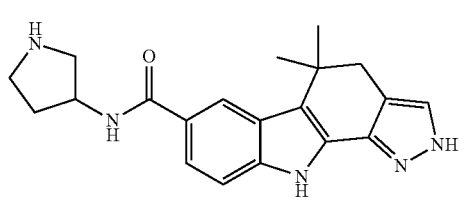

13a2

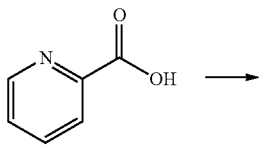

14a1

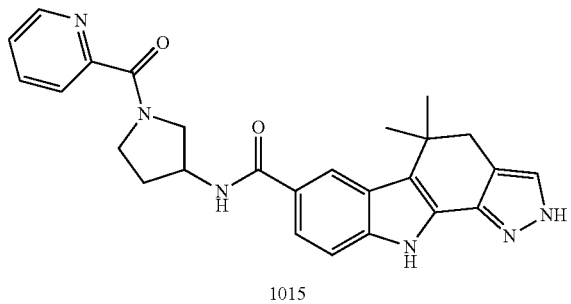

1015

To a solution of 13a2 (40.0 mg, 0.11 mmol) and 14a1 (12.7 mg, 0.10 mmol, Aldrich) in DMF (1.0 mL) are added HATU (49.4 mg, 0.11 mmol) and TEA (35.9 μL, 0.26 mmol). The reaction mixture is stirred for 4 h at RT, quenched with AcOH (0.2 mL) and the resulting solution is purified by preparative RP-HPLC to provide compound 1015.

Example 15

Preparation of Compound 1006

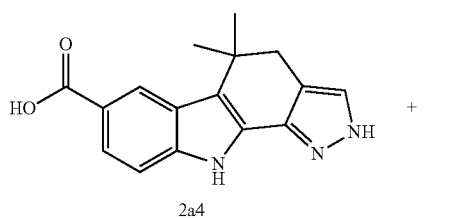

2a4

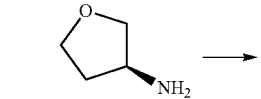

15a1

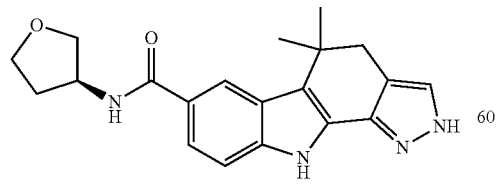

1006

To a solution of 2a4 (45.0 mg, 0.16 mmol) and 15a1 (39.5 mg, 0.32 mmol, Small-Molecule) in DMF (1 mL) are added HATU (91.3 mg, 0.24 mmol) and TEA (66.9 μL, 0.48 mmol). The reaction mixture is stirred for 1 h at RT, quenched with AcOH (0.1 mL) and purified by preparative RP-HPLC to provide compound 1006.

Example 16

Preparation of Compound 1126

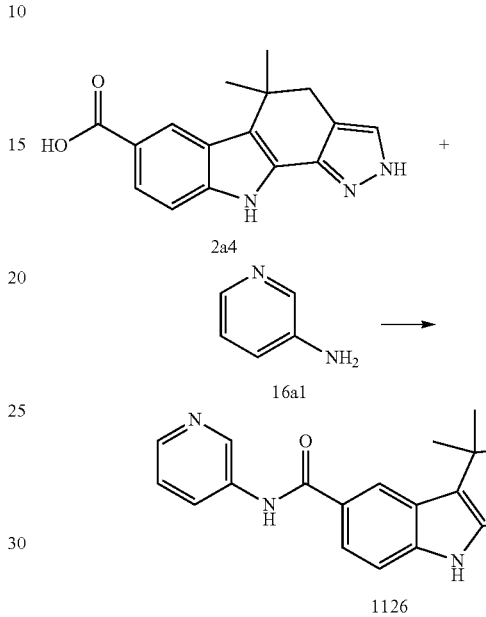

2a4 (50.0 mg, 0.18 mmol) and 16a1 (20.1 mg, 0.21 mmol, Aldrich) are dissolved in anhydrous pyridine (1.0 mL). The solution is cooled to −15° C. and phosphorus oxychloride (24.9 μL, 0.26 mmol) is added under stirring. The reaction mixture is stirred at −15° C. for 30 min and then is stirred at RT overnight. Phosphorus oxychloride (24.9 μL, 0.26 mmol) is added to the reaction mixture which is then stirred for 3 h at RT. The reaction mixture is quenched with 1N HCl (0.5 mL) and extracted with DCM using a phase-separator. The solvents are evaporated and the residue is purified by preparative RP-HPLC to provide compound 1126.

Example 17

Preparation of Compound 1117

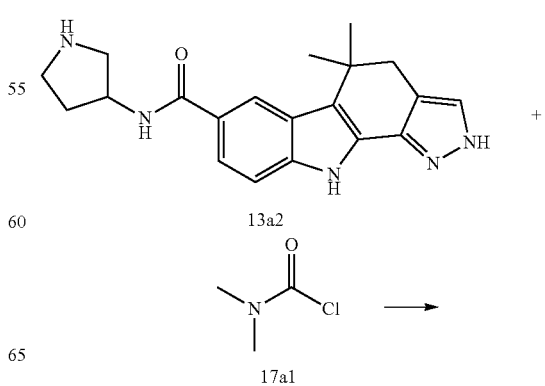

-continued

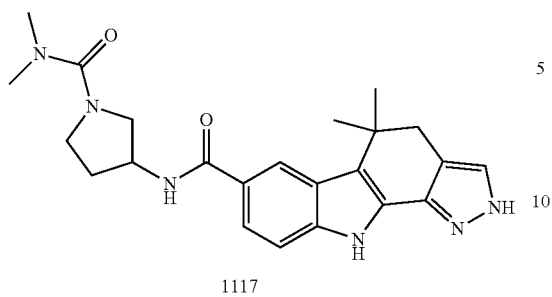

1117

A solution of 13a2 (20.0 mg, 0.06 mmol), 17a1 (6.3 µL, 0.07 mmol, Aldrich) and TEA (48.0 µL, 0.34 mmol) in THF (1.0 mL) is stirred overnight at RT. The reaction mixture is quenched with TFA (0.1 mL) and the resulting solution is concentrated in vacuo. The crude mixture is purified by preparative RP-HPLC to provide compound 1117.

Example 18

Preparation of Compound 1118

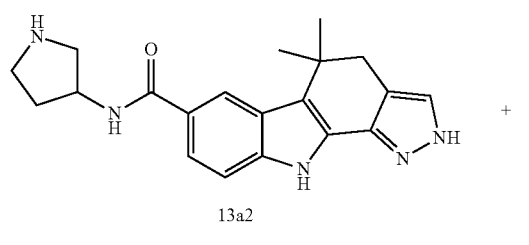

13a2

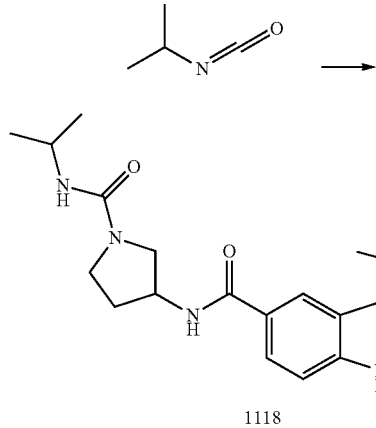

1118

A solution of 13a2 (20.0 mg, 0.06 mmol), isopropyl isocyanate (6.8 µL, 0.07 mmol, Aldrich) and TEA (48.0 µL, 0.34 mmol) in THF (1.0 mL) is stirred overnight at RT. The reaction mixture is quenched with TFA (0.1 mL) and the resulting solution is concentrated in vacuo. The crude mixture is purified by preparative RP-HPLC to provide compound 1118.

Example 19

Preparation of Intermediate 19a1

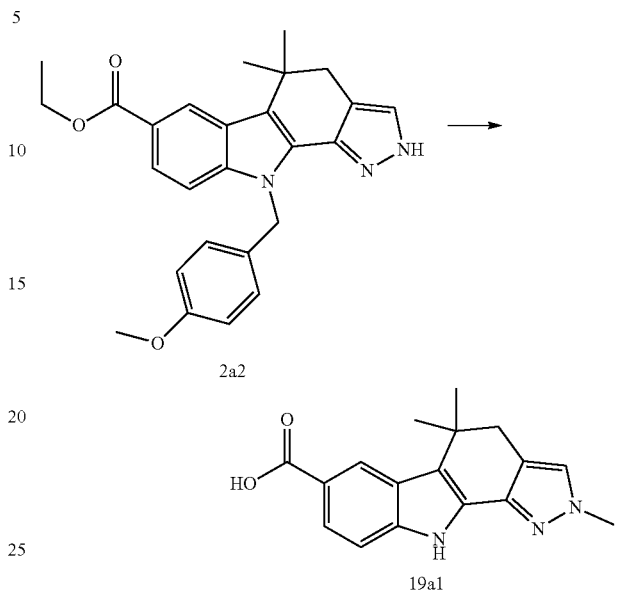

2a2

19a1

To a solution of 2a2 (175 mg, 0.41 mmol) in DMF (2 mL) is added NaH (60% in oil, 49 mg, 1.22 mmol) at 0° C. Iodomethane (30.2 µl, 0.49 mmol) is added and the reaction mixture is stirred at RT for 16 h. 5M NaOH (0.24 mL, 1.22 mmol) and DMSO (1 mL) are added. The reaction mixture is stirred at RT for 3 h, and then diluted with EtOAc and 1M HCl. The layers are separated and the organic layer is washed with water and brine, dried over $Na_2SO_4$ and concentrated. The residue is dissolved in TFA (2 mL) and triflic anhydride (40 µL) is added. The mixture is stirred at RT for 1 h, then concentrated and purified by Combiflash (0:100 to 5:95, MeOH/DCM) to provide 19a1.

Example 20

Preparation of Compound 2020

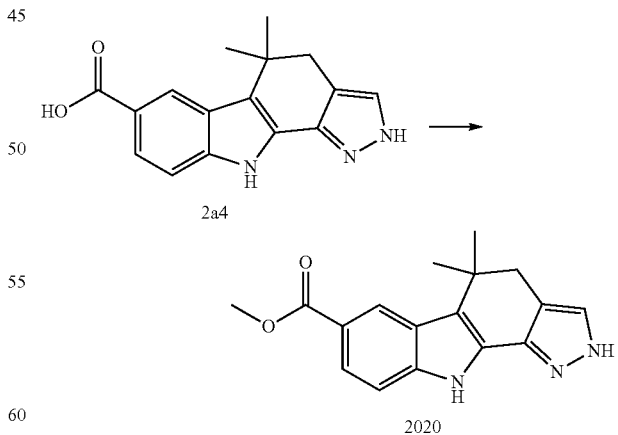

2a4

2020

2a4 (36 mg, 0.12 mmol) in ether/MeOH (1:1, 5 mL) is treated with TMS-diazomethane (2.0M, 2.5 mL). The resulting solution is stirred for 1 h at RT. The solvents are evaporated in vacuo. The residue is dissolved in DMSO, filtered and purified by preparative RP-HPLC to provide compound 2020.

Example 21

Preparation of Compound 1124

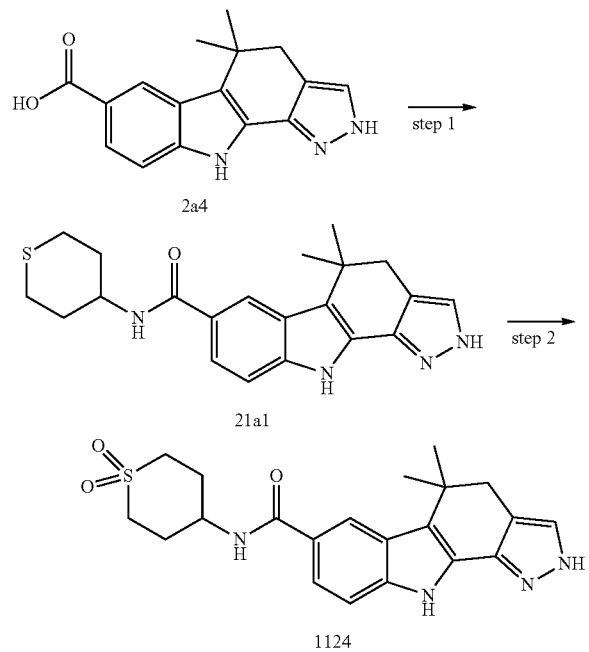

Step 1:

To a solution 2a4 (35 mg, 0.12 mmol) and HATU (52 mg, 0.14 mmol) in DMSO (0.5 mL) is added a solution of tetrahydrothiopyran-4-ylamine (18 mg, 0.15 mmol, Frontier) and TEA (0.087 mL, 0.62 mmol) in DMSO (1.5 mL). The resulting solution is stirred overnight at RT. The reaction mixture is then diluted with EtOAc and washed with an aqueous solution of saturated NaHCO$_3$, H$_2$O (2×) and brine. The organic layers are combined, dried over MgSO$_4$, filtered and concentrated to provide 21a1.

Step 2:

To 21a1 (44 mg, 0.11 mmol), in MeOH (3 mL) is added a solution of oxone (107 mg, 0.17 mmol) in H$_2$O (1.5 mL). The resulting suspension is stirred for 2 h at RT. The solvent is evaporated in vacuo. The residue is dissolved in DMSO, filtered and then purified by preparative RP-HPLC to provide compound 1124.

Example 22

Preparation of Intermediate 22a2

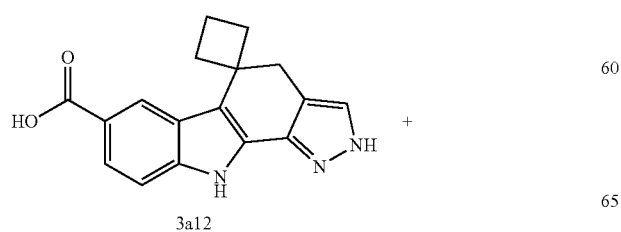

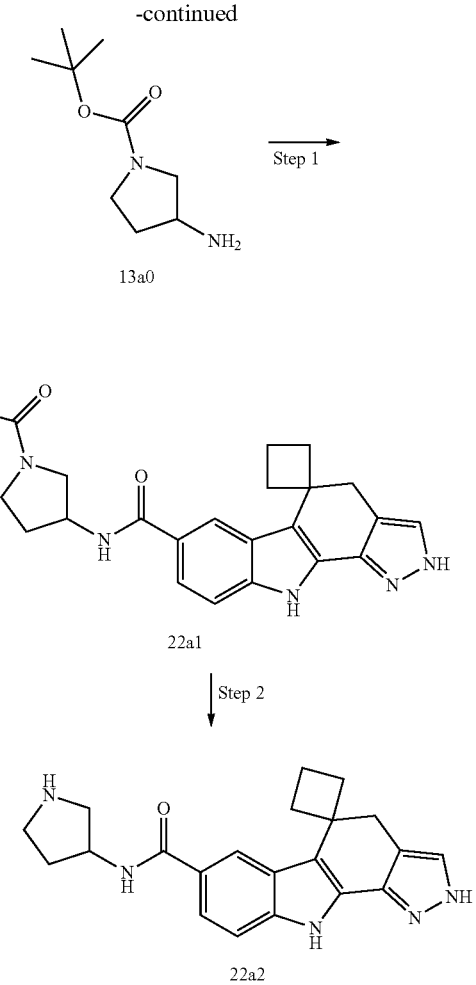

3a12 is coupled with 13a0 (step 1), followed by deprotection (step 2) using a procedure analogous to that described in Example 13 to provide intermediate 22a2.

Example 23

Preparation of Compound 5001

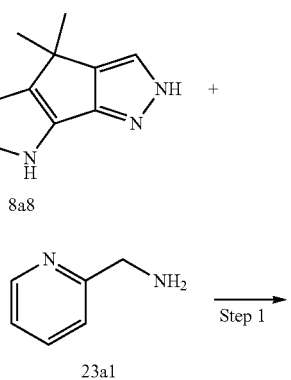

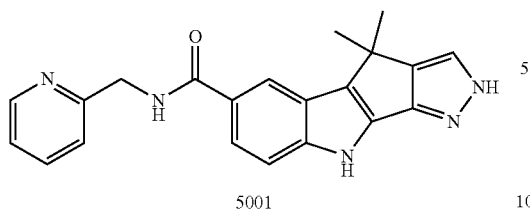

5001

8a8 is coupled with 23a1 (Aldrich) using a procedure analogous to that described in Step 9 of Example 8 to provide compound 5001.

Example 24

Preparation of Intermediate 24a2

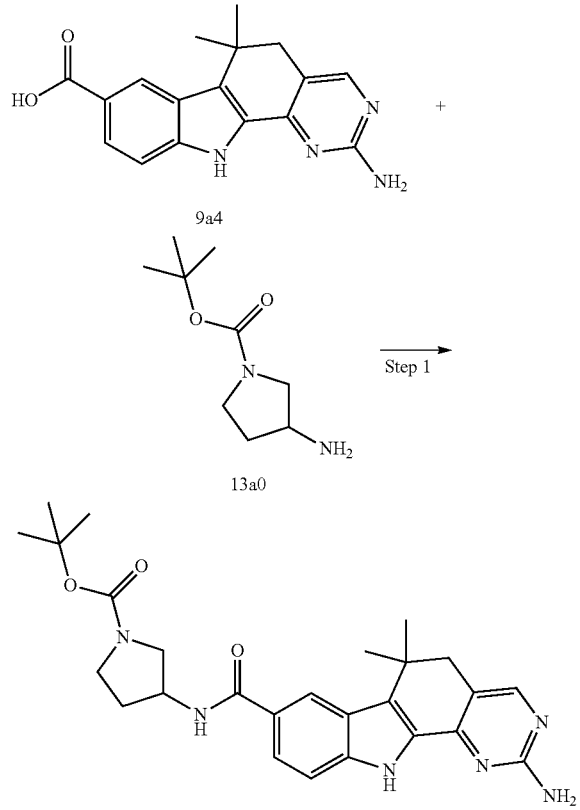

9a4 is coupled with 13a0 (step 1), followed by deprotection (step 2) using a procedure analogous to that described in Example 13 to provide intermediate 24a2.

Example 25

Preparation of Intermediate 25a2

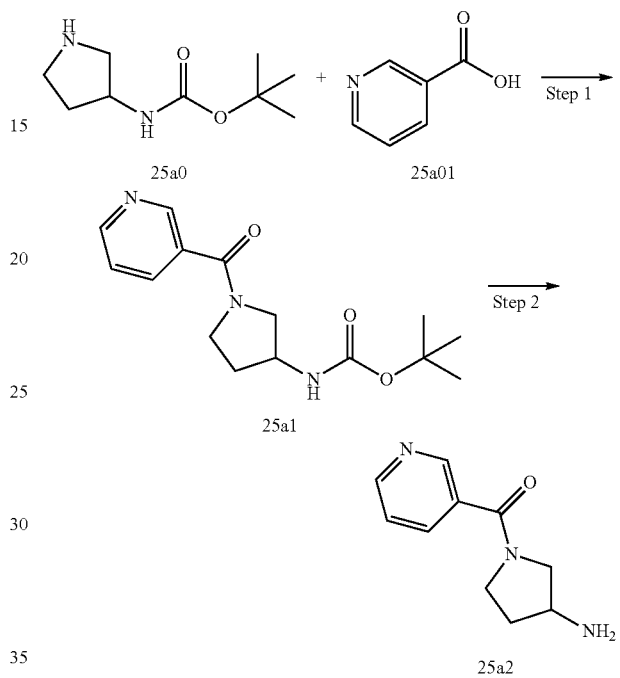

Step 1:
TEA (849 mL, 6.1 mmol), HATU (1.85 g, 4.88 mmol) and 25a0 (832 mg, 4.47 mmol, Aldrich) are added to a solution of 25a01 (500 mg, 4.1 mmol, Aldrich) in DMSO (5 mL). The reaction mixture is stirred for 1 h at RT, quenched with a saturated solution of $NH_4Cl$ (aqueous) and EtOAc and water are added. The layers are separated and the aqueous phase is extracted with EtOAc. The organic layers are combined, washed with brine, dried over $MgSO_4$, filtered and concentrated to provide 25a1.

Step 2:
25a1 (443 mg, 1.52 mmol) is dissolved in a 4N HCl solution of dioxane (10.0 mL, 40 mmol) and MeOH (2 mL). The resulting solution is stirred for 30 min and then concentrated to provide 25a2.

Example 26

Preparation of Intermediate 26a2

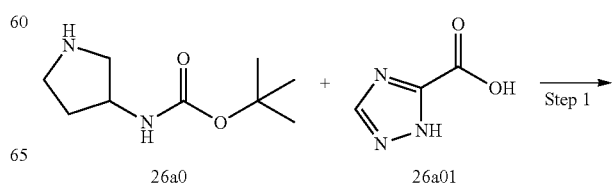

-continued

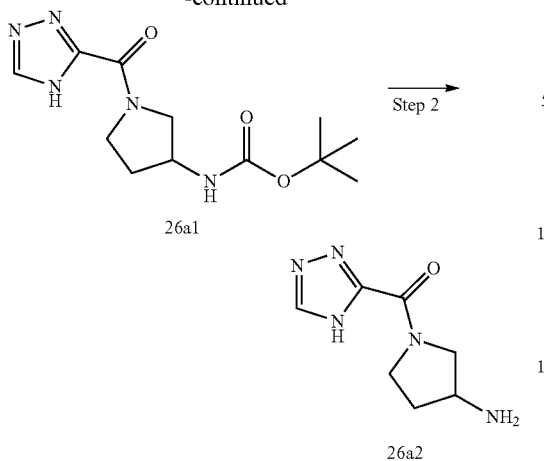

26a0 (TCI-US) is coupled with 26a01 (Anichem) (step 1), followed by deprotection (step 2) using a procedure analogous to that described in Example 25 to provide intermediate 26a2.

Example 27

Preparation of Compound 2001

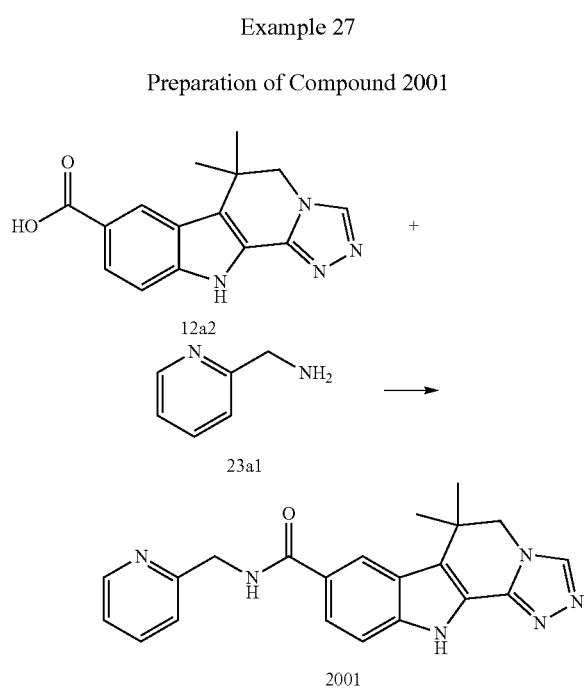

12a2 is coupled with 23a1 using a procedure analogous to that described in Example 15 to provide compound 2001.

Example 28

Preparation of Compound 1011

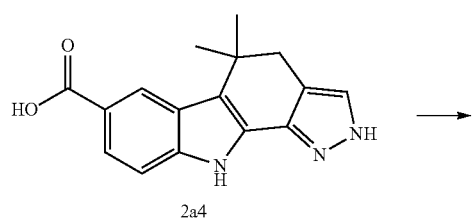

-continued

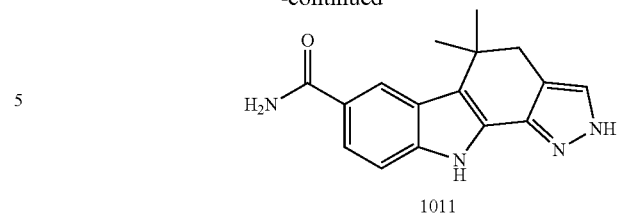

TEA (67 μL, 0.48 mmol) and HATU (91 mg, 0.24 mmol) are added to a solution of ammonium bicarbonate (10.9 mg, 0.64 mmol) and 2a4 (45.0 mg, 0.16 mmol) in DMF (1 mL). The reaction mixture is stirred for 1 h at RT, filtered and purified by preparative RP-HPLC to provide compound 1011.

Example 29

Preparation of Compound 2012

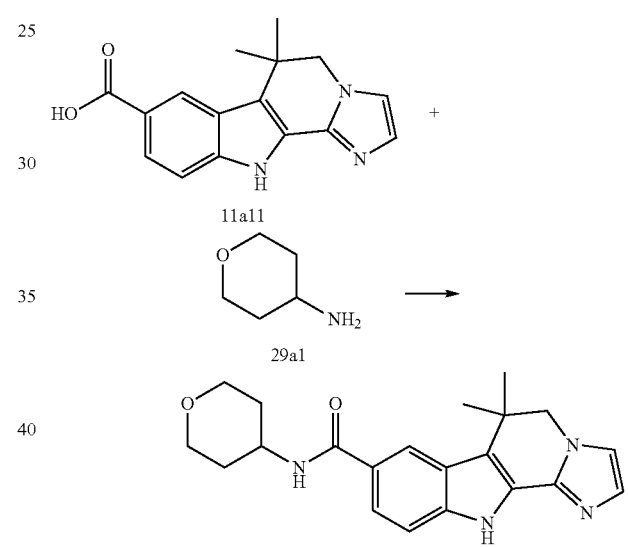

11a11 is coupled with 29a1 (Oakwood) using a procedure analogous to that described in Example 15 to provide compound 2012.

Example 30

Preparation of Compound 3011

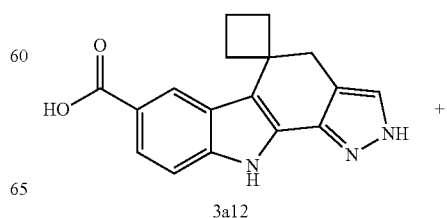

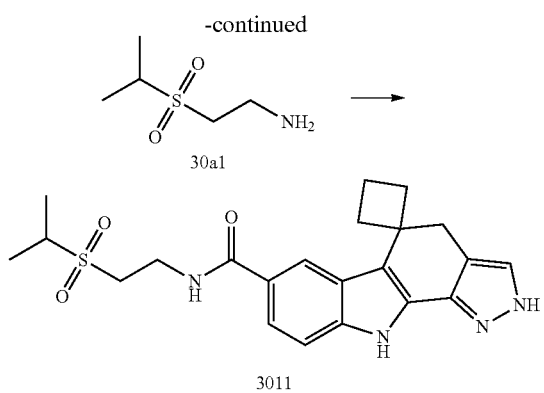

3a12 is coupled with 30a1 (Princeton) using a procedure analogous to that described in Example 15 to provide compound 3011.

Example 31

Preparation of Compound 2018

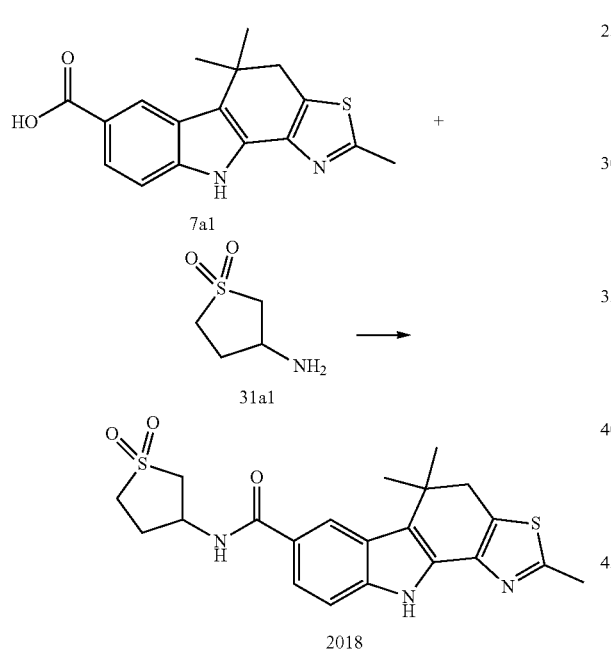

7a1 is coupled with 31a1 (Intermed) using a procedure analogous to that described in Example 15 to provide compound 2018.

Example 32

Preparation of Compound 2004

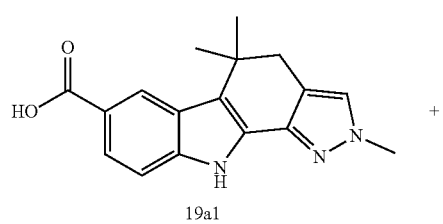

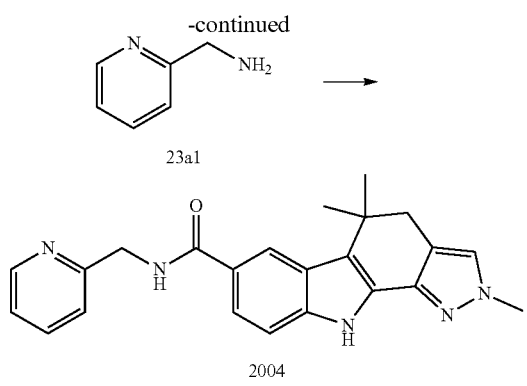

19a1 is coupled with 23a1 (Aldrich) using a procedure analogous to that described in Example 15 to provide compound 2004.

Example 33

Preparation of Compound 2028

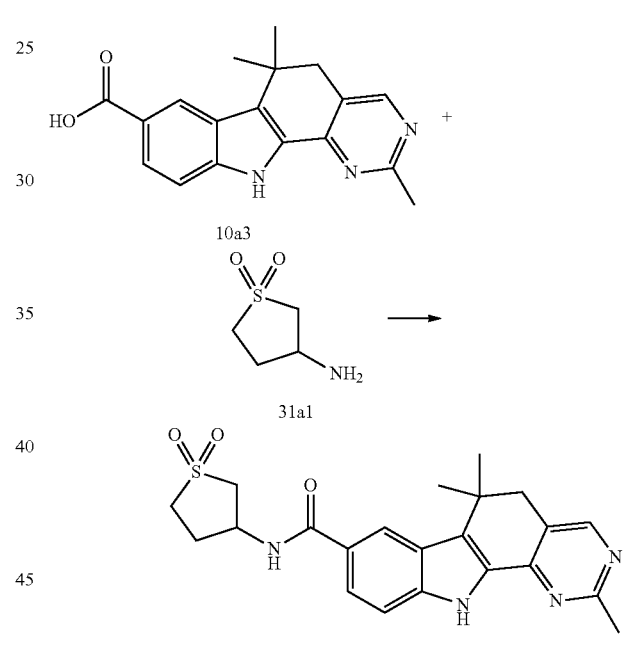

10a3 is coupled with 31a1 using a procedure analogous to that described in Example 15 to provide compound 2028.

Example 34

Preparation of Compound 2014

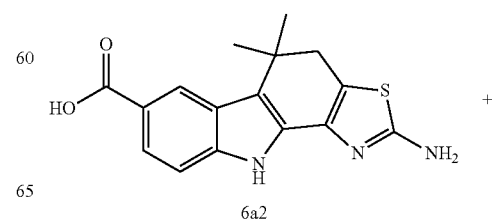

-continued

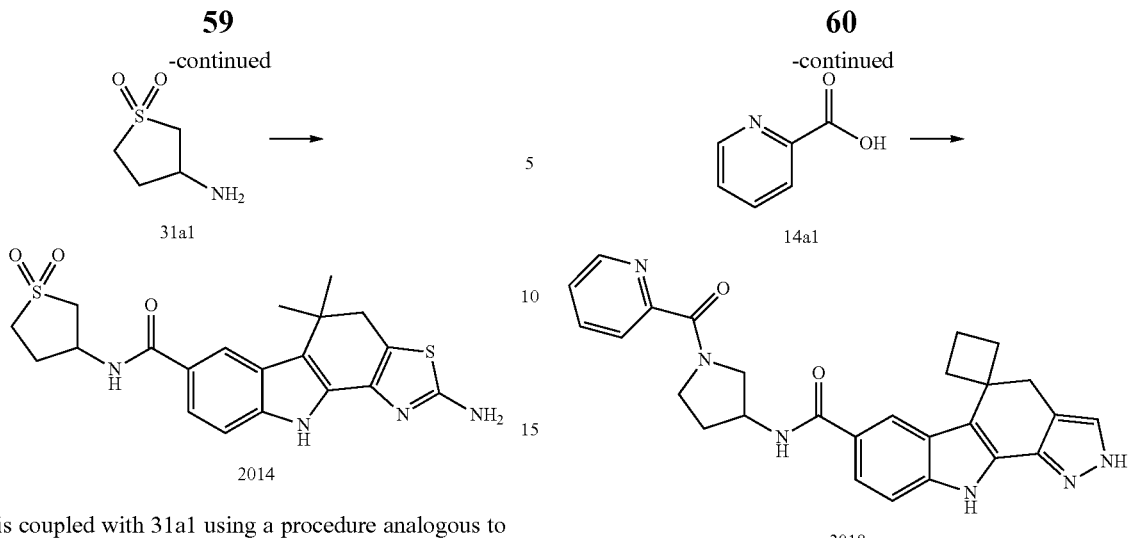

6a2 is coupled with 31a1 using a procedure analogous to that described in Example 15 to provide compound 2014.

Example 35

Preparation of Compound 2022

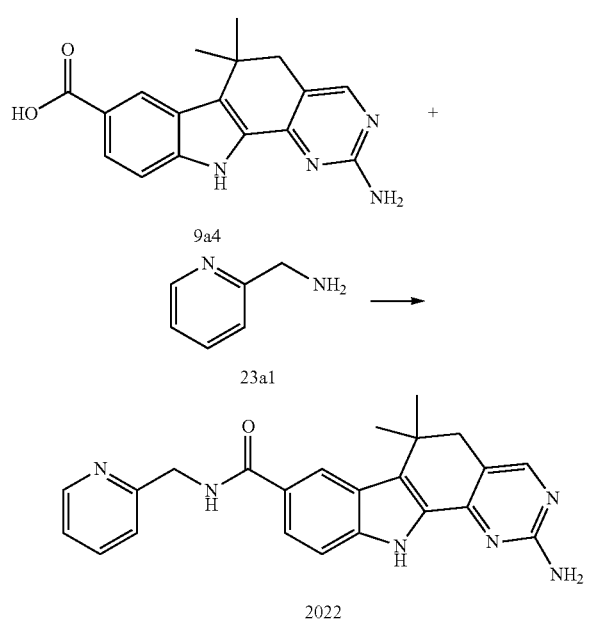

9a4 is coupled with 23a1 using a procedure analogous to that described in Example 15 to provide compound 2022.

Example 36

Preparation of Compound 3018

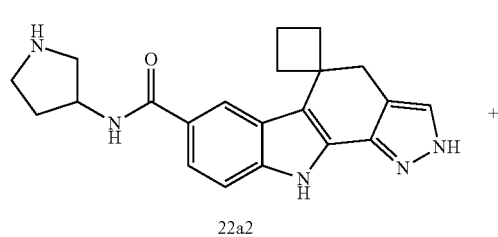

22a2 is coupled with 14a1 using a procedure analogous to that described in Example 14 to afford compound 3018.

Example 37

Preparation of Compound 4004

4a8 is coupled with 23a1 using a procedure analogous to that described in Example 15 to provide compound 4004.

Example 38

Preparation of Compound 2027

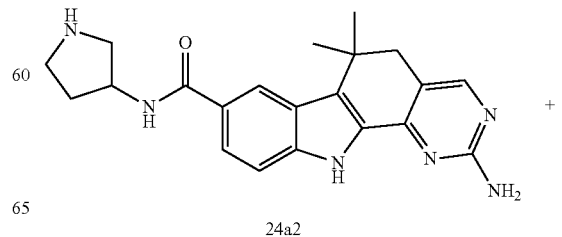

-continued

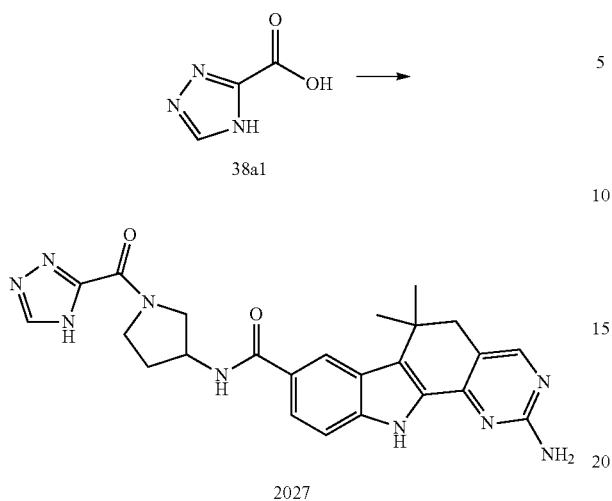

24a2 is coupled with 38a1 (Aldrich) using a procedure analogous to that described in Example 14 to afford compound 2027.

Example 39

Preparation of Compound 2015

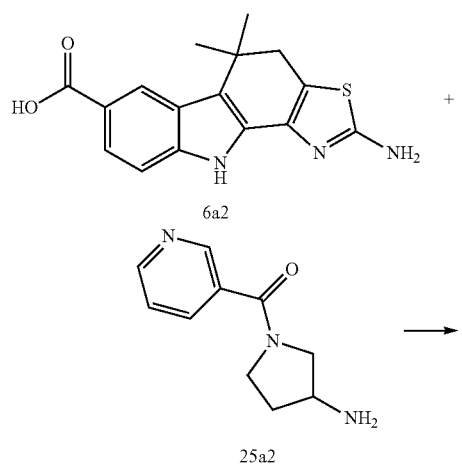

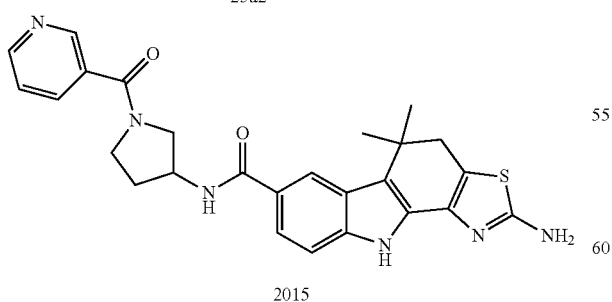

6a2 is coupled with 25a2 using a procedure analogous to that described in Example 15 to provide compound 2015.

Example 40

Preparation of Compound 2019

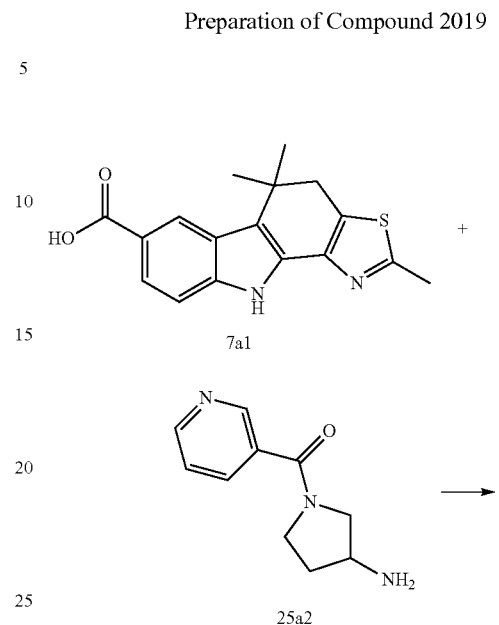

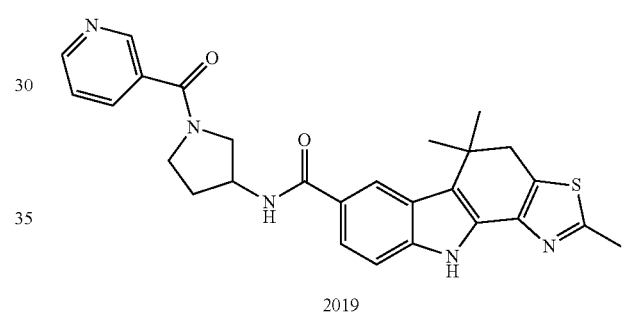

7a1 is coupled with 25a2 using a procedure analogous to that described in Example 15 to provide compound 2019.

Example 41

Preparation of Compound 5002

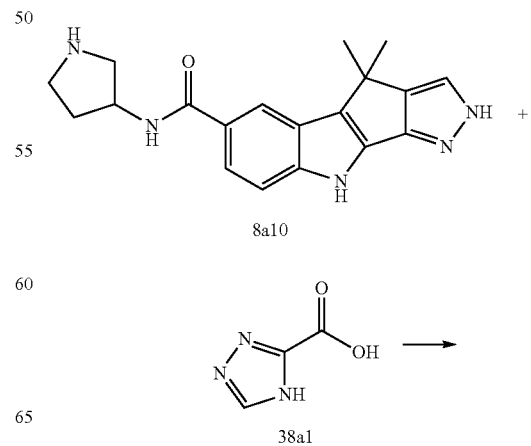

-continued

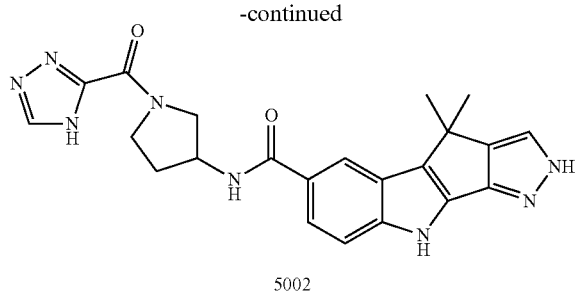

5002

38a1 is coupled with 8a10 using a procedure analogous to that described in Example 14 to afford compound 5002.

Example 42

Preparation of Compound 2002

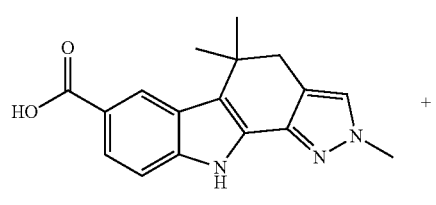

19a1

+

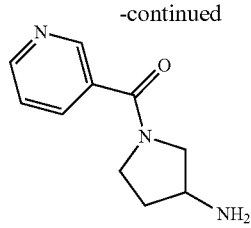

25a2

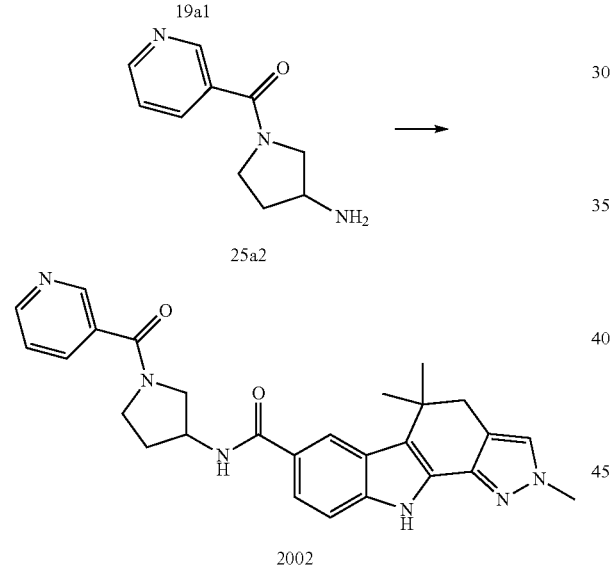

2002

19a1 is coupled with 25a2 using a procedure analogous to that described in Example 15 to provide compound 2002.

Example 43

Preparation of Compound 4001

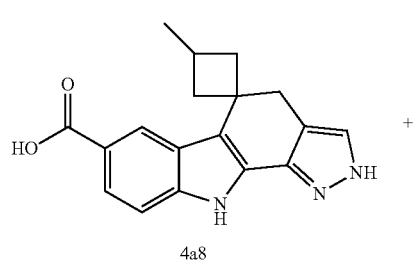

4a8

-continued

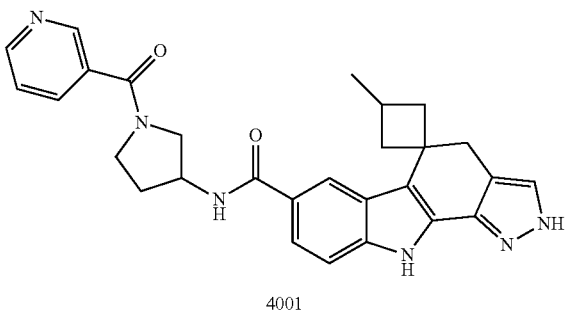

25a2

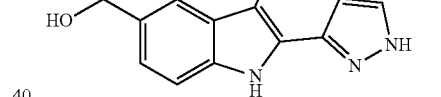

4001

4a8 is coupled with 25a2 using a procedure analogous to that described in Example 15 to provide compound 4001.

Example 44

Preparation of Compound 4002

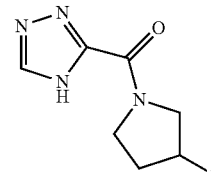

4a8

+

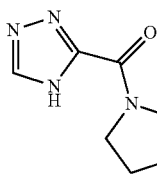

26a2

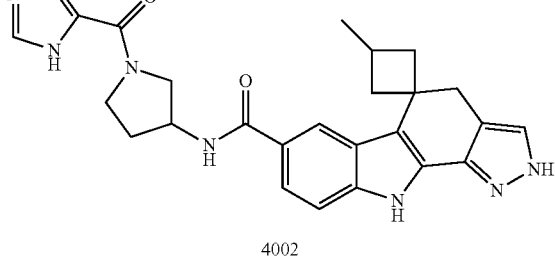

4002

4a8 is coupled with 26a2 using a procedure analogous to that described in Example 15 to provide compound 4002.

Example 45

Preparation of Compound 2029

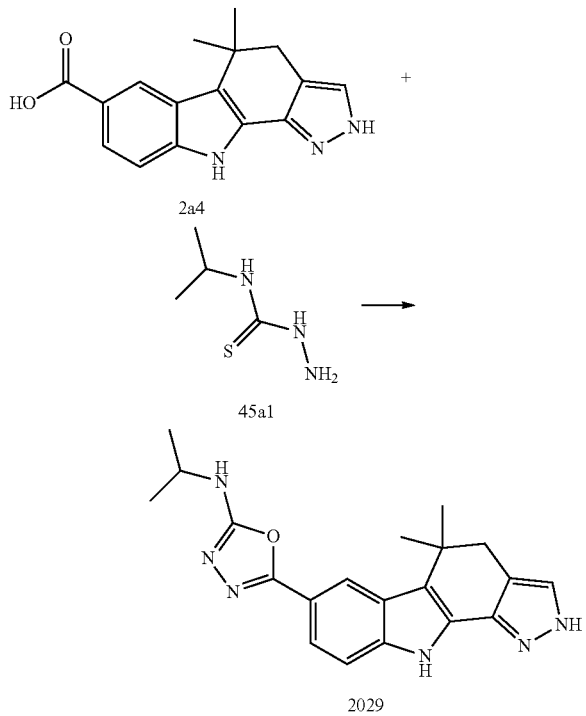

EDCI (150 mg, 0.78 mmol) is added to a solution of 45a1 (27 mg, 0.2 mmol, TCI-US) and 2a4 (50 mg, 0.18 mmol) in DMF (2 mL). The reaction mixture is stirred at RT for 18 h, quenched with AcOH (0.2 mL) and purified by RP-HPLC to provide compound 2029.

Example 46

Production of HCV pseudoparticles (HCVpp) and VSV pseudoparticles (VSVpp) Functional HCVpp are produced in 293FT cells (Invitrogen, Cat. No. R700-07) by co-transfection of HCV E1/E2 expression construct (pE1E2Con1#3) and a non-replicating HIV-1 based reporter vector (pNL4.3LucE-R-Δ725). The pNL4.3LucE-R-Δ725 reporter vector is generated by deleting a 725 pb DNA fragment within the gp160 encoding sequence corresponding to the StuI/BsaI restriction fragment of the original reporter vector (pNL4.3LucE-R-: NIH AIDS Research & Reference Reagent Program, Cat. No. 3418). The pE1E2Con1#3 expression vector encodes the HCV envelope gene (residues 171-746) (HCV isolate Con1, accession number AJ238799) cloned (HindIII/XbaI) into the pcDNA™ 3.1/Hygro$^{(+)}$ expression vector (Invitrogen Cat. No. V870-20). For HCVpp production, 293FT cells are co-transfected with pNL4.3LucE-R-Δ725 reporter vector and pE1/E2Con1#3 expression vector in a 30:1 (μg:μg) ratio using Lipofectamine™ 2000 (Invitrogen Cat. No. 11668-027) in serum-free Opti-MEM®I medium (Invitrogen Cat. No. 31985-070). Six hours post-transfection, the transfection medium is replaced with DMEM medium (Invitrogen, Cat. No. 319-005-CL) supplemented with 3% FBS (HyClone, Cat. No. SH30396.03) and 0.1 mM NEAA (Invitrogen, Cat. No. 11140-050). Cell culture supernatants containing HCVpp are collected at 48 hours post-transfection and centrifuged at 1000×g for 10 min to remove cellular debris. HEPES buffer (1M, pH7.5, Invitrogen Cat. No. 15630-080) is added at a final concentration of 10 mM to the clarified viral HCVpp containing supernatants, aliquoted and stored at −80° C. VSV pseudoparticles (VSVpp) for evaluating specificity of the compounds are generated according to the above transfection protocol using a pLP-VSVG (Invitrogen, Cat. No. K4975-00) expression vector encoding the G envelope gene of VSV rather than the pE1E2Con1#3 expression vector.

Infection with HCV Pseudoparticles (HCVpp)

HCVpp incorporating a lentiviral backbone harboring the luciferase gene are used to assay for HCV entry as follows. Hep3B2.1-7 (ATCC number HB-8064) cells seeded in 96-well plates (Black 96-well ViewPlate™, Packard Cat. No. 6005182) are incubated with a concentration range of the tested compounds and supernatant containing HCVpp and polybrene. Typically the different reagents are mixed as follows: 10 μL of cells (1×10$^6$ cells/mL in DMEM medium supplemented with 3% FBS and 0.1 mM NEAA), 15 μL of compound solution (DMEM medium supplemented with 3% FBS, 0.1 mM NEAA and 3% DMSO) and 50 μL of undiluted supernatant containing HCVpp to which a solution of polybrene is added (Sequa-brene, Sigma Cat. No. S2667, final concentration of 4.5 mg/mL). The plates are centrifuged for 60 min at 400×g and then incubated for 4 h at 37° C. (5% CO$_2$) before addition of 10 μL of DMEM medium supplemented with 20% FBS and 0.1 mM NEAA. Seventy-two hours after infection the luciferase level is evaluated by a standard luminescences assay. Compounds that reduce viral entry limit the amount of HCVpp that is transduced into the host cells and thus reduce the luciferase levels and the resulting luminescence signal. The most efficacious compounds induce the most significant reduction in luminescence.

Specificity of the compounds is tested by evaluating the inhibitory effect on VSVpp according to the infection protocol described above for HCVpp, except that supernatant containing VSVpp is diluted in media to generate a similar signal as generated using the supernatant containing undiluted HCVpp. Compounds that inhibit HCVpp entry significantly more (10-fold) than infections mediated by VSVpp are considered to be specific. All the compounds listed in Tables 1 and 5 are found to significantly reduce viral entry as measured by the HCVpp/luciferase assay, and are specific when assayed against the inhibitory effect on VSVpp.

The compounds of the invention show EC$_{50}$ values in the range of 2.5 μM or less in the assay of Example 46. Representative data is shown below:

| Cmpd # | EC$_{50}$ (nM) Example 46 |
|---|---|
| 1006 | 112 |
| 1011 | 72 |
| 1015 | 12 |
| 1126 | 65 |
| 1118 | 19 |
| 2001 | 1395 |
| 2004 | 109 |
| 2012 | 230 |
| 2014 | 280 |
| 2018 | 320 |
| 2020 | 97 |
| 2022 | 1350 |
| 2028 | 885 |
| 3011 | 2.8 |
| 3018 | 6.7 |
| 4004 | 54 |
| 5002 | 59 |

Tables of Compounds

The following tables list compounds representative of the invention. All of the compounds in Tables 1 to 5 are synthesized analogously to the Examples described above. It will be apparent to a skilled person that the analogous synthetic routes may be used, with appropriate modifications, to prepare the compounds of the invention as described herein.

Retention times ($t_R$) for each compound are measured using the standard analytical HPLC or UPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC or UPLC instruments. Even when measured on the same instrument, the values may vary when measured, for example, using different individual HPLC or UPLC columns, or, when measured on the same instrument and the same individual column, the values may vary, for example, between individual measurements taken on different occasions.

TABLE 1

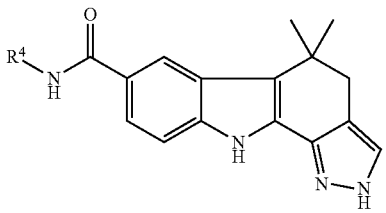

| Cmpd # | R[4] | $t_R$ (min) | $(M + H)^+$ | Ex. # |
|---|---|---|---|---|
| 1001 | | 1.51 | 455.3 | 13a2 & Ex. 14 |
| 1002 | | 1.4 | 399.2 | Ex. 15 |
| 1003 | | 1.55 | 372.2 | Ex. 15 |
| 1004 | | 1.53 | 413.3 | Ex. 15 |
| 1005 | | 1.35 | 387.3 | Ex. 15 |
| 1006 | | 1.49 | 351.4 | Ex. 15 |
| 1007 | | 1.51 | 387.3 | Ex. 15 |
| 1008 | | 1.39 | 377.3 | Ex. 15 |

TABLE 1-continued
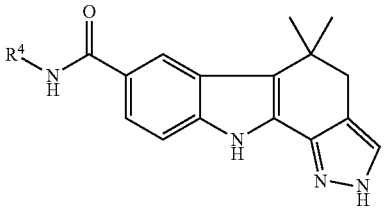
| Cmpd # | R⁴ | $t_R$ (min) | (M + H)⁺ | Ex. # |
|---|---|---|---|---|
| 1009 | 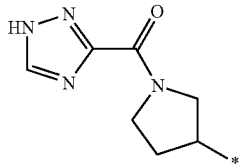 [SMILES: *C1CCN(C(=O)c2nc[nH]n2)C1] | 1.53 | 365.4 | Ex. 15 |
| 1010 | CH₃ | 1.42 | 295.3 | Ex. 15 |
| 1011 | H | 1.31 | 281.2 | Ex. 28 |
| 1012 | 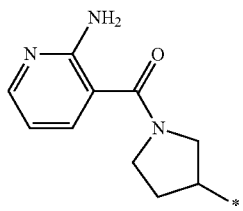 [SMILES: *C1CCN(C(=O)c2cccnc2N)C1] | 1.56 | 445.3 | 13a2 & Ex. 14 |
| 1013 | 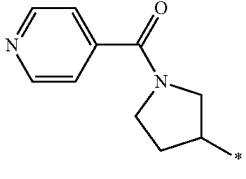 [SMILES: *C1CCN(C(=O)c2ccncc2)C1] | 1.51 | 470.3 | 13a2 & Ex. 14 |
| 1014 | 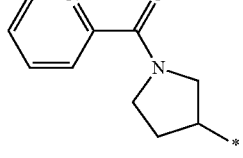 | 1.47 | 455.3 | 13a2 & Ex. 14 |
| 1015 | 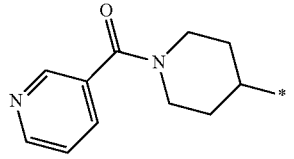 [SMILES: *C1CCN(C(=O)c2cccnc2)CC1] | 1.55 | 455.3 | 13a2 & Ex. 14 |
| 1016 | 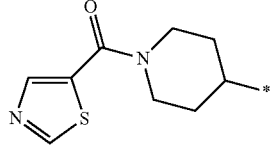 [SMILES: *C1CCN(C(=O)c2cncs2)CC1] | 1.58 | 469.3 | 13e2 & Ex. 14 |
| 1017 |  | 1.59 | 475.3 | 13e2 & Ex. 14 |

TABLE 1-continued
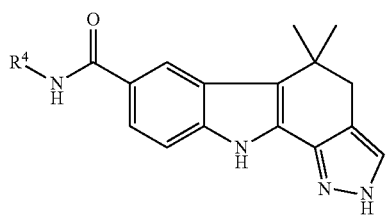
| Cmpd # | R⁴ | $t_R$ (min) | (M + H)⁺ | Ex. # |
|---|---|---|---|---|
| 1018 | (1H-pyrazol-3-yl)carbonyl-piperidin-4-yl | 1.56 | 458.3 | 13e2 & Ex. 14 |
| 1019 | (3-methylisoxazol-4-yl)carbonyl-piperidin-4-yl | 1.62 | 473.3 | 13e2 & Ex. 14 |
| 1020 | (5-methylisoxazol-4-yl)carbonyl-piperidin-4-yl | 1.63 | 473.3 | 13e2 & Ex. 14 |
| 1021 | (isoxazol-5-yl)carbonyl-piperidin-4-yl | 1.61 | 459.3 | 13e2 & Ex. 14 |
| 1022 | (3-amino-1H-1,2,4-triazol-5-yl)carbonyl-piperidin-4-yl | 1.46 | 474.3 | 13e2 & Ex. 14 |
| 1023 | (1H-1,2,4-triazol-3-yl)carbonyl-piperidin-4-yl | 1.5 | 459.3 | 13e2 & Ex. 14 |
| 1024 | (oxazol-5-yl)carbonyl-piperidin-4-yl | 1.55 | 459.3 | 13e2 & Ex. 14 |

TABLE 1-continued

| Cmpd # | R⁴ | $t_R$ (min) | (M + H)⁺ | Ex. # |
|---|---|---|---|---|
| 1025 | (6-methylsulfonyl-pyridin-3-yl)carbonyl-piperidin-4-yl | 1.55 | 547.3 | 13e2 & Ex. 14 |
| 1026 | (1-methyl-imidazol-5-yl)carbonyl-piperidin-4-yl | 1.5 | 472.3 | 13e2 & Ex. 14 |
| 1027 | 1-(pyridin-3-ylcarbonyl)piperidin-3-yl | 1.61 | 469.3 | 13c2 & Ex. 14 |
| 1028 | 1-(6-methyl-pyridin-3-ylcarbonyl)piperidin-3-yl | 1.67 | 483.3 | 13c2 & Ex. 14 |
| 1029 | 1-(thiazol-5-ylcarbonyl)piperidin-3-yl | 1.63 | 475.2 | 13c2 & Ex. 14 |

TABLE 1-continued
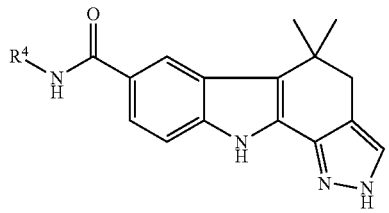
| Cmpd # | R⁴ | $t_R$ (min) | (M + H)⁺ | Ex. # |
| --- | --- | --- | --- | --- |
| 1030 | piperidine-N-C(O)-(1H-pyrazol-3-yl), * at 3-position | 1.6 | 458.3 | 13c2 & Ex. 14 |
| 1031 | piperidine-N-C(O)-(3-methylisoxazol-4-yl), * at 3-position | 1.68 | 473.3 | 13c2 & Ex. 14 |
| 1032 | piperidine-N-C(O)-(5-methylisoxazol-4-yl), * at 3-position | 1.67 | 473.3 | 13c2 & Ex. 14 |
| 1033 | piperidine-N-C(O)-(isoxazol-5-yl), * at 3-position | 1.64 | 459.3 | 13c2 & Ex. 14 |
| 1034 | piperidine-N-C(O)-(1H-1,2,4-triazol-3-yl), * at 3-position | 1.54 | 459.3 | 13c2 & Ex. 14 |

TABLE 1-continued
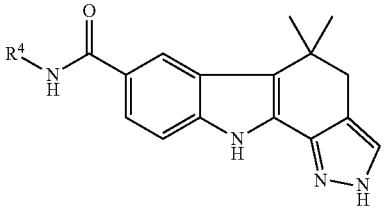
| Cmpd # | R⁴ | $t_R$ (min) | (M + H)⁺ | Ex. # |
|---|---|---|---|---|
| 1035 | 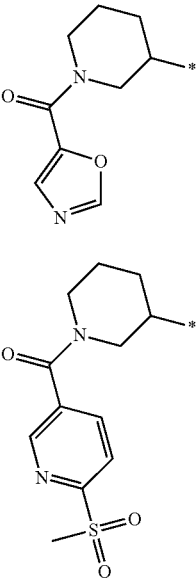 | 1.61 | 459.3 | 13c2 & Ex. 14 |
| 1036 | 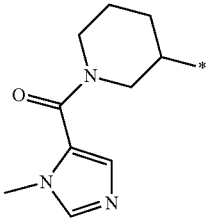 [SMILES: *C1CCCN(C(=O)c2cncn2C)C1] | 1.58 | 547.3 | 13c2 & Ex. 14 |
| 1037 | 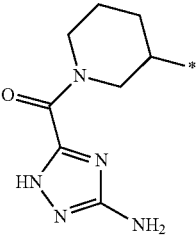 [SMILES: *C1CCCN(C(=O)c2nc(N)n[nH]2)C1] | 1.55 | 472.3 | 13c2 & Ex. 14 |
| 1038 | 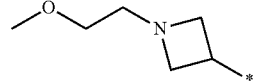 [SMILES: *C1CN(CCOC)C1] | 1.51 | 474.3 | 13c2 & Ex. 14 |
| 1039 | 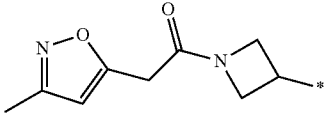 [SMILES: *C1CN(C(=O)Cc2cc(C)no2)C1] | 1.35 | 394.3 | Ex. 15 |
| 1040 |  | 1.58 | 459.3 | 13b2 & Ex. 14 |

TABLE 1-continued
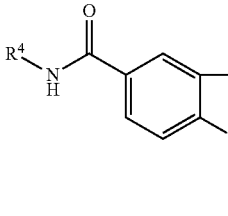
| Cmpd # | R⁴ | $t_R$ (min) | (M + H)⁺ | Ex. # |
|---|---|---|---|---|
| 1041 | 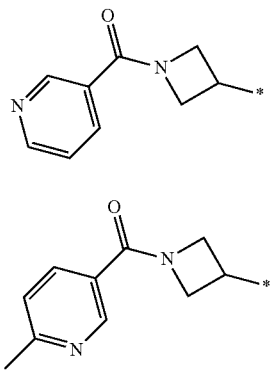 | 1.55 | 441.2 | 13b2 & Ex. 14 |
| 1042 | 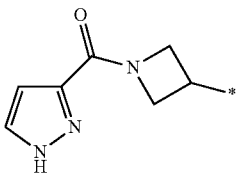 [SMILES: *C1CN(C(=O)c2cc[nH]n2)C1] | 1.62 | 455.3 | 13b2 & Ex. 14 |
| 1043 | 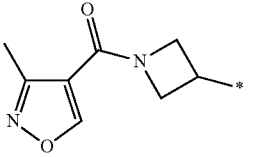 [SMILES: *C1CN(C(=O)c2conc2C)C1] | 1.53 | 430.2 | 13b2 & Ex. 14 |
| 1044 | 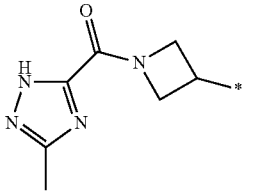 [SMILES: *C1CN(C(=O)c2nc(C)n[nH]2)C1] | 1.62 | 445.3 | 13b2 & Ex. 14 |
| 1045 | 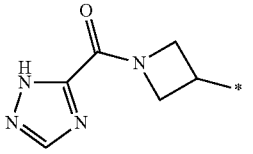 [SMILES: *C1CN(C(=O)c2ncn[nH]2)C1] | 1.52 | 445.2 | 13b2 & Ex. 14 |
| 1046 | 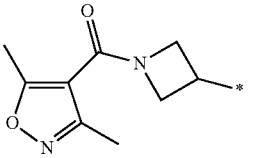 [SMILES: *C1CN(C(=O)c2c(C)noc2C)C1] | 1.48 | 431.2 | 13b2 & Ex. 14 |
| 1047 | | 1.64 | 459.3 | 13b2 & Ex. 14 |

TABLE 1-continued

| Cmpd # | R⁴ | $t_R$ (min) | (M + H)⁺ | Ex. # |
|---|---|---|---|---|
| 1048 | 4-methylpyrazol-1-yl-acetyl-azetidin-3-yl | 1.64 | 458.3 | 13b2 & Ex. 14 |
| 1049 | 1-methyl-1H-pyrazole-5-carbonyl-azetidin-3-yl | 1.63 | 444.3 | 13b2 & Ex. 14 |
| 1050 | 6-(methylsulfonyl)pyridine-3-carbonyl-azetidin-3-yl | 1.52 | 519.3 | 13b2 & Ex. 14 |
| 1051 | 6-methylpyridine-3-carboxamido-ethyl | 1.62 | 443.3 | 13h2 & Ex. 14 |
| 1052 | 1H-pyrazole-3-carboxamido-ethyl | 1.5 | 418.2 | 13h2 & Ex. 14 |
| 1053 | 5-methyl-1H-pyrazole-3-carboxamido-ethyl | 1.56 | 432.3 | 13h2 & Ex. 14 |
| 1054 | 5-methylisoxazole-4-carboxamido-ethyl | 1.64 | 433.3 | 13h2 & Ex. 14 |

TABLE 1-continued

| Cmpd # | R⁴ | t_R (min) | (M + H)⁺ | Ex. # |
|---|---|---|---|---|
| 1055 | pyridazine-3-carboxamide-ethyl | 1.51 | 430.2 | 13h2 & Ex. 14 |
| 1056 | 1H-1,2,4-triazole-3-carboxamide-ethyl | 1.44 | 419.3 | 13h2 & Ex. 14 |
| 1057 | 1-methyl-1H-pyrazolo[3,4-b]pyridine-3-carboxamide-ethyl | 1.72 | 483.3 | 13h2 & Ex. 14 |
| 1058 | (5-methylpyrazin-2-yl)(pyrrolidin-3-yl)methanone | 1.64 | 470.3 | 13a2 & Ex. 14 |
| 1059 | (1,3-dimethyl-1H-pyrazol-5-yl)(pyrrolidin-3-yl)methanone | 1.67 | 472.3 | 13a2 & Ex. 14 |
| 1060 | pyrazin-2-yl(pyrrolidin-3-yl)methanone | 1.59 | 456.3 | 13a2 & Ex. 14 |
| 1061 | (1H-pyrazol-3-yl)(pyrrolidin-3-yl)methanone | 1.54 | 444.3 | 13a2 & Ex. 14 |
| 1062 | (tetrahydrofuran-3-yl)(pyrrolidin-3-yl)methanone | 1.55 | 448.3 | 13a2 & Ex. 14 |

TABLE 1-continued

| Cmpd # | R⁴ | t_R (min) | (M + H)⁺ | Ex. # |
|---|---|---|---|---|
| 1063 | 3-methylisoxazol-4-yl-C(O)-pyrrolidin-3-yl* | 1.61 | 459.2 | 13a2 & Ex. 14 |
| 1064 | 1H-pyrazol-4-yl-C(O)-pyrrolidin-3-yl* | 1.5 | 444.3 | 13a2 & Ex. 14 |
| 1065 | 3-amino-1H-pyrazol-4-yl-C(O)-pyrrolidin-3-yl* | 1.49 | 459.3 | 13a2 & Ex. 14 |
| 1066 | 6-acetamidopyridin-3-yl-C(O)-pyrrolidin-3-yl* | 1.58 | 512.3 | 13a2 & Ex. 14 |
| 1067 | pyridazin-3-yl-C(O)-pyrrolidin-3-yl* | 1.51 | 456.3 | 13a2 & Ex. 14 |
| 1068 | 1-methyl-1H-1,2,3-triazol-4-yl-C(O)-pyrrolidin-3-yl* | 1.54 | 459.3 | 13a2 & Ex. 14 |
| 1069 | imidazo[1,2-a]pyrimidin-2-yl-C(O)-pyrrolidin-3-yl* | 1.53 | 495.3 | 13a2 & Ex. 14 |
| 1070 | 5-isopropyl-4H-1,2,4-triazol-3-yl-C(O)-pyrrolidin-3-yl* | 1.67 | 487.3 | 13a2 & Ex. 14 |

TABLE 1-continued

| Cmpd # | R⁴ | t_R (min) | (M + H)⁺ | Ex. # |
|---|---|---|---|---|
| 1071 | oxazol-5-yl-C(O)-pyrrolidin-3-yl* | 1.52 | 445.3 | 13a2 & Ex. 14 |
| 1072 | 1-methyl-1H-pyrazol-3-yl-C(O)-pyrrolidin-3-yl* | 1.6 | 458.3 | 13a2 & Ex. 14 |
| 1073 | 1-methyl-1H-imidazol-2-yl-C(O)-pyrrolidin-3-yl* | 1.6 | 458.3 | 13a2 & Ex. 14 |
| 1074 | 1-methyl-1H-pyrazol-5-yl-C(O)-pyrrolidin-3-yl* | 1.61 | 458.3 | 13a2 & Ex. 14 |
| 1075 | 6-aminopyridin-3-yl-C(O)-pyrrolidin-3-yl* | 1.44 | 470.3 | 13a2 & Ex. 14 |
| 1076 | 5-(methylsulfonyl)pyridin-2-yl-C(O)-pyrrolidin-3-yl* | 1.57 | 533.3 | 13a2 & Ex. 14 |
| 1077 | 6-(methylsulfonyl)pyridin-3-yl-C(O)-pyrrolidin-3-yl* | 1.52 | 533.3 | 13a2 & Ex. 14 |
| 1078 | pyrimidin-5-yl-C(O)-pyrrolidin-3-yl* | 1.51 | 456.3 | 13a2 & Ex. 14 |

TABLE 1-continued
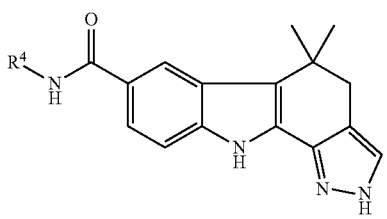
| Cmpd # | R⁴ | t_R (min) | (M + H)⁺ | Ex. # |
|---|---|---|---|---|
| 1079 | 5-amino-pyridin-3-yl-C(O)-pyrrolidin-3-yl* | 1.47 | 470.3 | 13a2 & Ex. 14 |
| 1080 | 6-hydroxy-pyridin-3-yl-C(O)-pyrrolidin-3-yl* | 1.47 | 471.3 | 13a2 & Ex. 14 |
| 1081 | isothiazol-5-yl-C(O)-pyrrolidin-3-yl* | 1.65 | 461.2 | 13a2 & Ex. 14 |
| 1082 | 5-amino-1H-pyrazol-3-yl-C(O)-pyrrolidin-3-yl* | 1.46 | 459.3 | 13a2 & Ex. 14 |
| 1083 | 5-amino-1,3,4-thiadiazol-2-yl-C(O)-pyrrolidin-3-yl* | 1.55 | 477.2 | 13a2 & Ex. 14 |
| 1084 | pyridin-3-yl-C(O)-3,3-dimethylpyrrolidin-4-yl* | 2.14 | 469.4 | 13g2 & Ex. 14 |
| 1085 | 6-methylpyridin-3-yl-C(O)-3,3-dimethylpyrrolidin-4-yl* | 2.24 | 483.4 | 13g2 & Ex. 14 |

TABLE 1-continued
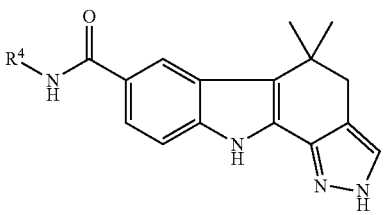
| Cmpd # | R⁴ | t_R (min) | (M + H)⁺ | Ex. # |
|---|---|---|---|---|
| 1086 | 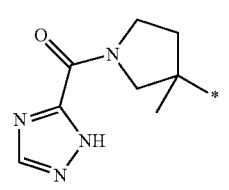 [SMILES: *C1(C)CCN(C(=O)c2ncn[nH]2)C1] | 2.21 | 468.4 | 13g2 & Ex. 14 |
| 1087 | 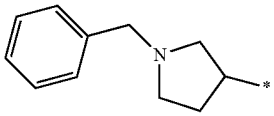 [SMILES: *C1CCN(Cc2ccccc2)C1] | 2.08 | 459.3 | 13g2 & Ex. 14 |
| 1088 | 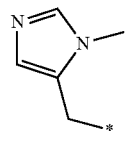 | 1.5 | 440.3 | Ex. 15 |
| 1089 | 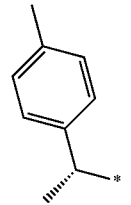 | 1.25 | 375.3 | Ex. 15 |
| 1090 | 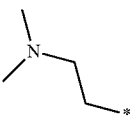 [SMILES: *CCN(C)C] | 1.99 | 399.3 | Ex. 15 |
| 1091 | 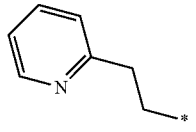 [SMILES: *CCc1ccccn1] | 1.22 | 352.3 | Ex. 15 |
| 1092 | 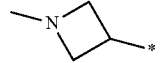 [SMILES: *C1CN(C)C1] | 1.6 | 386.3 | Ex. 15 |
| 1093 | 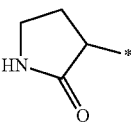 [SMILES: *C1CCNC1=O] | 1.19 | 350.3 | Ex. 15 |
| 1094 |  | 1.46 | 364.3 | Ex. 15 |

TABLE 1-continued
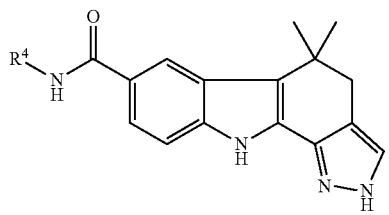
| Cmpd # | R⁴ | t_R (min) | (M + H)⁺ | Ex. # |
|---|---|---|---|---|
| 1095 | 1-ethylpiperidin-3-yl | 1.31 | 392.3 | Ex. 15 |
| 1096 | 2-(tetrahydro-2H-pyran-4-yl)ethyl | 1.73 | 393.3 | Ex. 15 |
| 1097 | tetrahydro-2H-pyran-3-yl | 1.67 | 365.3 | Ex. 15 |
| 1098 | 2-(5-methyl-4H-1,2,4-triazol-3-yl)ethyl | 1.5 | 390.3 | Ex. 15 |
| 1099 | 2-(pyrrolidin-1-ylsulfonyl)ethyl | 1.65 | 442.2 | Ex. 15 |
| 1100 | 2-(N,N-dimethylsulfamoyl)ethyl | 1.57 | 416.2 | Ex. 15 |
| 1101 | 3-(1H-1,2,4-triazol-1-yl)propyl | 1.52 | 390.3 | Ex. 15 |
| 1102 | 2-(isopropylsulfonyl)ethyl | 1.58 | 415.2 | Ex. 15 |

TABLE 1-continued
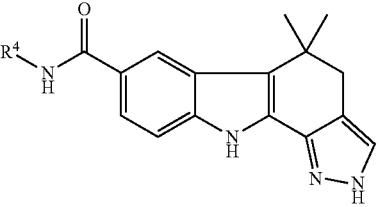
| Cmpd # | R⁴ | t_R (min) | (M + H)⁺ | Ex. # |
|---|---|---|---|---|
| 1103 | 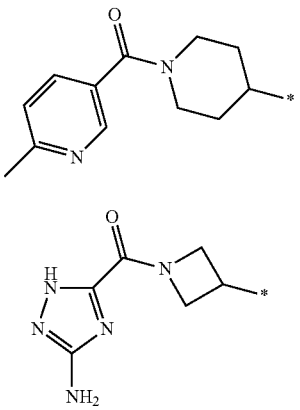 | 1.65 | 483.3 | 13e2 & Ex. 14 |
| 1104 | 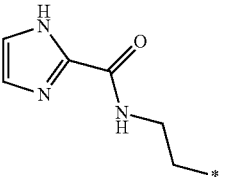 [SMILES: *CCNC(=O)c1ncc[nH]1] | 1.43 | 446.3 | 13b2 & Ex. 14 |
| 1105 | 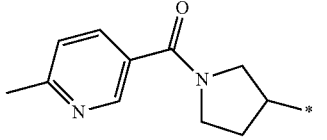 [SMILES: *C1CCN(C(=O)c2ccc(C)nc2)C1] | 1.52 | 418.2 | 13h2 & Ex. 14 |
| 1106 | 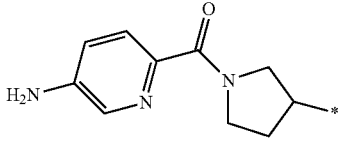 [SMILES: *C1CCN(C(=O)c2ccc(N)cn2)C1] | 1.61 | 469.3 | 13a2 & Ex. 14 |
| 1107 | 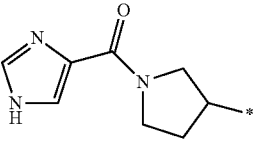 [SMILES: *C1CCN(C(=O)c2c[nH]cn2)C1] | 1.52 | 470.3 | 13a2 & Ex. 14 |
| 1108 | 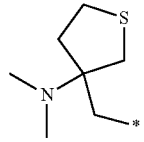 [SMILES: *CC1(N(C)C)CCSC1] | 1.46 | 444.2 | 13a2 & Ex. 14 |
| 1109 | 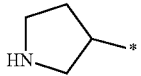 | 1.38 | 424.3 | Ex. 15 |
| 1110 |  | 1.15 | 350.3 | Ex. 13 (13a2) |

TABLE 1-continued

| Cmpd # | R⁴ | t_R (min) | (M + H)⁺ | Ex. # |
|---|---|---|---|---|
| 1111 | 2-fluoroethyl-pyrrolidin-3-yl | 1.28 | 396.3 | Ex. 15 |
| 1112 | 1-methylpiperidin-4-yl | 1.23 | 378.3 | Ex. 15 |
| 1113 | 1,3-dimethoxypropan-2-yl | 1.64 | 383.2 | Ex. 15 |
| 1114 | oxetan-3-yl | 1.5 | 337 | Ex. 15 |
| 1115 | 3-hydroxy-1,1-dioxidotetrahydrothiophen-4-yl | 1.4 | 415.1 | Ex. 15 |
| 1116 | (1,1-dioxidotetrahydrothiophen-3-yl)methyl | 1.44 | 413.2 | Ex. 15 |
| 1117 | 1-(dimethylcarbamoyl)pyrrolidin-3-yl | 1.6 | 421.1 | Ex. 17 |
| 1118 | 1-(isopropylcarbamoyl)pyrrolidin-3-yl | 1.61 | 435.2. | Ex. 18 |
| 1119 | 4-(1H-1,2,4-triazole-3-carboxamido)cyclohexyl | 473.3 | 473.3 | 13i2 & Ex. 14 |

TABLE 1-continued
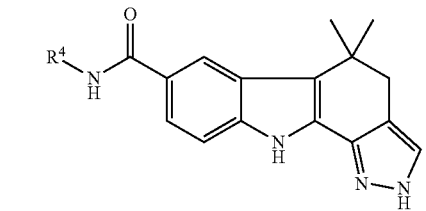
| Cmpd # | R[4] | $t_R$ (min) | (M + H)[+] | Ex. # |
|---|---|---|---|---|
| 1120 | 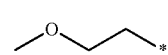 | 2.13 | 473.2 | 13f2 & Ex. 14 |
| 1121 |  | 1.55 | 339.1 | Ex. 15 |
| 1122 | 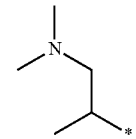 | 1.68 | 323.1 | Ex. 15 |
| 1123 | 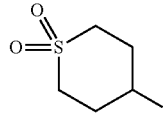 | 1.29 | 366.2 | Ex. 15 |
| 1124 | 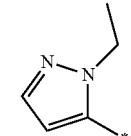 | 1.94 | 413.1 | Ex. 21 |
| 1125 | 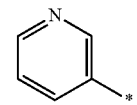 | 1.63 | 375.1 | Ex. 16 |
| 1126 | 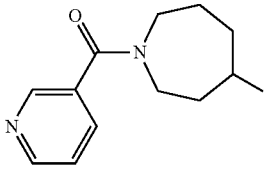 | 1.66 | 358.1 | Ex. 16 |
| 1127 | 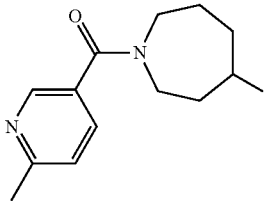 | 2.15 | 483.2 | 13d2 & Ex. 14 |
| 1128 |  | 2.25 | 497.2 | 13d2 & Ex. 14 |

TABLE 1-continued
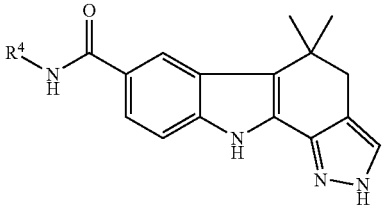
| Cmpd # | R⁴ | $t_R$ (min) | (M + H)⁺ | Ex. # |
|---|---|---|---|---|
| 1129 | 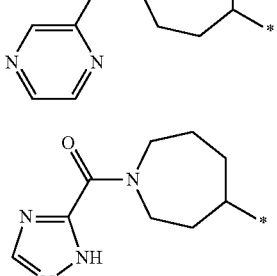 | 2.14 | 484.2 | 13d2 & Ex. 14 |
| 1130 | 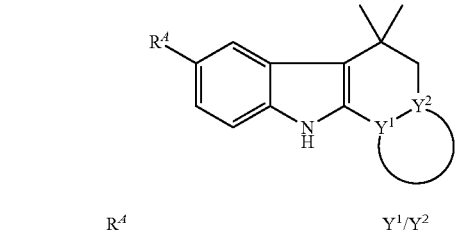 | 2.04 | 473.2 | 13d2 & Ex. 14 |
TABLE 2
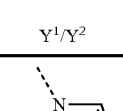
| Cmpd # | R⁴ | Y¹/Y² | $t_R$ (min) | (M + H)⁺ | Ex. # |
|---|---|---|---|---|---|
| 2001 | 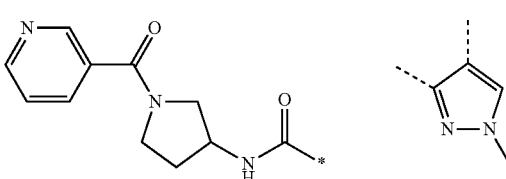 | 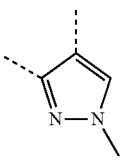 | 1.28 | 373.3 | Ex. 27 |
| 2002 | 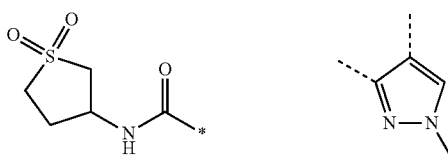 | | 1.63 | 469.3 | Ex. 42 |
| 2003 | 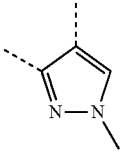 | | 1.59 | 413.2 | Ex. 32 |
| 2004 | 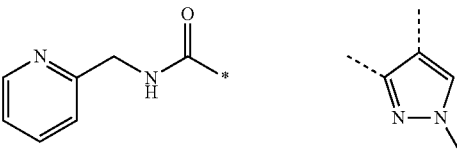 | 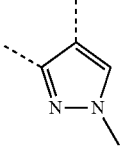 | 1.72 | 386.2 | Ex. 32 |

TABLE 2-continued

| Cmpd # | R⁴ | Y¹/Y² | t_R (min) | (M + H)⁺ | Ex. # |
|---|---|---|---|---|---|
| 2005 | HOOC-* (carboxylic acid) | pyrazol-4-yl | 1.00 | 282.2 | Ex. 2 (2a4) |
| 2006 | 2,3-dihydro-1H-pyrrolo[3,4-c]pyridine-2-carbonyl-* | pyrazol-4-yl | 1.59 | 384.3 | Ex. 15 |
| 2007 | (1,1-dioxidotetrahydrothiophen-3-yl)aminocarbonyl-* | 1-methyl-imidazol-2-yl | 1.17 | 399.1 | Ex. 29 |
| 2008 | (pyridin-2-ylmethyl)aminocarbonyl-* | 5-methyl-1H-pyrazol-3-yl | 1.72 | 386.3 | Ex. 5 |
| 2009 | (1,1-dioxidotetrahydrothiophen-3-yl)(methyl)aminocarbonyl-* | pyrazol-4-yl | 1.45 | 413.2 | Ex. 15 |
| 2010 | (1,1-dioxidothiomorpholin-4-yl)carbonyl-* | pyrazol-4-yl | 1.45 | 399.1 | Ex. 15 |
| 2011 | (pyridin-2-ylmethyl)aminocarbonyl-* | 1-methyl-imidazol-2-yl | 1.27 | 372.1 | Ex. 29 |
| 2012 | (tetrahydro-2H-pyran-4-yl)aminocarbonyl-* | 1-methyl-imidazol-2-yl | 1.26 | 365.2 | Ex. 29 |

TABLE 2-continued

| Cmpd # | R$^A$ | Y$^1$/Y$^2$ | t$_R$ (min) | (M + H)$^+$ | Ex. # |
|---|---|---|---|---|---|
| 2013 | pyridin-2-ylmethyl-NH-C(O)-* | thiazol-2-amine (4,5-linked) | 1.63 | 404.1 | Ex. 34 |
| 2014 | 1,1-dioxidotetrahydrothiophen-3-yl-NH-C(O)-* | thiazol-2-amine (4,5-linked) | 1.5 | 431.1 | Ex. 34 |
| 2015 | 1-(pyridin-3-ylcarbonyl)pyrrolidin-3-yl-NH-C(O)-* | thiazol-2-amine (4,5-linked) | 1.56 | 487.1 | Ex. 39 |
| 2016 | pyridin-3-ylmethyl-N(Me)-C(O)-* | 1H-pyrazole (3,4-linked) | 1.58 | 386.2 | Ex. 15 |
| 2017 | pyridin-2-ylmethyl-NH-C(O)-* | 2-methylthiazole (4,5-linked) | 1.86 | 403.1 | Ex. 31 |
| 2018 | 1,1-dioxidotetrahydrothiophen-3-yl-NH-C(O)-* | 2-methylthiazole (4,5-linked) | 1.76 | 430.1 | Ex. 31 |
| 2019 | 1-(pyridin-3-ylcarbonyl)pyrrolidin-3-yl-NH-C(O)-* | 2-methylthiazole (4,5-linked) | 1.79 | 486.2 | Ex. 40 |
| 2020 | MeO-C(O)-* | 1H-pyrazole (3,4-linked) | 2.59 | 296 | Ex. 20 |

TABLE 2-continued

| Cmpd # | R⁴ | Y¹/Y² | $t_R$ (min) | (M + H)⁺ | Ex. # |
|---|---|---|---|---|---|
| 2021 | (3-acetamido-1,1-dioxo-tetrahydrothiophene) | 2-aminopyrimidin-4-yl | 1.67 | 426 | Ex. 35 |
| 2022 | (pyridin-2-ylmethyl)amide | 2-aminopyrimidin-4-yl | 1.91 | 399.1 | Ex. 35 |
| 2023 | (pyridin-2-ylmethyl)amide | 2-methylpyrimidin-5-yl | 2.27 | 398.1 | Ex. 33 |
| 2024 | 1-(nicotinoyl)pyrrolidin-3-yl acetamide | 2-aminopyrimidin-4-yl | 1.82 | 482.2 | Ex. 38 |
| 2025 | 1-(6-methylnicotinoyl)pyrrolidin-3-yl acetamide | 2-aminopyrimidin-4-yl | 1.94 | 496.1 | Ex. 38 |
| 2026 | 1-(5-amino-1H-1,2,4-triazole-3-carbonyl)pyrrolidin-3-yl acetamide | 2-aminopyrimidin-4-yl | 1.63 | 487.1 | Ex. 38 |
| 2027 | 1-(1H-1,2,4-triazole-3-carbonyl)pyrrolidin-3-yl acetamide | 2-aminopyrimidin-4-yl | 1.72 | 472.2 | Ex. 38 |

TABLE 2-continued

| Cmpd # | R⁴ | Y¹/Y² | t_R (min) | (M + H)⁺ | Ex. # |
|---|---|---|---|---|---|
| 2028 | (3-acetamido-tetrahydrothiophene 1,1-dioxide) | pyrimidine | 1.53 | 425 | Ex. 33 |
| 2029 | (5-isopropylamino-1,3,4-oxadiazole) | pyrazole | 1.84 | 363.3 | Ex. 45 |

TABLE 3

| Cmpd # | R⁴ | t_R (min) | (M + H)⁺ | Ex. # |
|---|---|---|---|---|
| 3001 | 5-oxopyrrolidin-2-ylmethyl | 1.5 | 390.3 | Ex. 30 |
| 3002 | (1H-1,2,4-triazol-3-yl)carbonyl-pyrrolidin-3-yl | 1.4 | 457.3 | Ex. 36 |
| 3003 | pyridin-3-ylcarbonyl-pyrrolidin-3-yl | 1.53 | 467.3 | Ex. 36 |
| 3004 | pyridin-2-ylmethyl | 1.62 | 384.2 | Ex. 30 |
| 3005 | tetrahydrothiophene 1,1-dioxide-3-yl | 1.48 | 411.2 | Ex. 30 |
| 3006 | N-(pyridin-3-ylcarbonyl)aminoethyl | 1.57 | 441.3 | Ex. 30 |
| 3007 | (5-methylpyrazin-2-yl)methyl | 1.63 | 399.3 | Ex. 30 |
| 3008 | N-((5-methylpyrazin-2-yl)carbonyl)aminoethyl | 1.64 | 456.3 | Ex. 30 |
| 3009 | tetrahydropyran-4-yl | 1.65 | 377.2 | Ex. 30 |

TABLE 3-continued

| Cmpd # | R[4] | $t_R$ (min) | (M + H)[+] | Ex. # |
|---|---|---|---|---|
| 3010 | tetrahydropyran-3-yl | 1.7 | 377.1 | Ex. 30 |
| 3011 | isopropylsulfonyl-ethyl | 1.61 | 427.1 | Ex. 30 |
| 3012 | dimethylaminosulfonyl-ethyl | 1.59 | 428.1 | Ex. 30 |
| 3013 | 3-methyl-1,1-dioxo-tetrahydrothiophen-3-yl | 1.57 | 425.1 | Ex. 30 |
| 3014 | 1-acetyl-pyrrolidin-3-yl | 1.56 | 404.3 | Ex. 36 |
| 3015 | 1-(tetrahydrofuran-2-carbonyl)-pyrrolidin-3-yl | 1.63 | 460.4 | Ex. 36 |
| 3016 | 1-(3-amino-1H-pyrazole-5-carbonyl)-pyrrolidin-3-yl | 1.49 | 471.4 | Ex. 36 |
| 3017 | 1-(1-methyl-imidazole-2-carbonyl)-pyrrolidin-3-yl | 1.64 | 470.4 | Ex. 36 |
| 3018 | 1-(pyridine-2-carbonyl)-pyrrolidin-3-yl | 1.64 | 467.3 | Ex. 36 |
| 3019 | 1-(6-methyl-pyridine-3-carbonyl)-pyrrolidin-3-yl | 1.63 | 481.1 | Ex. 36 |
| 3020 | 1-(5-methylsulfonyl-pyridine-2-carbonyl)-pyrrolidin-3-yl | 1.57 | 545.2 | Ex. 36 |
| 3021 | 1-(pyrazine-2-carbonyl)-pyrrolidin-3-yl | 1.6 | 468 | Ex. 36 |

TABLE 4

| Cmpd # | R[4] | $t_R$ (min) | (M + H)[+] | Ex. # |
|---|---|---|---|---|
| 4001 | 1-(pyridine-3-carbonyl)-pyrrolidin-3-yl | 1.67 | 481.3 | Ex. 43 |
| 4002 | 1-(1H-1,2,4-triazole-3-carbonyl)-pyrrolidin-3-yl | 1.62 | 471.2 | Ex. 44 |

TABLE 4-continued

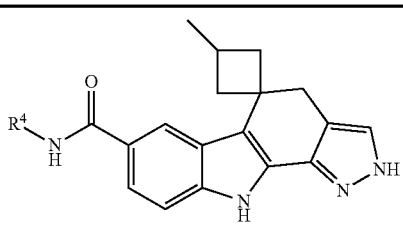

| Cmpd # | R⁴ | $t_R$ (min) | (M + H)⁺ | Ex. # |
|---|---|---|---|---|
| 4003 | (tetrahydrothiophene 1,1-dioxide) | 1.63 | 425.2 | Ex. 37 |
| 4004 | (2-pyridylmethyl) | 1.76 | 398.3 | Ex. 37 |

TABLE 5

| Cmpd # | Structure | $t_R$ (min) | (M + H)⁺ | Ex. # |
|---|---|---|---|---|
| 5001 | (structure) | 1.49 | 358.2 | Ex. 23 |
| 5002 | (structure) | 1.33 | 431.2 | Ex. 41 |
| 5003 | (structure) | 1.38 | 441.3 | Ex. 41 |

Each reference, including all patents, patent applications, and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:

1. A compound, or a pharmaceutically acceptable salt thereof, having a formula

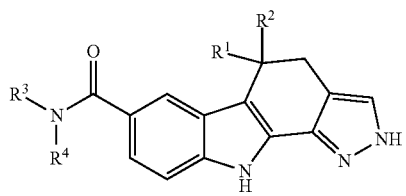

wherein:

$R^1$ and $R^2$ are each independently $(C_{1-6})$alkyl optionally monosubstituted or disubstituted with —O—$(C_{1-6})$alkyl, $NH_2$, $NH(C_{1-6})$alkyl or $N((C_{1-6})$alkyl$)_2$;

$R^3$ is H or $(C_{1-6})$alkyl optionally monosubstituted or disubstituted with —O—$(C_{1-6})$alkyl, $NH_2$, $NH(C_{1-6})$alkyl, $N((C_{1-6})$alkyl$)_2$, —C(=O)—$(C_{1-6})$alkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —C(=O)—$NH_2$, —C(=O)—NH$(C_{1-6})$alkyl or —C(=O)—N$((C_{1-6})$alkyl$)_2$;

$R^4$ is H, $(C_{1-6})$alkyl, $(C_{3-7})$cycloalkyl, —$(C_{1-6})$alkyl-aryl, —$(C_{1-6})$alkyl-heterocyclyl, —$(C_{1-6})$alkyl-heteroaryl, aryl, heterocyclyl or heteroaryl, wherein each alkyl, cycloalkyl, aryl, heterocyclyl and heteroaryl, either alone or in combination with another radical, is optionally substituted with 1, 2 or 3 $R^{41}$; or R$^3$ and R$^4$, together with the nitrogen atom to which they are attached, are linked to form a heterocyclyl or heteroaryl, wherein heterocyclyl and heteroaryl are each optionally substituted with 1, 2 or 3 R$^{41}$;

R$^{41}$ is each independently selected from the group consisting of halo, oxo, cyano, nitro, R$^{42}$, —C(=O)—R$^{42}$, —C(=O)OR$^{42}$, —OR$^{42}$, —SR$^{42}$, —SOR$^{42}$, —SO$_2$R$^{42}$, —N(R$^{43}$)R$^{42}$, —C(=O)—N(R$^{43}$)R$^{42}$, —N(R$^{43}$)—C(=O)R$^{42}$, —O—C(=O)—N(R$^{43}$)R$^{42}$ and —SO$_2$—N(R$^{43}$)R$^{42}$;

R$^{42}$ is each independently selected from the group consisting of H, (C$_{1-6}$)alkyl, (C$_{3-7}$)cycloalkyl, —(C$_{1-6}$)alkyl-aryl, —(C$_{1-6}$)alkyl-heterocyclyl, —(C$_{1-6}$)alkyl-heteroaryl, aryl, heterocyclyl and heteroaryl, wherein each alkyl, cycloalkyl, aryl, heterocyclyl and heteroaryl, either alone or in combination with another radical, is optionally substituted with 1, 2 or 3 substituents each independently selected from the group consisting of:

halo, cyano, OH, —COOH, —O—(C$_{1-6}$)alkyl, (C$_{3-7}$)cycloalkyl, (C$_{1-6}$)haloalkyl, —C(=O)—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO$_2$(C$_{1-6}$)alkyl, —C(=O)—NH$_2$, —C(=O)—NH(C$_{1-6}$)alkyl, —C(=O)—N((C$_{1-6}$)alkyl)$_2$, —NH$_2$, —NH(C$_{1-6}$)alkyl, —N((C$_{1-6}$)alkyl)$_2$, —NH—C(=O)(C$_{1-6}$)alkyl and (C$_{1-6}$)alkyl optionally monosubstituted or disubstituted with OH or —O—(C$_{1-6}$)alkyl; and R$^{43}$ is H or (C$_{1-6}$)alkyl.

2. The compound according to claim 1, or a pharmaceutically acceptable salt thereof, wherein R$^1$ and R$^2$ are each CH$_3$.

3. The compound according to claim 1, or a pharmaceutically acceptable salt thereof, wherein R$^3$ is H.

4. The compound according to claim 1, or a pharmaceutically acceptable salt thereof, wherein R$^4$ is a nitrogen containing heterocyclyl, optionally monosubstituted or disubstituted with R$^{41}$, R$^{41}$ is each independently selected from the group consisting of R$^{42}$, —C(=O)—R$^{42}$ and —SO$_2$R$^{42}$; and R$^{42}$ is each independently selected from the group consisting of (C$_{1-6}$)alkyl, (C$_{5-7}$)cycloalkyl, —(C$_{1-4}$)alkyl-heterocyclyl, —(C$_{1-4}$)alkyl-heteroaryl, heterocyclyl and heteroaryl, wherein each alkyl, cycloalkyl, heterocyclyl and heteroaryl, either alone or in combination with another radical, is optionally monosubstituted or disubstituted with substitutents each independently selected from the group consisting of:

halo, OH, —O—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO$_2$(C$_{1-6}$)alkyl, —NH$_2$, —NH(C$_{1-6}$)alkyl, —N((C$_{1-6}$)alkyl)$_2$, —NH—C(=O)(C$_{1-6}$)alkyl and (C$_{1-6}$)alkyl.

5. A pharmaceutical composition comprising a compound according to claim 1, or a pharmaceutically acceptable salt thereof, and a pharmaceutically acceptable carrier.

6. The pharmaceutical composition according to claim 5 further comprising a therapeutically effective amount of at least one additional antiviral agent.

* * * * *